(12) United States Patent
Travassos

(10) Patent No.: US 11,479,604 B2
(45) Date of Patent: Oct. 25, 2022

(54) IMMUNOMODULATORY PEPTIDES AND METHODS FOR MODULATING THE IMMUNE SYSTEM IN A SUBJECT

(71) Applicant: Recepta Biopharma S.A., São Paulo (BR)

(72) Inventor: Luiz Rodolpho Raja Gabaglia Travassos, São Paulo (BR)

( * ) Notice: Subject to any disclaimer, the term of this patent is extended or adjusted under 35 U.S.C. 154(b) by 87 days.

(21) Appl. No.: 16/627,924

(22) PCT Filed: Jun. 29, 2018

(86) PCT No.: PCT/BR2018/050220
§ 371 (c)(1),
(2) Date: Dec. 31, 2019

(87) PCT Pub. No.: WO2019/006529
PCT Pub. Date: Jan. 10, 2019

(65) Prior Publication Data
US 2021/0147534 A1    May 20, 2021

Related U.S. Application Data

(60) Provisional application No. 62/528,050, filed on Jul. 1, 2017.

(51) Int. Cl.
| | | |
|---|---|---|
| *A61P 37/04* | (2006.01) | |
| *A61P 37/06* | (2006.01) | |
| *A61P 35/04* | (2006.01) | |
| *A61K 39/00* | (2006.01) | |
| *C07K 16/28* | (2006.01) | |
| *C07K 16/30* | (2006.01) | |
| *C12N 5/0784* | (2010.01) | |

(52) U.S. Cl.
CPC ............ *C07K 16/28* (2013.01); *A61P 35/04* (2018.01); *A61P 37/04* (2018.01); *A61P 37/06* (2018.01); *C07K 16/30* (2013.01); *C12N 5/0639* (2013.01); *A61K 2039/505* (2013.01); *C07K 2317/24* (2013.01); *C07K 2317/565* (2013.01); *C07K 2317/76* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 9,193,797 B2 * | 11/2015 | Travassos | .......... C07K 16/3069 |
| 2013/0315902 A1 * | 11/2013 | Travassos | .............. A61K 36/10 424/133.1 |
| 2016/0108132 A1 | 4/2016 | Travassos | |

OTHER PUBLICATIONS

Coleman, Research in Immunology 145(1):33-36, 1994.*
Edwards et al J. Mol. Biol., 334:103-118, 2003.*
International Search Report dated Jun. 28, 2019, International Patent Application No. PCT/BR2018/050220.
Written Opinion dated Jun. 28, 2019, International Patent Application No. PCT/BR2018/050220.
Figueiredo, CR., et al., 2015 "A Novel Microtubule De-Stabilizing Complementarity-Determining Region $C_{36}L_1$ Peptide Displays Antitumor Activity Against Melanoma In Vitro and In Vivo," Scientific Reports, vol. 5, No. 14310; pp. 1-17.
Girola, N., et al., 2006 "The Ig VH Complementarity-Determining Region 3-Containing Rb9 Peptide, Inhibits Melanoma Cells Migration and Invasion by Interactions with Hsp90 and an Adhesion G-Protein Coupled Receptor," Peptides. vol. 85; pp. 1-15.

* cited by examiner

*Primary Examiner* — Patricia Duffy
(74) *Attorney, Agent, or Firm* — Knobbe, Martens, Olson & Bear, LLP

(57) ABSTRACT

Peptides have immune system modulation properties. The immunologically active peptides can be derived from the heavy-chain complementarity determining region-3 of a humanized monoclonal antibody to NaPi2B transporter. Such peptides can be used to modulate the immune system of a subject under cancer treatment.

8 Claims, 35 Drawing Sheets
Specification includes a Sequence Listing.

Human mo-DC induction of allogeneic lymphocytes' proliferation

| Stimulus | Total cells % prolif | CD4 % prolif | CD8 % prolif | CD4/CD8 index |
|---|---|---|---|---|
| negative control | 2.0 | 0.6 | 3.3 | 0.18 |
| PHA | 88.6 | 91.9 | 96.7 | 0.95 |
| mDC | 16.0 | 12.8 | 15.3 | 0.84 |
| Tu lysate | 37.4 | 15.6 | 19.3 | 0.81 |
| mDC + Tu lysate | 39.1 | 16.5 | 15.5 | 1.06 |
| mDC + Rb9 + Tu lysate | 50.9 | 37.3 | 34.9 | 1.07 |

IMMUNOMODULATORY PEPTIDES AND METHODS FOR MODULATING THE IMMUNE SYSTEM IN A SUBJECT

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 31943008_1.TXT, the date of creation of the ASCII text file is Dec. 31, 2019, and the size of the ASCII text file is 3.21 KB.

TECHNOLOGY FIELD

The present disclosure refers to peptides having immune system modulation properties. More specifically, the present disclosure refers to immunologically active peptides derived from the heavy-chain complementarity determining region-3 of a humanized monoclonal antibody to NaPi2B transporter. Such peptides were found to be useful for the modulation of the immune system of a subject under cancer treatment.

BACKGROUND

Cancer is a leading cause of human death with millions of people dying from it every year. Cancer is a recurrent disease, and the several side effects of currently available cancer treatments stimulate the research for new agents able to inhibit the growth of neoplastic cells.

Neoplastic cells which derive from normal tissue, show abnormal growth, form tumor masses which are nourished by newly formed blood vessels, invade adjacent tissues and may spread to distant sites through the lymphatic and blood circulatory systems (metastasis), inducing immune suppression and death.

Besides their beneficial effects in retarding or arresting the growth of certain types of neoplasms, anticancer drugs may cause impairment of immune function in patients.

Monoclonal antibodies specifically targeting tumor antigens are one of the possible cancer treatment tools, because of their specificity and consequent better efficacy and fewer side effects. One of the most promising properties of monoclonal antibodies is their ability to modulate immune responses.

Immunomodulation

Immunomodulation is the adjustment of the immune response to a desired level, as in immunopotentiation, immunosuppression or induction of immunologic tolerance. Much attention has been given to immunomodulatory monoclonal antibodies, as it has been given before to immunomodulatory antimicrobial peptides (AMPs) (Haney and Hancock, 2013).

However, peptide-induced immunomodulation may also activate signaling pathways, stimulate or regulate the expression of maturation markers on dendritic cells, stimulate antigen presentation, cytokine production and lymphocyte interaction, phenotypes that will define the ultimate immune response. Effector or regulatory T lymphocytes, memory T and B lymphocytes, can be induced, which will determine the anti-infective or anti-tumor effectiveness of the immune response.

Other targets of immunomodulation by peptides and other agents are macrophages. Macrophages can be modulated, or selected, to modify their metabolic functions from "heal-growth promoting" as in M2 macrophages to a "killing/inhibitory function" as in M1 macrophages. In M2 macrophages the arginine metabolism is shifted to ornithine and polyamines. In M1 macrophages it is shifted to NO and citrulline. M2 cells characterized by IL-23$^{lo}$IL-10$^{hi}$TGF-beta$^{hi}$ phenotype take part in polarized Th2 responses, allergy, parasite clearance, dampening of inflammation, tissue remodeling, angiogenesis, immunoregulation, and tumor promotion (Sicas and Mantovani, 2012). Conversely, M1 macrophages are characterized in vitro by an IL-12$^{hi}$IL-23$^{hi}$IL-10$^{lo}$ phenotype; are efficient producers of toxic effector molecules (ROS and NO) and inflammatory cytokines (IL-1beta, TNF, IL-6); participate as inducers and effector cells in polarized Th1 responses; and mediate resistance against intracellular parasites and tumors (Gordon and Taylor, 2005). MIF (Macrophage inhibitory factor), is abundantly produced by melanoma cells and it preferentially stimulates the M2 macrophage differentiation. Interfering in the MIF-CD74 signaling in macrophages and dendritic cells (DCs) can downregulate immunosuppressive factors and activate cytotoxic T cells, thus, restoring the antitumor immune response as in metastatic melanoma (Figueiredo et al., 2018).

Peptides like C36L1 and Rb9 (as presently focused on) bind to MIF and CD74, which may modify their activities and display an anti-tumor effect. Immunomodulation can then be an attribute of peptides engaging DCs as well as macrophages as target cells.

Therefore, apart from monoclonal antibodies specifically targeting tumor antigens, receptors and co-signaling molecules of the immune system, bioactive peptides from a number of sources have been studied with various specificities and affinities for microorganisms and eukaryotic cells. For example, peptides derived from immunoglobulin (Ig) internal sequences have been shown to display differential antimicrobial, anti-viral and anti-tumor activities in vitro and in vivo (Polonelli et al., PLoS One 3(6): e2371, 2008; Magliani et al., Curr Med Chem. 6(18):2305-23, 2009).

The immunoglobulin-superfamily (IgSF) seems to carry the greatest number of domains with peptide sequences displaying biological activities including immunomodulatory ones. IgSF proteins make up over 2% of human genes, the largest family in the human genome (Srinivasan and Roeske, 2005).

Ig-CDR Peptides

Similar to the CDRs of antibodies that represent the antigen combining sites, the high specificity of IgSF (immunoglobulin super-family) receptor-ligand interaction is determined by internal sequences and conformation of CDR-like regions.

Peptide antagonists of the IgSF protein-protein interactions have therapeutic potential in multiple animal models as it has also been described for the antibody CDRs which, when tested as synthetic peptides, display anti-microbial, anti-viral and anti-tumor activities targeting different receptors and systems (Polonelli et al., 2008; Dobroff et al., 2010; Magliani et al., 2012; Figueiredo et al., 2015).

One peptide, AC1001-H3, derived from V$_H$ CDR3 of a murine mAb anti-blood group A showed apoptotic and autophagic effects in vitro in murine B16F10-Nex2 melanoma cells (Rabaca et al., 2016) as well as anti-metastatic activity in a syngeneic melanoma model. This was also the first CDR peptide reported to exert immunomodulatory effects (Gabrielli et al., 2009). This V$_H$CDR3 peptide was taken up by macrophages and stimulated proinflammatory cytokines, the PI3K-Akt signaling pathway and the increased expression of TLR-4 induced by TNF-alpha.

As in melanoma cells in vivo, the peptide also exerted a therapeutic effect against systemic candidiasis without showing direct candidacidal properties. The anti-infective or the anti-tumor activities of CDR peptides comprised three types of responses: a) both in vitro and in vivo anti-infective and/or anti-tumor effects; b) in vitro bioactive responses without in vivo effects; c) in vivo anti-infective and/or anti-tumor effects and absence of in vitro effects against the same target organisms. In vivo, here, means an infectious agent or a tumor cell growing in an animal or human host causing a disease eventually with fatal outcome.

Peptides having anti-tumor activity derived from Igs correspond to hypervariable complementarity determining regions (CDRs) from both light and heavy chains. Immunoglobulin CDRs (Ig-CDR) are antigen-recognizing sequences that, with the exception of heavy chain CDR3, are shared among different antibody families. Such sequences are very diverse, and their length may range from 10aa to 20aa.

Peptides which derive from the complementarity determining region 3 of the heavy-chain of humanized Reb-Mab200 monoclonal antibody have been disclosed, for example, in U.S. Pat. No. 9,193,797 B2. It was shown in U.S. Pat. No. 9,193,797 that synthetic peptides based on sequences derived from $V_H$CDR3 of humanized Reb-Mab200 monoclonal antibody (huMX35, disclosed in the US patent application no. 20160009816) affected in vitro growth of several human tumor cell lines and also inhibited in vivo metastatic growth of melanoma cells in a syngeneic model. Peptide Rb9 and its analogous RB9-MID and Rb10 were described in U.S. Pat. No. 9,193,797 as having anti-tumor activity. Peptides Rb9, Rb9-MID and Rb10 are derived from $V_H$ CDR3 of a monoclonal antibody (mAb) which has affinity to an epitope present in the sodium-phosphate transporter NaPi2b (Yin et al., 2008; US Patent Application No. 2016/0009816).

Biological activity of such peptides has been shown to be independent of mAb specificity (Girola et al. 2016). In fact, Rb9 peptides (SEQ ID: 1) and Rb10 (SEQ ID: 3) showed antitumor activity even against tumor cells that would not have affinity to mAb MX35, such as melanoma cells, indicating that the activity of such peptides is independent of antibody specificity. Antitumor protection by Rb9 is comparable to imiquimod Toll-R binding agent and co-stimulatory with Poly-I:C.

SUMMARY OF THE CLAIMED EMBODIMENTS

However, apart from the antitumor activity it has been recently found that Rb9 and analogous peptides, immunomodulate tumor-bearing mouse splenocyte cytokines, DC costimulatory molecules, lymph node T-CD8+ cell proliferation and TGF-beta inhibition. For example, Rb9 affects the surface phenotype and the lympho-stimulatory activity of human monocyte-derived dendritic cells (mo-DC). It has also been found that Rb9 and other peptides derived from the $V_H$CDR3 of a humanized antibody to NaPi2B, for example Rb9_MID (SEQ ID no. 2) and Rb10 (SEQ ID no. 3), modify the phenotype of mo-DC of cancer patients, correcting their functional bias, enhancing their ability to induce T cell immune responses. Therefore, Rb9 has clear immunomodulatory activities upon dendritic cells, and, depending on their functional status, may inhibit (over-stimulated cells), stimulate (poorly activated or suppressed cells) or cause little phenotypic and functional alterations (in "balanced" cells). Rb9 was previously described as having antitumor properties, in immune competent but not in immune deficient animals, implying the need of a competent immune reaction for in vivo protective activity Peptide Rb9 (SEQ ID: 1) forms an alpha-helix that increases the rigidity and stability of the molecule based on a hairpin structure and numerous H-bonds of high occupancy. The disulfide bond is exposed for reactivity with ligands such as HSP90 and an adhesion G-coupled receptor. On the other hand, Rb10 peptide (SEQ ID: 3) has an open flexible structure without an alpha-helix (Girola et al., 2016). Rb10 (SEQ ID: 3) and the core peptide Rb9-MID (SEQ ID: 2) indicate the importance of the disulfide bond and the core sequence of Rb9 in the immunomodulatory properties of the peptides, considering their efficiency, affinity and target binding specificity. The immunomodulatory activity of Rb9 is also exerted by interactions with MIF and CD74, stimulating the expression of the receptor and modifying the signaling of MIF in antigen presenting cells.

In view of the above, the present disclosure refers to a therapeutic and/or prophylactic method, comprising administering to a subject in need thereof an effective amount of the immunomodulatory peptides, alone or combined with other suitable chemotherapy or immunotherapy agents.

In another embodiment, the present disclosure refers to immunomodulatory peptides alone or combined with other suitable chemotherapy or immunotherapy agents for use in cancer therapy and prophylactics, or the use of such immunomodulatory peptides alone or combined with other suitable chemotherapy or immunotherapy agents for preparing compositions for use in cancer therapy and prophylactics.

Dendritic cells were found to be involved in the immune response induced by the Rb9 peptide, since its protective activity could be reproduced by adoptive transference of dendritic cells, treated ex-vivo with the peptide, into tumor-cell challenged susceptible animals. Therefore, it may be inferred that whatever is the site of peptide inoculation in a tumor-bearing experimental animal, the peptide reaches local and recruited dendritic cells, modulating their activity in a way that leads to tumor regression and prolonged survival of the host. It was also found that Rb9 stimulates dendritic cells that protect against tumor (eg. melanoma) metastatic growth. Rb9 penetrates dendritic cells and migrates to the nucleus thereof for cell signaling.

Therefore, the present disclosure also refers to the immune response-dependent activity of Rb9 and the immunomodulatory effects thereof on human dendritic cells. Such immunomodulatory effects of Rb9 were found to be useful for modulating the immune system of subjects in need thereof, for example subjects under cancer treatment.

Considering the need to develop new alternatives for improving cancer treatment, the present disclosure also refers to peptides for use in methods for modulating the immune response, the methods for modulating the immune response using such peptides and use of such peptides for preparing a medicament for modulating the immune response of a subject, especially the immune response of a subject who has cancer or is under cancer treatment.

Therefore, the present disclosure refers to a method of modulating an immune system response in a subject, such method of modulating an immune system response may be used in a subject who has cancer or is under cancer treatment.

The present disclosure also refers to peptides which are useful for modulating an immune system response in a subject which has cancer or is under cancer treatment.

In another embodiment, the present disclosure refers to the use of peptides for preparing compositions for modulating an immune system response in a subject which has cancer or is under cancer treatment.

More specifically, the present disclosure refers to the immunomodulatory properties of peptides Rb9 (SEQ ID: 1), Rb10 (SEQ ID: 3) and truncated Rb9-MID (SEQ ID: 2), as well as scrambled (Scr) cyclic structures (SEQ ID 4, SEQ ID 5, SEQ ID 6 and SEQ ID 7), which are disclosed herein as potent immunomodulatory agents. As set forth hereinabove, peptide Rb9 (SEQ ID-1) and its analogous are currently known as being useful for inhibiting tumor growth and treating cancer. Nonetheless, the immunomodulatory properties of such peptides were not known.

One of the claimed general embodiments is related to the immunomodulatory properties of Rb9, more specifically to a method of modulating an immune system response in a subject by contacting dendritic cells of the subject with peptides Rb9, or its analogous also described herein. In some particular embodiments, the dendritic cells are contacted with the immunomodulatory peptides in vivo (inside the body) or, alternatively, ex vivo (outside the body). In some particular embodiments, the subject has cancer or is under cancer treatment.

In an alternative general embodiment, the immunomodulatory peptides Rb9, or its analogous also described herein are used in a method of modulating an immune system response in a subject. Such method comprising contacting dendritic cells of the subject with the immunomodulatory peptides. In some particular embodiments, the dendritic cells are contacted with the immunomodulatory peptides in vivo or, alternatively, ex vivo. In some particular embodiments, the subject has cancer or is under cancer treatment.

Another alternative general embodiment is the use of the immunomodulatory peptides Rb9, or its analogous also described herein are for preparing a composition for use in a method of modulating an immune system response in a subject. Such method comprising contacting dendritic cells of the subject with the immunomodulatory peptides. In some particular embodiments applicable to any of those general embodiments described previously, the dendritic cells are contacted with the immunomodulatory peptides in vivo (inside the body) or, alternatively, ex vivo (outside the body). In other particular embodiments, applicable to any one of the embodiments described previously, the subject, which may be an animal or, more specifically, a human, has cancer or is under cancer treatment.

DETAILED DISCLOSURE

The present disclosure relates to immunologically active peptides derived from the heavy-chain complementary determining region-3 of a humanized monoclonal antibody to NaPi2B transporter.

Particularly, the present disclosure concerns the immune response-dependent activity and immunomodulatory effects on human dendritic cells of such immunologically active peptides.

Such immunologically active peptides may be synthetic peptides, which derive from modified, extended sequences of the heavy-chain complementary determining region-3 of a humanized monoclonal antibody to NaPi2B. Exemplary synthetic peptides corresponding to partial sequences of the monoclonal antibody may be, for example, Rb9 (SEQ ID No. 1), Rb10 (SEQ ID: 3) or Rb9-MID (SEQ ID: 2).

In one embodiment, the present disclosure refers to peptides which modulate the immune system of a subject.

In another embodiment, the present invention refers to a method of modulating the immune system of a subject comprising administering to the subject an effective amount of a modified peptide derived from a CDR of a humanized antibody to NaPi2B, such as Rb9 (SEQ ID No. 1), Rb10 (SEQ ID: 3) or Rb9-MID (SEQ ID: 2). Preferably, the method is suitable for modulating an immune system response in a subject who has cancer or is under cancer treatment.

In a particular embodiment, such method comprises administering to the subject an effective amount of a modified peptide derived from a CDR of a humanized antibody to NaPi2B, such as Rb9 (SEQ ID No. 1), Rb10 (SEQ ID: 3) or Rb9-MID (SEQ ID: 2). Alternatively, cells of the subject are contacted with such peptide ex vivo and are then administered to the subject. Such method modulates an immune system response in a subject who has cancer or is under cancer treatment.

In another embodiment, the invention refers to the use of a modified peptide derived from a complementarity determining region (CDR) of a humanized antibody to sodium-dependent phosphate transporter (NaPi2B), such as Rb9 (SEQ ID No. 1), Rb10 (SEQ ID: 3) or Rb9-MID (SEQ ID: 2), for modulating the immune system of a subject. Such use comprises preparing a composition comprising an effective amount of a modified peptide, derived from a CDR of a humanized antibody to NaPi2B. For example, synthetic peptides corresponding to partial sequences of the humanized antibody may be, for example, Rb9 (SEQ ID No. 1), Rb10 (SEQ ID: 3) or Rb9-MID (SEQ ID: 2).

Particularly, such use may comprise simply administering to a subject an effective amount of a modified peptide, derived from a CDR of a humanized antibody to NaPi2B, for example, Rb9 (SEQ ID No. 1), Rb10 (SEQ ID: 3) or Rb9-MID (SEQ ID: 2).

Alternatively, such use may comprise contacting dendritic cells ex vivo with a modified peptide derived from the complementarity determining region (CDR) of a humanized antibody to sodium-dependent phosphate transporter (NaPi2B), for example, Rb9 (SEQ ID No. 1), Rb10 (SEQ ID: 3) or Rb9-MID (SEQ ID: 2).

In another embodiment, the present disclosure refers to a method of treating dendritic cells, the method comprising contacting dendritic cells with a peptide derived from the $V_H$CDR3 of a humanized antibody to NaPi2B and then administered to the subject. Preferably, the peptide is chosen from Rb9 (SEQ ID no. 1), Rb9 MID (SEQ ID no. 2) and Rb10 (SEQ ID no. 3). Preferably, such method modifies the phenotype of the dendritic cells, so that over-stimulated dendritic cells are inhibited, poorly activated or suppressed dendritic cells are stimulated and balanced dendritic cells suffer no functional alteration.

In another embodiment, the invention refers to the use of dendritic cells contacted with a modified peptide derived from the complementarity-determining region (CDR) of a humanized antibody to sodium-dependent phosphate transporter (NaPi2B) to modulate the immune system of a subject.

Preferably, the above-mentioned uses are suitable for modulating an immune system response in a subject who has cancer or is under cancer treatment.

In one aspect of the invention, applicable to any of the above-mentioned embodiments, a sample comprising dendritic cells is contacted with a peptide derived from the CDR of a humanized antibody to NaPi2B and then administered to the subject. For example, synthetic peptides corresponding to partial sequences of the humanized antibody may be, for example, Rb9 (SEQ ID No. 1), Rb10 (SEQ ID: 3) or Rb9-MID (SEQ ID: 2).

In another embodiment, the disclosure refers to peptide Rb9 (SEQ ID No. 1), derived from the CDR of a humanized antibody to NaPi2B, and specifically used as a reagent binding and modifying the activity of MIF and MIF/C74 axis of cell signaling, which stimulate the growth of tumors, increasing the angiogenesis, aggressiveness and metastatic potential of tumor cells. Therefore, the present disclosure also refers to a method wherein the Rb9 (SEQ ID no. 1), functionally controlled by scrambled (Scr) cyclic structures (SEQ ID 5, SEQ ID 6, SEQ ID 7 and SEQ ID 8), bind to MIF and to CD74, and modify the respective signaling, isolated or as a complex, in dendritic cells. Alternatively, the present disclosure refers to the use of Rb9 (SEQ ID no. 1), positively or negatively controlled in their function by scrambled (Scr) cyclic structures (SEQ ID 5, SEQ ID 6, SEQ ID 7 and SEQ ID 8), for preparing compositions for modulating the immune system. Such modulation occurs by binding to MIF and to CD74, and modifying the respective signaling, isolated or as a complex, in dendritic cells.

Therefore, the present disclosure also refers, in general, to Rb9 (SEQ ID no. 1), Scr peptide controls (SEQ ID no. 5, SEQ ID no. 6, SEQ ID no. 7, SEQ ID no. 8) and analogous linear or cyclic structures, which act as immunomodulators via MIF and MIF receptors, and exert anti-cancer properties in experimental animals. As such, methods and uses of such peptides for modulating the immune system of a subject are claimed herein.

In another embodiment of the invention, applicable to any of the above-mentioned methods, peptides and uses, the peptides may be combined with other suitable chemotherapy or immunotherapy agents, such as checkpoint inhibitors like anti-PD-L1, anti-PD-1 or anti-CTLA-4 monoclonal antibodies.

Moreover, the peptide derived from the complementarity determining region (CDR) of a humanized antibody to sodium-dependent phosphate transporter (NaPi2B) may optionally be coupled with a Polyethylene glycol (PEG).

DESCRIPTION OF FIGURES

FIG. 2 also shows cyclic scramble peptides Scr1, Scr2, Scr3 and Scr4 (respectively SEQ IDs: 5, 6, 7, 8) keeping the disulfide bond were designed to serve as controls and to evaluate the specificity of Rb9 antitumor activity.

EXAMPLES

Figure 1:
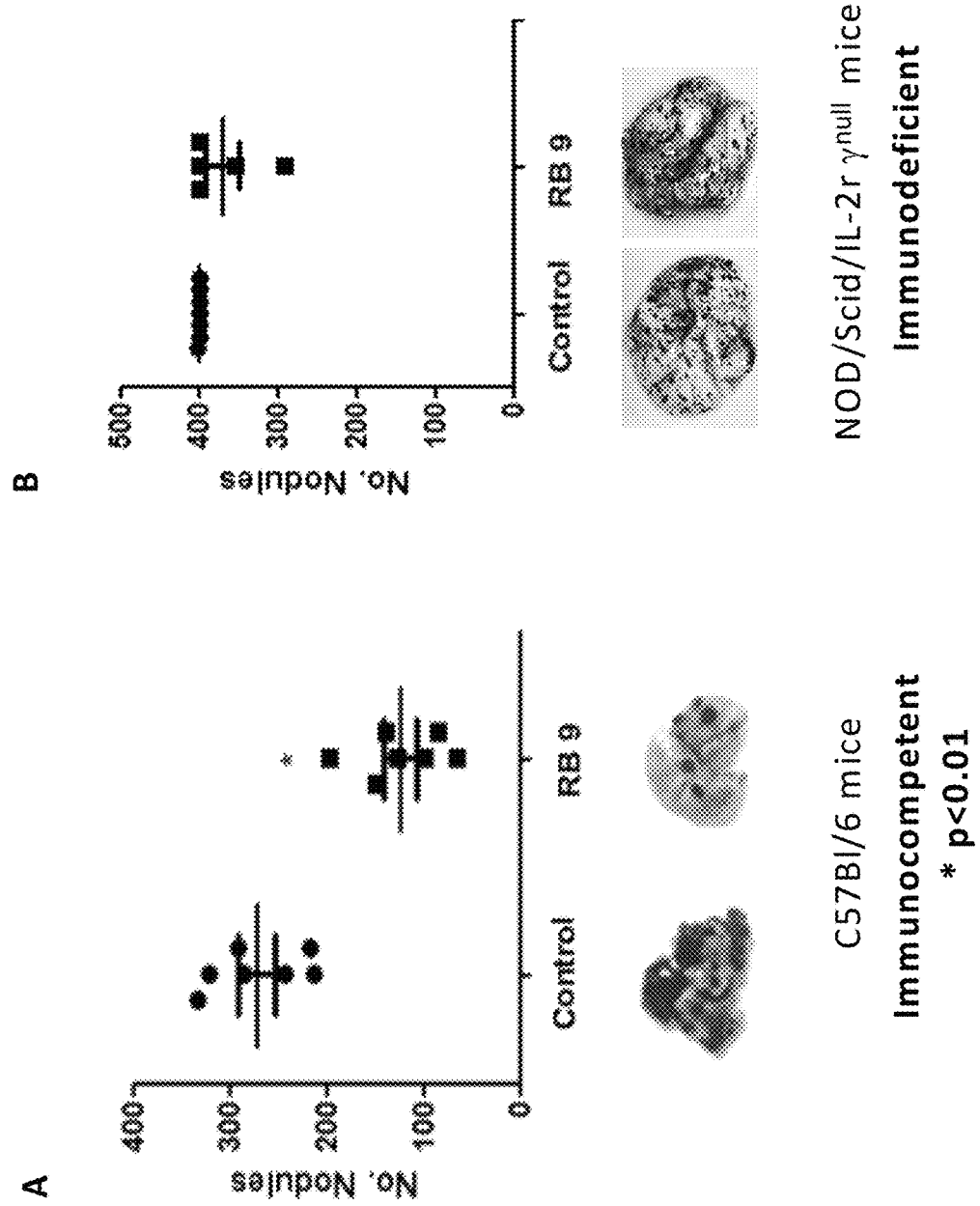
FIG. 1 shows the antitumor effect of Rb9 in a metastatic melanoma model and absence of antitumor effect in immune deficient mice.

The following examples do not intend to limit the scope of the present disclosure and claims. The experiments reported below were carried out with the objective of sufficiently describing the invention in order to allow one skilled in the art to understand the best mode of execution thereof.

Remarks

Short natural peptides when injected in experimental animals are rapidly cleared from blood circulation by renal filtration and degradation by plasma peptidases. To compensate for peptide loss, in vivo experiments usually require dose amounts of 100-300 µg/mouse, which are not cytotoxic in healthy animals. Peptide clearance can also be avoided by increasing the molecular mass of the peptide upon conjugation with polyethylene glycol. We observed that PEG-Rb9 was more efficient than free Rb9 as an antitumor agent in the metastatic melanoma model.

The administration route of the peptide providing the most effective response agrees with the abundance of dendritic cells, which, presumably, are the primary cells of the immune system to interact and to be stimulated by the Ig-CDR. The i.d. route of Rb9 administration also promoted the highest response of anti-melanoma antibodies as measured by chemiluminescent ELISA and B16F10-Nex2 cells. In an ex-vivo system, Rb9 is endocytosed and the primary endosomes partially interact with F-actin and the peptide is transported to the nucleus where it can participate in signaling for immunomodulation of DC function.

In order to correlate immunomodulation with monocyte phenotypes in animals with a growing tumor, a syngeneic metastatic melanoma set up was used with mice being treated with Rb9 or with dendritic cells stimulated ex vivo by Rb9 and primed with melanoma antigens (from a tumor cell lysate). In the absence of tumor lysate, priming could occur in vivo with tumor antigens liberated by tumor cell lysis, aptonecrosis, or any other cross-priming process. Prophylactic and therapeutic protocols with Rb9-stimulated dendritic cells successfully protected against metastatic melanoma in a syngeneic model.

Melanoma i.v. cell challenge and i.p. peptide administration (Rb9 and Rb10A1), led to splenocyte cytokine readings increased in the presence of tumor cell lysate. Rb9 increased IFN-gamma and IL-12, did not change TNF and IL-10 and decreased IL-6 as compared to the untreated melanoma challenged control animals.

Rb9 immunomodulation of murine bone-marrow dendritic cells (DCs) was also examined focusing on co-stimulatory markers. In the LPS stimulated DCs characterized by $CD11c^+$ $MHC-II^+$, Rb9 mainly at 50 µg/ml and Rb10A1 significantly stimulated the expression of CD80 and CD86. In contrast, Rb9 and Rb10-A1 regulated CD40 expression.

Dendritic cells stimulated by Rb9 ex vivo exerted a protective effect against metastatic melanoma following s.c. adoptive transfer. On day 14, mice were inoculated i.v. with B16F10.Nex2 melanoma tumor cells and on day 29, lungs, spleen and cervical and axillary lymph nodes were examined for CD3+ cells, and the proportion of T-CD4+ and T-CD8+ cells. Except for the lungs, treatment with DCs stimulated by Rb9 and Rb10A1 built an immune response in which T-CD8+ cells greatly predominated over T-CD4+ effector cells. Therefore, upon using a favorable protocol, Rb9-stimulated DCs to elicit a T-CD8+ cell immune response protective against metastatic melanoma.

TGF-beta is essential for Tregs to differentiate from naïve CD4+ cells whereas regulatory T cells are involved in counteracting effector cells important in cancer combat. We observed that in the metastatic melanoma set-up Rb9 treatment greatly reduced TGF-beta secreted by the lymph node CD11c+ cells as compared to control cells stimulated by melanoma lysate.

Rb9 inhibition of TGF-beta secretion in the lymph nodes is an indication that Treg is not induced in this system that showed high percentage of T-CD8+ cells.

Poly I:C, a DC agonist that binds to Toll-like receptor 3 (TLR3), is quite active against murine metastatic melanoma. Rb9 adds to this effect. TLR3 is expressed in mouse conventional DCs ($CD11c^{high}B220^{--}$), $CD4^{--}$ $CD8a^{--}$ (+/--) and $CD8^+$ (+) (Seya et al., 2015). To assess the immunomodulatory effects of Rb9 and its core-peptide Rb9-MID (SEQ ID: 2), these peptides were incubated for 60 h with or without Poly I:C with bone marrow DCs obtained by Protocol 2 (see Materials and Methods). Rb9-MID stimulated CD40 expression over Poly I:C much like Rb9. Effects of both peptides on the expression of CD80 were similar. Rb9 but not Rb9-MID stimulated CD86 over Poly I:C, and Rb9-MID significantly increased the expression of MHC II over Poly I:C and Rb9. It seems therefore that the reactivity of Rb9 in vivo or ex-vivo with bone-marrow DCs does not require N-terminal cysteine residues, as with the in vitro anti-tumor direct activity of Rb9 (Girola et al., 2016). The results with Rb9-MID as also with Rb10A1, that does not have a terminal cysteine, replaced by alanine, may help to establish peptide structures needed for immunomodulation properties. Four scrambled peptides (SEQ ID Nos. 5, 6, 7, 8) were tested as Rb9 controls and S-S containing cyclic peptides with positive and negative activities against metastatic melanoma, therefore apt to serve as immunomodulatory controls, particularly against MIF and the MIF/CD74 axis. MIF is an autochrine product of tumor cells which stimulates cytokines, chemokines, angiogenic factors and growth of cancer cells (Nobre et al., 2017). The signal transduction by MIF requires CD74 (Leng et al., 2003). MIF increases Treg by modulating IL-2 production (Choi et al., 2012) and generally regulates the CTL response (Abe et al., 2001). CD4+ T and CD8+ T lymphocytes from tumors of anti-MIF treated mice increased together with the expression of IFN-γ. Previously, the interference of C36L1 peptide on MIF-CD74 immunosuppressive signaling, as reported by Figueiredo et al., 2018, increased the activation of specific CTLs against melanoma cells and decreased Tregs. In the same system, Rb9, which binds to both MIF and CD74, and is protective against metastatic melanoma, administered as a free peptide or as peptide-stimulated DCs, decreased Tregs and increased T effector cells.

These data, obtained in mouse models, supported a significant immunomodulatory activity for the Rb9 peptide that, as the data indicated, exerted its action by enhancing the anti-tumor activity of dendritic cells, either in vivo or ex-vivo. Thus, Rb9 activity was evaluated upon human monocyte-derived dendritic cells (mo-DC). These cells represent an effective alternative for naturally occurring DC which, due to their scarceness are not suitable for use in clinical protocols, but can be replaced by mo-DC, that can be generated in vitro from easily obtainable precursors (Inaba et al., 1992; Sallusto and Lanzavecchia, 1994). This allowed the design of new immunotherapeutic strategies (Berzofsky et al., 2004) based on the unique properties of dendritic cells as triggers of the immune response (Steinman and Witmer, 1978). However, in spite of the potential of these cells, sometimes pointed out also in clinical results (Barbuto et al., 2004), dendritic cell-based vaccines still fail to reach the theoretical potential attributed to them (Barbuto 2013). This apparent failure probably reflects the fact that dendritic cells within tumors (Baleeiro et al., 2008) and those derived from circulating precursors in cancer patients (Ramos et al., 2012) are functionally biased and, therefore, frequently unable to induce effective antitumor T lymphocytes. In this context, the correction of the bias imposed by the presence of the tumor upon dendritic cells is a very attractive path for the development of immunotherapeutic approaches in cancer and the data obtained in the mouse models support that this may be the mechanism of Rb9 activity.

Indeed, Rb9 was able to affect the phenotype of mo-DC, inducing an increased expression of maturation markers, both when used alone or in combination with dendritic cell known activators, like TNF-alpha. Furthermore, Rb9 was also able to enhance the proliferative response of T lymphocytes induced by tumor-lysate pulsed allogeneic DC.

Intriguingly, however, when Rb9 was tested upon mo-DC obtained from cancer patients, though showing the ability to, likewise, enhance the expression of maturation markers, this effect was very heterogeneous. Nonetheless, when the surface and functional phenotype of mo-DC obtained from the patients was taken into consideration, it became possible to discern a clear pattern: mo-DC that had a "normal" phenotype (not clearly distinguishable from that of cells obtained from healthy controls), were little affected by Rb9, but those that had a "defective" phenotype (whose lympho-stimulatory activity was below that of healthy donors' cells), were stimulated by Rb9. Actually, this dichotomy was even more pronounced, since the lympho-stimulatory activity of "normal" mo-DCs was inhibited, while that of the "defective" mo-DCs was increased.

These observations indicated that Rb9 was not a simple activator of DCs but, actually, a molecule that induced restoration of function on these cells in both directions. To test this hypothesis, mo-DCs were generated in conditions that lead to the generation of immune response-inducing DCs or to the generation of tolerance-inducing DCs. For the response-inducing DCs, two different stimuli were used, TNF-alpha and LPS. TNF is a stimulus that induces a "mild" activation of the cells, thus resembling a closer-to-homeostasis situation, while LPS is a stronger stimulus, signaling a clearly more disturbed environment. For the tolerance-inducing DCs, TGF-beta and IL-10 were used (Rutella et al., 2006). When Rb9 was added to these three different mo-DCs, its immunomodulating effects were confirmed. While it affected little the phenotype of TNF-stimulated mo-DCs, it induced the decrease in expression of maturation markers by LPS-stimulated mo-DCs and the increase in the same markers on TGF-beta+IL-10-stimulated mo-DCs.

The data obtained in the experiments with human mo-DCs in vitro are coherent with those obtained in the various mouse models in vivo and in vitro. In bulk, the data point to an immunomodulatory action of Rb9 that can be exploited for cancer immunotherapy and also in other conditions where an unbalanced immune response contributes to the pathogenesis of disease.

Material and Methods

Peptides

Peptides were derivatives of the basic $V_H$CDR3 (H3) sequence from the humanized RebMab200, which matches the specificity of murine MX35 mAb and recognizes a defined peptide epitope on the NaPi2b membrane transporter (Ritter G et al., 2016 Patent application 20160009816). The CDR-derived peptides were amidated at the C-terminal amino acid, were completely solubilized in water or culture medium and were linear or cyclic by adding cysteine and forming a disulfide bond in oxidative condition. N-biotinylated-AGG-Rb9 was also used.

Peptide 2.0 Inc., Chantilly, Va., synthesized all peptides at 85-95% purity. $V_H$ CDR 3 (H3)-derived peptide in the Cys-Cys cyclic configuration (Rb9), added cysteine to the extended sequence (defined as $Cys^{92}$ to $Gly^{104}$) according to Morea et al. (Morea et al., 1998). Two additional amino acids of the sequence, $Gln^{105}$ and $Gly^{106}$ were used as a spacer to avoid linking the new terminal cysteine directly to the H3 sequence. The final Rb9 sequence was C-ARGET-ARATFAYWGQG-C-NH$_2$. (SEQ ID: 1). Rb10 is the linear peptide lacking terminal cysteine. An internal fragment of Rb9 was also synthesized (Rb9-MID). The following peptide sequences in the C-terminal amidic form were studied:

TABLE 1

| | Peptide sequences of the invention | |
|---|---|---|
| Rb9 | [CARGETARATFAYWGQGC], NH$_2$ (C-C),<br>Cys Ala Arg Gly Glu Thr Ala Arg Ala<br>Thr Phe Ala Tyr Trp Gly Gln Gly Cys | SEQ ID: 1 |
| Rb9-MID | [RATFAYWG], NH$_2$<br>Arg Ala Thr Phe Ala Tyr Trp Gly | SEQ ID: 2 |
| Rb10 | [CARGETARATFAYWGQG], NH$_2$<br>Cys Ala Arg Gly Glu Thr Ala Arg Ala<br>Thr Phe Ala Tyr Trp Gly Gln Gly | SEQ ID: 3 |
| Rb10A1 | [AARGETARATFAYWGQG], NH$_2$<br>Ala Ala Arg Gly Glu Thr Ala Arg Ala<br>Thr Phe Ala Tyr Trp Gly Gln Gly | SEQ ID: 4 |
| Scr1 | [CAEATYWRRGGQAAGFTC], NH$_2$ (C-C),<br>Cys Ala Glu Ala Thr Tyr Trp Arg Arg<br>Gly Gly Gln Ala Ala Gly Phe Thr Cys | SEQ ID: 5 |
| Scr2 | [AEACGGYTRWRTCAGAQF], NH$_2$ (C-C),<br>Ala Glu Ala Cys Gly Gly Tyr Thr Arg<br>Trp Arg Thr Cys Ala Gly Ala Gln Phe | SEQ ID: 6 |
| Scr3 | [CETWRGAATRGAFQAYGC], NH$_2$ (C-C),<br>Cys Glu Thr Trp Arg Gly Ala Ala Thr<br>Arg Gly Ala Phe Gln Ala Tyr Gly Cys | SEQ ID: 7 |
| Scr4 | [ACRGAGATWTRQFEGACY], NH$_2$ (C-C)<br>Ala Cys Arg Gly Ala Gly Ala Thr Trp<br>Thr Arg Gln Phe Glu Gly Ala Cys Tyr | SEQ ID: 8 |

Cell Lines and Culture Conditions

The murine melanoma cell line B16F10-Nex2 was originally obtained from the Ludwig Institute for Cancer Research (LICR), São Paulo branch. The subline Nex2 was isolated at the Experimental Oncology Unit, Federal University of São Paulo (UNIFESP), and deposited at Banco de Células do Rio de Janeiro (BCRJ), reg. 0342. All cell lines were cultured at 37° C., under humid atmosphere and 5% $CO_2$, in RPMI-1640 medium with 10 mM N-2-hydroxy-ethyl-piperazine-N-2-ethanesulphonic acid (HEPES), 24 mM sodium bicarbonate, 40 mg/L gentamicin, pH 7.2 and 10% FCS. B16F10-Nex2 is syngeneic in H-2$^b$ C57Bl6 mice. Guillermo D. Mazzolini, Gene therapy Laboratory; School of Medicine, Austral University; Buenos Aires, Argentina, provided additional syngeneic tumor cells, the murine pancreatic carcinoma Panc02 cells, syngeneic in H-2$^b$ C57BL6 and the colon-rectal carcinoma CT26 cells syngeneic in H-2$^d$ Balb/c mice. Another sample of CT26 tumor cells of moderate virulence was obtained from ATCC (CT26.WT cell line; ATCC, CRL-2638).

Animals and an Experimental Melanoma Metastatic Model

Male C57BL/6 mice, 6 to 8-week-old were obtained from the Center for Development of Experimental Models (CEDEME), Federal University of Sao Paulo (UNIFESP). For the in vivo metastatic model, C57BL/6 mice received one intravenous (i.v.) injection of 2×10$^5$ viable B16-F10-Next melanoma cells in 100 µL. To test the therapeutic efficacy of Rb9 and Rb10 along with the control apoptotic peptide A4H3 (Dobroff et al., 2010), intraperitoneal administration of the peptides started one day after injection of tumor cells, with 5-6 doses of 250-300 µg peptide in 100 µL PBS in alternate days. The control group received 100 µL PBS. Twenty-two days later, mice (minimum n=3 per group) had their lungs harvested, and the number of macroscopic melanotic nodules were counted. The Ethical Committee of Federal University of São Paulo, Project no. 1234, 2011, approved all experiments with animals, according to International guidelines. For the subcutaneous model, mice were injected with 5×10$^5$ tumor cells suspended in 100 µL of PBS in the right flank via the subcutaneous route. The peptide (300 µg) was solubilized in 10 µL of distilled $H_2O$ and 90 µL of PBS and injected per mouse via the intraperitoneal route. The administration of the peptide was performed in 5 alternate days initiating one day after tumor challenge. Tumor longitudinal diameter (D) and transverse diameter (d) were measured every 2 days until the tumor volume reached 3,000 mm3. Animals were sacrificed when the allowed volume was reached. Volume was calculated using the formula v=Dd$^2$×0.52.

Tumor Cell Growth In Vitro and In Vivo

Details of the in vitro tumor cell growth, cytotoxicity tests, determination of viable cells and in vivo protection experiments with B16F10 cells in a mouse metastatic model are described in Polonelli et al. (PLoS One. 3(6):e2371, 2008) and Dobroff et al. (Transl. Onc., 3: 204-217, 2010).

Bone-Marrow Dendritic Cell (BMDC) Generation Protocols

BMDC Protocol 1

DCs were obtained from the bone marrow of 6 to 8-week-old C57Bl6 mice. Briefly, femora and tibiae from mice were removed and stripped of muscles and tendons; both bone ends were cut, and bone marrow was extracted by placing the bone pieces into 1-ml tips, which in turn were inserted into 15-ml tubes and centrifuged for 10 minutes at 1500 rpm. Cells were resuspended in DMEM and cell clusters were dissociated by repeated pipetting. The total bone marrow cells were cultured in 100-mm treated tissue culture dish in 10 ml of R10 medium (DMEM medium supplemented with 2 mM glutamine, 10,000 U/ml penicillin, 10 mg/ml streptomycin, 50 µM 2-mercaptoethanol, 1 mM sodium pyruvate, MEM-nonessudinal aminoacids, MEM Vitamin solution, 10% heat-inactivated fetal bovine serum and GM-CSF (20 ng/ml) and IL-4 (40 ng/ml). Fresh medium (3 ml) with GM-CSF (200 ng/ml) and IL-4 (400 ng/ml) was added every 3 days. On day 7, adherent cells, that were harvested using PBS 2 mM EDTA, together with the non-adherent cells were pooled and used as the starting cell source for the experiments.

BMDC Protocol 2

DCs were obtained from the bone marrow of 6 to 8-week-old C57Bl6 mice. Briefly, femora and tibiae from mice were removed and stripped of muscles and tendons; both bone ends were cut and bone marrow was flushed out with RPMI 1640 medium using a 21-gauge needle and syringe. Cell clusters were dissociated by passing through a cell strainer and 0.45 M ammonium chloride was added for red cell lysis. After washing the cell suspension twice in RPMI 1640, $10 \times 10^6$ bone marrow cells per well were cultured in non-treated tissue-culture 6-well plates with 4 ml of complete medium (RPMI 1640 supplemented with 2 mM glutamine, 10,000 U/mL penicillin, 10 mg/mL streptomycin, 50 µM 2-mercaptoethanol, 10% heat-inactivated fetal calf serum with GM-CSF (50 ng/ml). Half of the medium was removed on day 2 and new medium supplemented with GM-CSF (100 ng/ml) and warmed at 37° C. was added. The culture medium was entirely discarded on day 3 and replaced by fresh warmed medium with GM-CSF (50 ng/ml). On day 6, non-adherent cells in the culture supernatant and loosely adherent cells harvested by gentle washing with PBS were pooled and used as the starting cell source for the experiments.

Human Monocyte-Derived Dendritic Cell (mo-DC) In Vitro Differentiation

Peripheral blood mononuclear cells (PBMCs) were isolated by centrifugation over Ficoll-Paque Plus (GE Healthcare). After a 2 h-incubation in plastic 6-well plates, non-adherent cells were removed from culture and adherent cells (monocytes) were cultivated for 7 days in RPMI-1640 culture medium (Gibco, Grand Island, N.Y., USA), supplemented with 10% FCS (Gibco) plus antibiotic-antimycotic (Gibco) and in the presence of GM-CSF (50 ng/ml—Peprotech, Mexico) and IL-4 (50 ng/ml—Peprotech). At day 5 of culture TNF-α (50 ng/ml; Peprotech, Mexico) was added for mo-DC maturation.

Flow Cytometry Analysis

For murine cell analysis, these were stained in ice-cold PBS containing BSA (0.5%) and EDTA (2 mM) using appropriate antibody-fluorophore conjugates. Multiparameter analysis was performed on a BD FACSCanto II analyzer (BD Biosciences) and analyzed with FlowJo software (Tree Star). The following antibodies were used: anti-MHC Class II, anti-CD11c, anti-CD8a, anti-CD3e, anti-CD4, anti-CD86, anti-CD40, anti-CD80, Prior to acquisition, cells were resuspended in PBS/BSA 0.5%/EDTA (2 mM).

Human cells were analyzed in a similar manner, but staining was performed in BSA-PBS, without EDTA. Antibodies against CD11c, CD14, CD80, CD83, CD86, HLA-ABC, HLA-DR, CCR7, PD-L1, conjugated with different fluorochromes and live/dead labeling (Molecular Probes, Oregon, USA) were used. Acquisition was performed in a FACSCanto II analyzer (BD Biosciences) and analyzed with the FlowJo Software X.10.07r2 (Tree Star).

The frequency of FoxP3$^+$ human cells was analyzed using the e-Bioscience Foxp3/Transcription Factor Staining Buffer Set (Affymetrix, e-Bioscience, USA) as described in the manufacturer's protocol. Before intracellular staining, the cells were labeled with fluorescence-labeled anti-CD4, anti-CD8 and anti-CD25 (BD Biosciences).

Cytokines in culture supernatants were determined by Cytometric Bead Array—CBA (BD Biosciences).

Tumor Cell Lysate Preparation

Detached B16F10-Nex2 cells were washed with PBS and resuspended in sterile PBS at a concentration of about $1 \times 10^6$ cells/ml and lysed by 5 cycles of freeze-thawing (liquid nitrogen/90° C.). Cell viability following treatment was assessed using trypan blue exclusion staining. Lysates were used at different concentrations according to the experiment protocol.

Human Lymphocyte Proliferation Assay

Mo-DC were co-cultured with allogeneic lymphocytes (DC:Ly=1:30) to evaluate their ability to induce lymphocyte proliferation. This was measured by carboxyfluorescein succinimidyl ester (CFSE—Molecular Probes) dilution and activation measured by correlation among CD4/CD25 and Foxp3 expression (Clavijo-Salomon et al., 2016).

The examples basically report experiments with synthetic peptides containing sequences of monoclonal antibodies amidated at the C-terminal amino acid against tumor cells. As it will be seen, the in vivo anti-melanoma effects of peptides of the invention in a syngeneic host depend on the immune system, since no protection of the peptide was detected in immune deficient animals.

Flow Cytometry Analysis of Murine T-Regulatory Cells (Treg)

Spleens, lymph nodes and lungs from prophylactic protocol where dendritic cells were stimulated by Rb9 or Rb9+ Lysate, and A1C or A1C+Lysate, and untreated, were removed and macerated before being filtered in a cell strainer. The lungs were incubated with 2 mg/ml of collagenase for 40 min at 37° C. before maceration. The cell suspension was incubated with cold hemolytic buffer for 1 min and then centrifuged. The pellet was suspended with RPMI medium and counted. $1 \times 10^6$ Cells of each group were processed and stained using the Treg Detection Kit (Miltenyi Biotec, Cambridge, USA). Lymphocytes were characterized using anti-CD4 (FITC), anti-CD25 (PE) and anti-Foxp3 (APC). Samples were analyzed by flow cytometry using FACSCantoII (Becton Dickinson, San Jose, Calif., USA). Acquired data were analyzed using the FlowJo V10 (TreeStar Inc., Ashland, Oreg., USA). The percentages of Foxp3$^+$ in CD4$^+$CD25$^+$ lymphocytes are indicated.

Flow Cytometry Analysis of CD4$^+$ and CD8$^+$ Lymphocytes

Lungs from prophylactic protocol stimulated by Rb9 or Rb9+Lysate or A1C or A1C+Lysate or untreated, were removed and incubated with 2 mg/ml of collagenase for 40 min at 37° C. before maceration. The cell suspension was incubated with cold hemolytic buffer for 1 min and then centrifuged. The pellet was suspended with RPMI medium and counted. $1 \times 10^6$ Cells of each group were stained with anti-CD3 (PE) and anti-CD4 (FITC) or anti-CD3 (PE) and anti-CD8 (FITC). All antibodies used were purchase from Miltenyi Biotec, Cambridge, USA. Samples were analyzed by flow cytometry using FACSCantoII (Becton Dickinson, San Jose, Calif., USA). Acquired data were analyzed using the FlowJo V10 (TreeStar Inc., Ashland, Oreg., USA). The percentages of CD4$^+$ or CD8$^+$ in CD3$^+$ lymphocytes are indicated.

Flow Cytometry Analysis of CD74 Receptor in Myeloid Dendritic Cells

The bone marrow derived dendritic cells ($5 \times 10^5$) were incubated with 50 µg of Rb9 for 48 h. After incubation the cells were stimulated with or without LPS (Sigma-Aldrich, Missouri, USA), at 200 ng/ml or tumor lysate (B16F10-Next cells) in the proportion of 30 DCs to 1 tumor cell, for 24 h. After incubation, the cells were harvested and stained with anti-CD74 (BV786) from BD Bioscience. Stained cells were acquired using LSRFortessa™ (Becton Dickinson, San Jose, Calif., USA) and data analysis was performed using the FlowJo V10 (TreeStar Inc., Ashland, Oreg., USA). The results are represented as percentage of $CD74^+$ cells in $CD11b^+CD11c^+$ or $CD11c^+MHCII^+$ population.

Syngeneic Metastatic Melanoma Model and the Assay of Rb9-Scrambled Peptides 6 to 8 Week-old C57BL/6 mice (n=5, per group) were intravenously challenged with $1 \times 10^5$ of syngeneic B16F10-Nex2 viable cells in 0.1 mL of RPMI medium without FBS, and treated on the next day with intraperitoneal doses of 300 μg (10 mg/kg) each, of Scr1, Scr2, Scr3 or Scr4 peptide or with the control vehicle (PBS) in alternate days, total of 5 doses. After 14 days, mice were euthanized, and lungs were harvested and assessed for metastatic colonization. The number of metastatic lesions was quantified using a stereo microscope (Nikon, Tokyo). The percentage of the tumor area/total area was also quantified by ImageJ software.

Protein Extraction and Western Blotting

Myeloid DCs were serum starved for 24 h, pre-treated (or not) with Rb9 at 200 μM concentration for 6 h and stimulated with recombinant mouse MIF (1 μg/mL) at 2, 5, 10 or 20 minutes for determination of AKT, ERK1/2, IKKα/β, and IkBα phosphorylation. Protein lysates were separated by electrophoresis, and immunoblotting analyses were performed for: total AKT, total p44/42 MAPK (ERK1/2), total IKKα, total IkBα, total NF-kB p65, phospho-AKT (Ser473), phospho-ERK1/2 (Thr202/Tyr204), phospho-IKKα/β (Ser176/180), phospho-IkBα (Ser32) and phospho-NFkB p65 (Ser536). GAPDH was assayed for loading control. HRP-conjugated secondary antibodies were used, followed by incubation with the ECL substrate (Millipore, Billerica, Mass.). All primary and secondary antibodies were purchased from Cell Signaling Technologies (Beverly, Mass., USA). Anti-CD74 receptor was also assayed (Abcam, Cambridge, UK). Phosphorylation ratios were quantified using ImageJ software. Results are represented in arbitrary units normalized to untreated control lanes. Signal intensity ratios of phosphorylation are also demonstrated in arbitrary units normalized to total lanes.

Chemiluminescent Dot-Blotting

Interaction of the Rb9 peptide and recombinant mouse CD74 or recombinant mouse MIF was determined by chemiluminescent dot-blotting. The amount of 25 nmol of each peptide: Rb9, Rb10A1, C36L1, WTzn, INKKI, P5 or the irrelevant CDR peptide control (iCDR) and vehicle (0.025% DMSO in dH2O) were immobilized on nitrocellulose membranes, blocked with 5% BSA in PBS-Tween 0.05% and incubated with 25 nM of recombinant CD74 (Abcam, Cambrigde, UK) or recombinant MIF (R&D Systems, Minneapolis, USA) overnight at 4° C. Membranes were washed and incubated with primary mouse anti-CD74 or anti-MIF (both from Abcam, Cambridge, UK), washed and incubated with secondary anti-mouse IgG-HRP. Immunoreactivity was determined using the ECL Western Blotting Substrate (Millipore, Billerica, Mass.), and signal was detected in a trans-illuminator Uvitec, Cambridge, UK).

Using the same assay we compared the interaction of the peptides Rb9, Rb10A1, Rb9-MID and vehicle (1% DMSO in $dH_2O$) and recombinant mouse MIF with some modifications. 100 μg of the peptides were dotted on nitrocellulose membranes, blocked and incubated with 50 nM of rMIF (Abcam, Cambridge, UK) overnight at 4° C. Membranes were washed and incubated with primary mouse anti-MIF (R&D, Minneapolis, USA) overnight at 4° C., washed and incubated with the secondary anti-goat IgG-HRP (Sigma-Aldrich, Missouri, USA). The reaction was detected as described above. Graphs represent RLU in dot area quantified using ImageJ software.

Example 1

Rb9 at 250 μg i.p. dose, was administered on days 1, 3, 5, 7, 9, 11 after tumor cell challenge in immunocompetent C57B16 mice as well as in immunodeficient NOD/Scid/IL-2R-gamma$^{null}$ mice. B16F10-Nex2 tumor cells ($2 \times 10^5$) in RPMI (100 μl) were injected in both animal groups in the tail veins on day 0. Animals were sacrificed on day 22, or 10 days after the last administration of the peptide, and their lungs were examined for dark melanotic nodules. In the immunocompetent mice, Rb9 was clearly protective significantly reducing the number of tumor cell nodules. No protection was seen in the immunodeficient animals (FIG. 1), indicating that the protective activity of Rb9 in vivo depends on the immune response. As determined before (U.S. Pat. No. 9,193,797 B2), Rb9, the $V_H$ CDR3 (H3) of RebMab200 but not the other 5 CDRs of this monoclonal antibody displayed this in vivo protection against metastatic melanoma.

B16F10-Nex2 melanoma model was also used to test other mAb CDRs. MAb C7 H2 (Arruda et al., 2012; Massaoka et al., 2013) and C36 L1 (Figueiredo et al., 2015) CDR peptides were protective against metastatic melanoma, although their antitumor cytotoxicity in vitro involved different targets and mechanisms of action.

Figure 2:
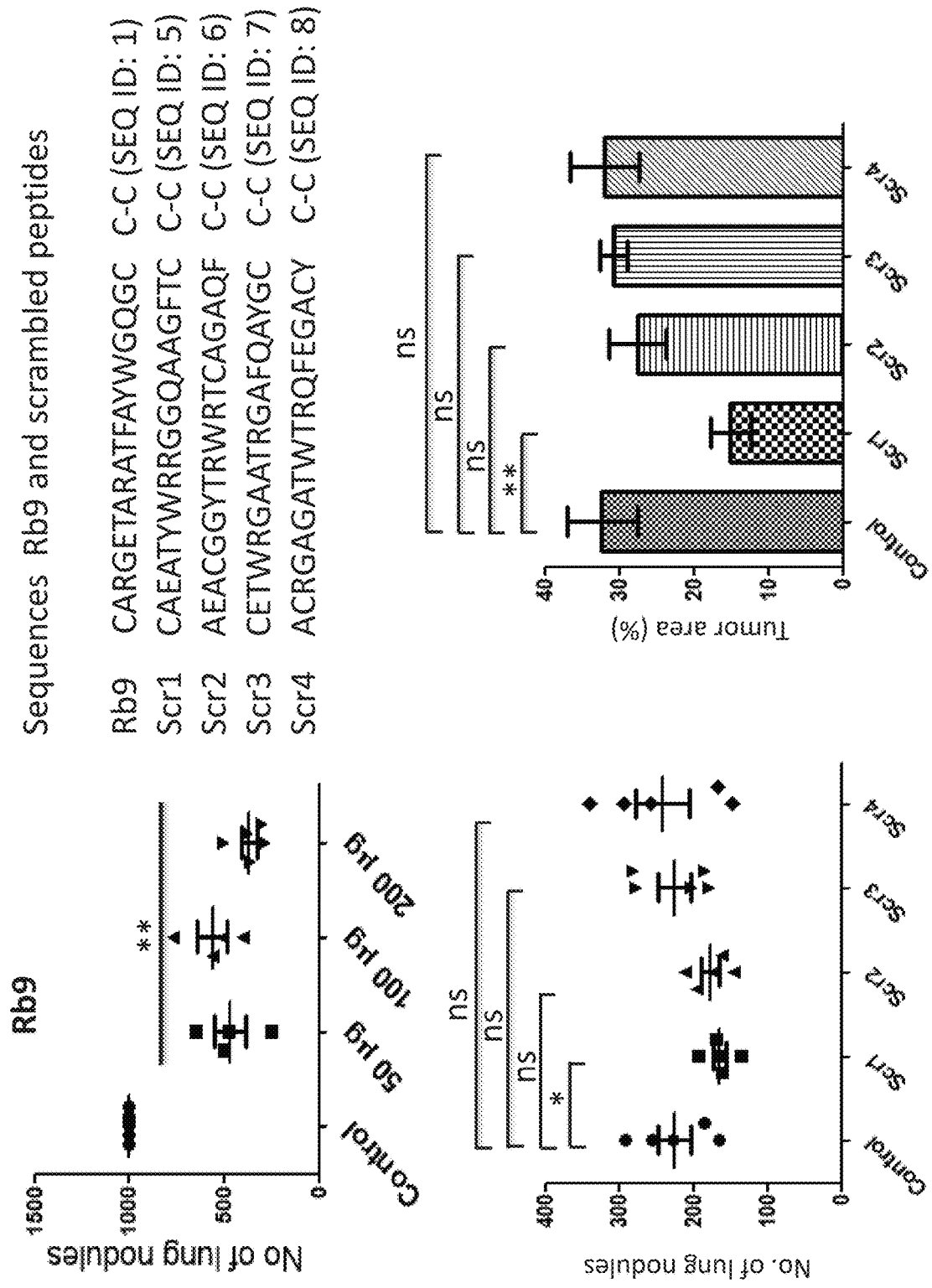
FIG. 2 shows that the metastatic melanoma model i.p. doses of Rb9 in the 50 to 200 μg range are effective for protection.

Rb9 best concentrations for protection against B16F10-Nex2 melanoma in the metastatic model, were in the 200-300 μg dose range per animal, probably because of in vivo clearance as by renal filtration and proteolytic degradation. In the metastatic model, however, significant protection was also obtained with 50-100 μg i.p. doses (FIG. 2). Subcutaneous growing melanoma was much more resistant to Rb9 i.p administration.

Scramble (Scr) peptides were also synthesized to be used as controls and to examine the specificity of the sequence maintaining the disulfide structure in all of them. Out of five Scr cyclic peptides only Scr 1 showed an activity similar to Rb9. Scr peptide 3 was regarded as a good negative control for in vivo experiments with metastatic melanoma.

Figure 3:
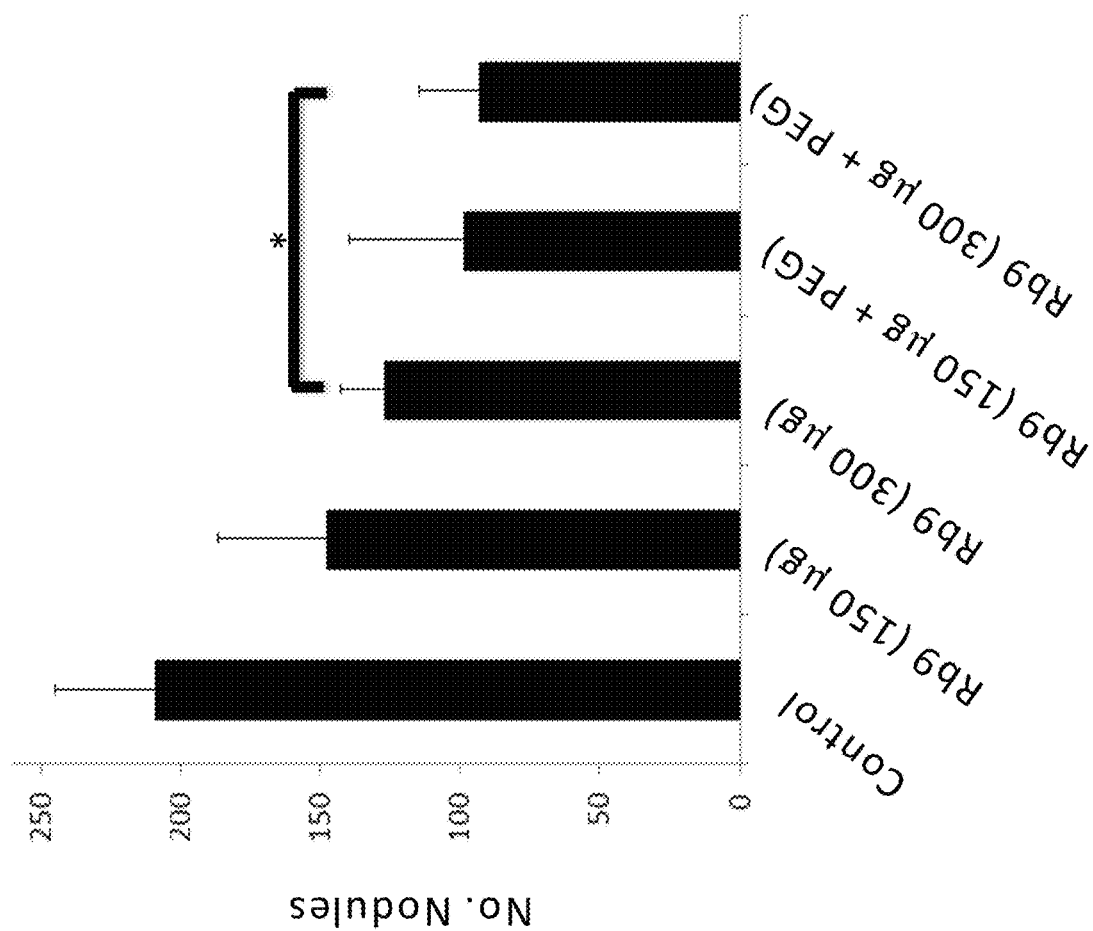
FIG. 3 shows that the coupling of Rb9 with PEG increased the peptide antitumor activity in the metastatic melanoma model.

The efficacy of Rb9 in the metastatic melanoma treatment was improved by peptide PEGylation even with PEG2000 (FIG. 3). C57B16 mice were intravenously challenged with $4 \times 10^5$ syngeneic B16F10-Nex2 cells in 0.1 ml of RPMI without FBS. Animals challenged with tumor cells were treated on the next day with 5 i.p doses of 150 and 300 μg of Rb9 or the same peptide molar dose bound to PEG2000, MW 3910.5.

Concerning the Rb9 doses used for the observed effects, as shown before (U.S. Pat. No. 9,193,797 B2), mice injected with RB9 for seven consecutive days (300 μg via i.p.) showed no signs of toxicity or histological alterations in the liver, lung, heart, kidney and spleen. Also, the peptides were not hemolytic.

Example 2

Figure 4:
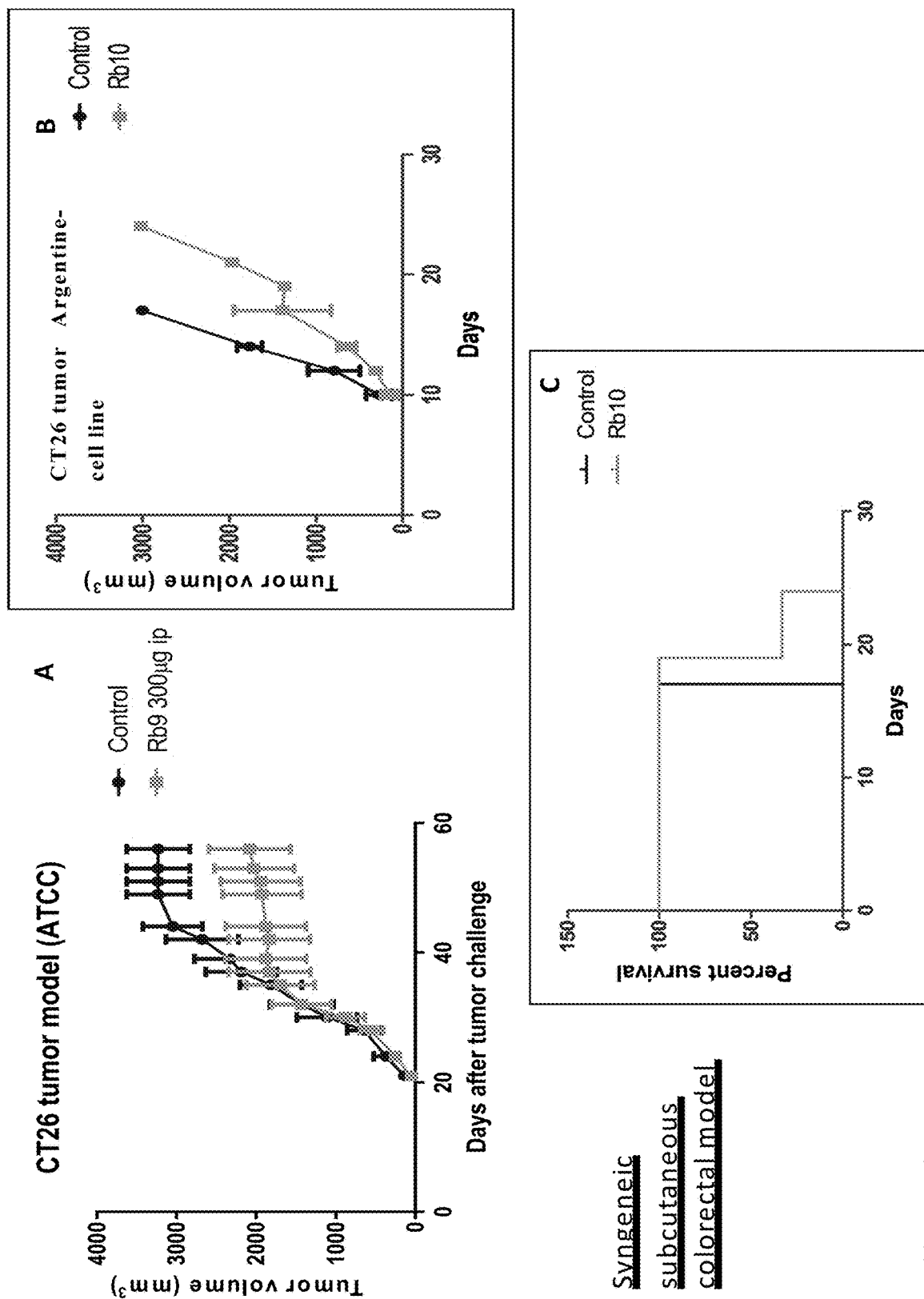
FIG. 4 shows that the antitumor activity of Rb9 using the subcutaneous route was seen in a syngeneic colorectal tumor model.

Rb9 at 300 μg i.p. significantly delayed the subcutaneous growth of colorectal CT26 carcinoma cells of moderate virulence (ATCC, CRL-2638) in syngeneic Balb/c mice. Administration of the peptide was carried out in 5 consecutive days initiating one day after tumor challenge. Rb10 also delayed s.c. CT26 cells of high virulence (Argentina cell line), prolonging the survival time of $H-2^d$ syngeneic animals (FIG. 4). Administration of the peptide was performed in 5 alternate days initiating one day after tumor challenge.

Figure 5:
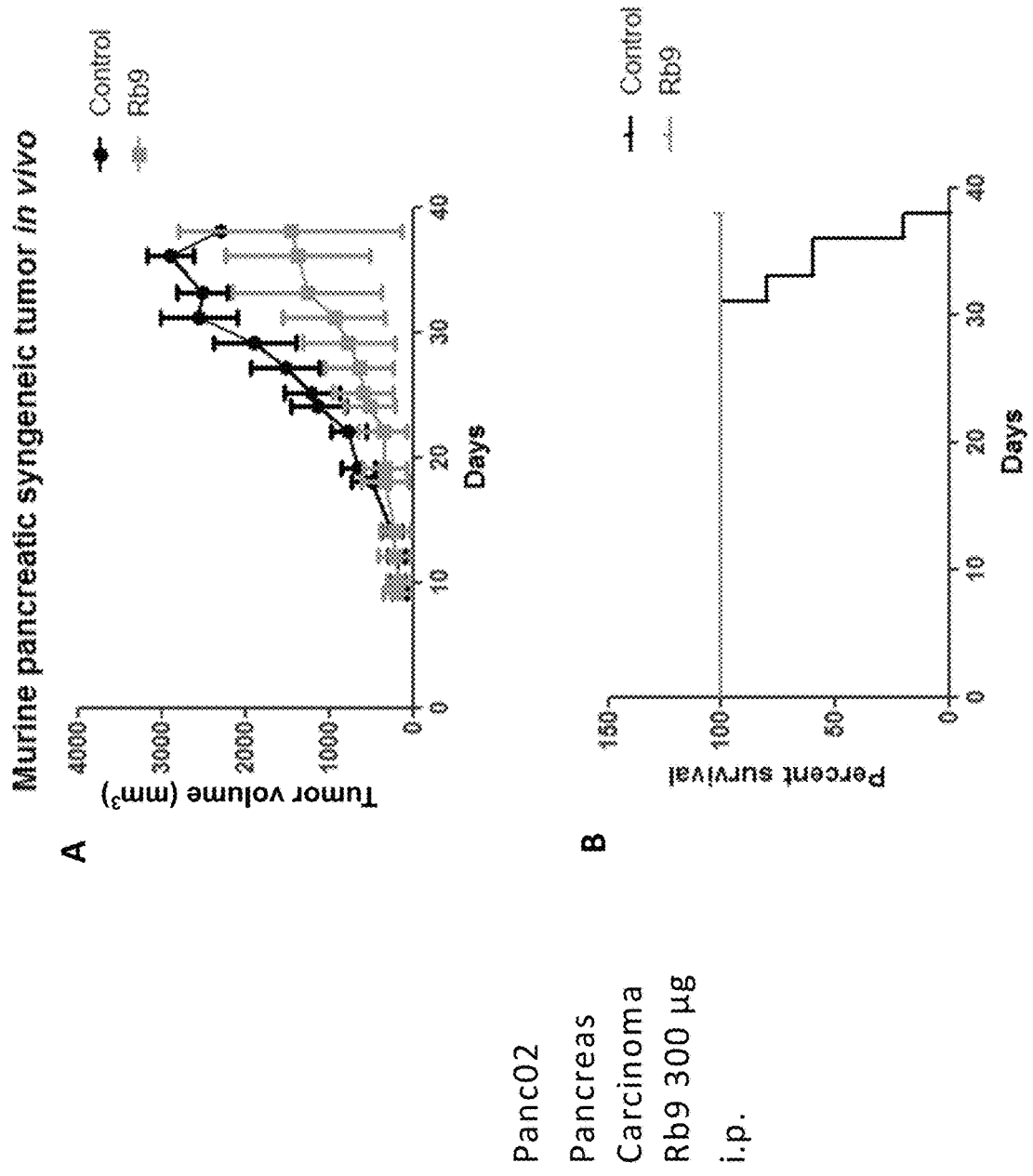
FIG. 5 shows that the antitumor activity of Rb9 using the subcutaneous route was seen in a syngeneic pancreatic carcinoma model.

Another syngeneic tumor cell line tested was the pancreas carcinoma Panc02. Rb9 also at 300 µg i.p. significantly delayed the s.c. tumor growth. The administration of the peptide began on day 1 (1 day after tumor challenge) for a total of 5 doses given every other day. Unlike the untreated control, no deaths were recorded in Rb9 treated syngeneic animals up to the 40th day (FIG. 5). It is noticeable that while CT26 and Panc02 s.c. tumors were inhibited by Rb9 administered i.p., B16F10-Nex2 melanoma was resistant. The different accessibility of immune cells activated by Rb9 is suggested to explain these effects on different s.c. tumors.

These results, showing significant antitumor protection by Rb9 administered i.p and s.c in syngeneic animals, raises the question of Rb9 mechanism of action in vivo, which depends on the immune system. Indeed, the direct Rb9 and Rb10 activities on melanoma cells in vitro (Girola et al., 2016), which require tumor cell receptors, differ from the in vivo protective effects observed against 3 syngeneic tumors.

Example 3

Protective effects of Rb9 and Rb10 in vivo against syngeneic tumors were attributed to stimulation of the immune system. Therefore, a prophylactic treatment with syngeneic dendritic cells (DCs) stimulated ex vivo by the peptide was tested to prove this point. Bone marrow DCs obtained as in Protocol 1 (Material and Methods) at a density of $5 \times 10^5$ cells per well of a 6-well culture plate were incubated with 50 µg/ml of Rb9 (SEQ 1D) or Rb10A1 (SEQ 4D) alone or followed by B16F10-Nex2 ($5 \times 10^4$) cell lysate treatment, during 24 h. DCs were inoculated s.c. in syngeneic mice. On day 14, mice were inoculated i.v. with melanoma tumor cells ($5 \times 10^5$ cells) and on day 29, the lung melanotic nodules were counted.

A remarkable protective effect was observed with DCs stimulated by Rb9 with or without tumor cell lysate (FIG. 6A). The Rb10A1 in which the N-terminal Cys was replaced by alanine (A1C), used as negative control in in vitro experiments, was also protective against melanoma in the metastatic model but less effectively than Rb9. The protective effect of DCs stimulated by Rb9 and primed with tumor antigens (lysate) strongly suggests that this is the predominant in vivo mechanism of peptide Rb9 stimulation of the immune system. The peptide administered i.p, s.c., i.d, will immediately interact with dendritic cells that can be activated or immunomodulated to lead a specific type of immune response. Activated DCs, primed with tumor antigens will migrate to lymph nodes to induce a specific immune response.

Therapeutic treatment with syngeneic dendritic cells (DCs) stimulated ex vivo with 50 µg/ml of Rb9 or Rb10A1 (A1C) alone, is also shown in FIG. 6B. DCs were inoculated s.c. in syngeneic mice, 8 days after the melanoma tumor cell challenge. The B16F10-Nex2 cell lysate was not used to prime DCs in this assay to avoid excess tumor antigen derived from tumor cell lysis in vivo, and a tolerogenic response. Lung nodules of melanoma cells injected i.v. and formed after 7 days and after 12 days, from 3 independent experiments were combined to represent colonization clusters for comparison with the therapeutic experiment of FIG. 6C.

Figure 7:
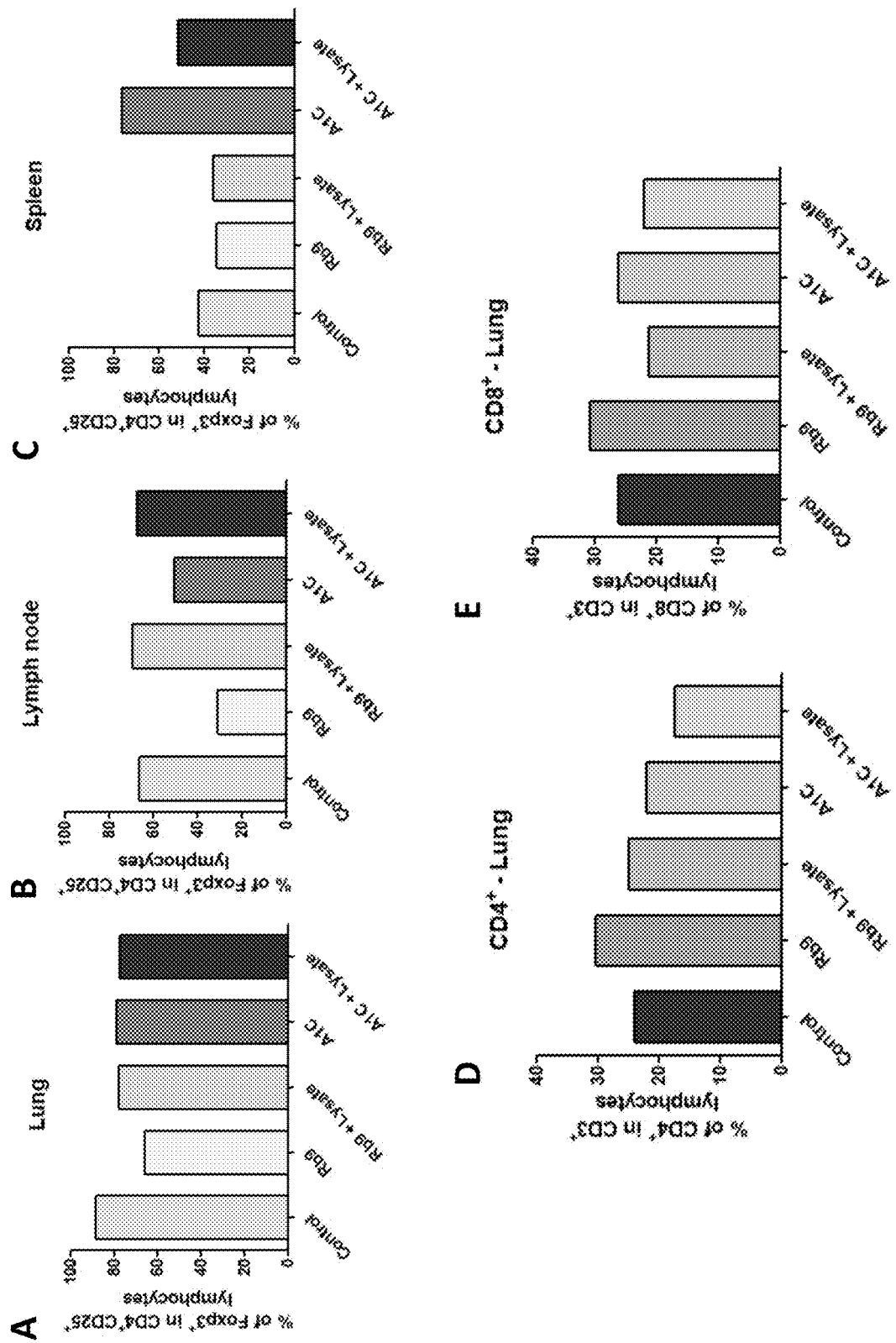
FIG. 7 shows that in the previous prophylactic protocol, protective against metastatic melanoma, Rb9 reduced the number of FoxP3+ Tregs and stimulated effective T-CD4+ and T-CD8+ immune response.

In the prophylactic protocol the protective effect of Rb9-stimulated DCs could be attributed partially to reduced Tregs and increased T-CD4+ and T-CD8+ effector cells (FIG. 7).

Figure 8:
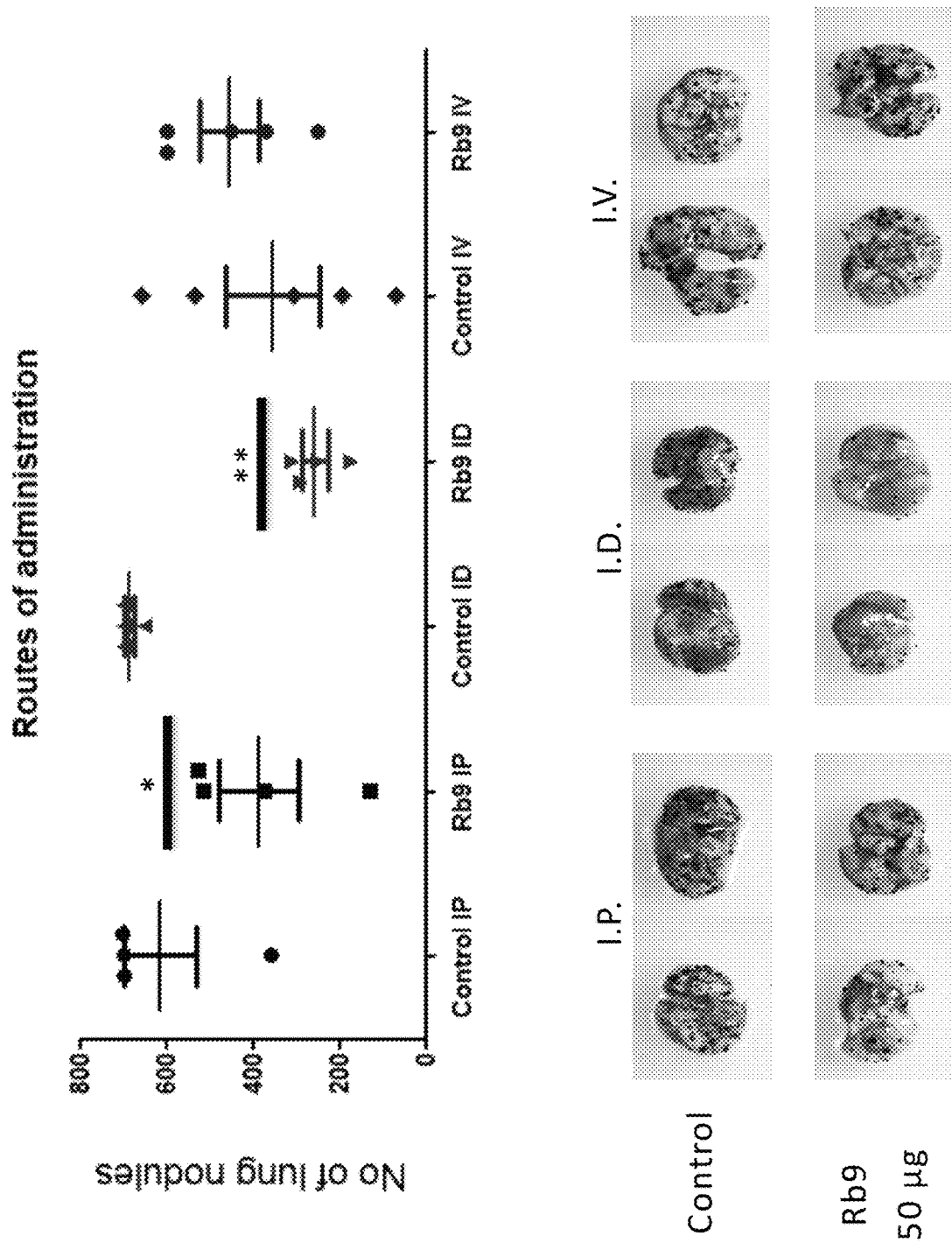
FIG. 8 shows that, in a metastatic melanoma model, the i.d. (intra-dermal) route was mostly efficient in the administration of Rb9 for antitumor protection.

In an experiment comparing i.p, i.d. and i.v. peptide administration, the i.d. (or s.c. in the mouse), gave the best result in the melanoma metastatic model (FIG. 8).

Example 4

Rb9 is incorporated in DCs ex vivo leading to a functional protective response. Such incorporation was also seen using confocal microscopy. A biotinyl derivative of Rb9, biotin-AGG-Rb9 was incubated with DCs (Protocol 1, Materials and Methods) as follows: Bone marrow DCs, 7-day differentiation in R10 medium (DMEM supplemented with 10% FBS, sodium pyruvate 100 mM, MEM-nonessential amino acids 100×, glutamine 200 mM, MEM vitamin solution 100×, (β-mercaptoethanol 0.05 M, 10.000 U penicillin, streptomycin 10 mg/mL, GMCSF 20 ng/mL and 20 ng/ml), were centrifuged and suspended in fresh R10 medium. Cells were distributed on glass slides inside a 24-well culture plate at 25,000 cells/60 µL density. Fresh R10 medium (300 µl) was added per well of adhered cells and the plates were incubated at 37° C. with 5% $CO_2$ overnight. Cells were then incubated with biotinylated Rb9 at 0.5 mM for 1, 3, 8 and 24 h. A negative control had cells and no peptides. The culture medium was removed, cells were washed in PBS, were fixed in formaldehyde, washed and permeabilized with 0.01% Triton100. Cells were stained with phalloidin-rhodamine 1000×, anti-biotin-FITC 250×, and DAPI 100× for 1 h, washed with PBS, and glass slides prepared and covered using Vectashield. They were examined in a confocal microscope.

Figure 9:
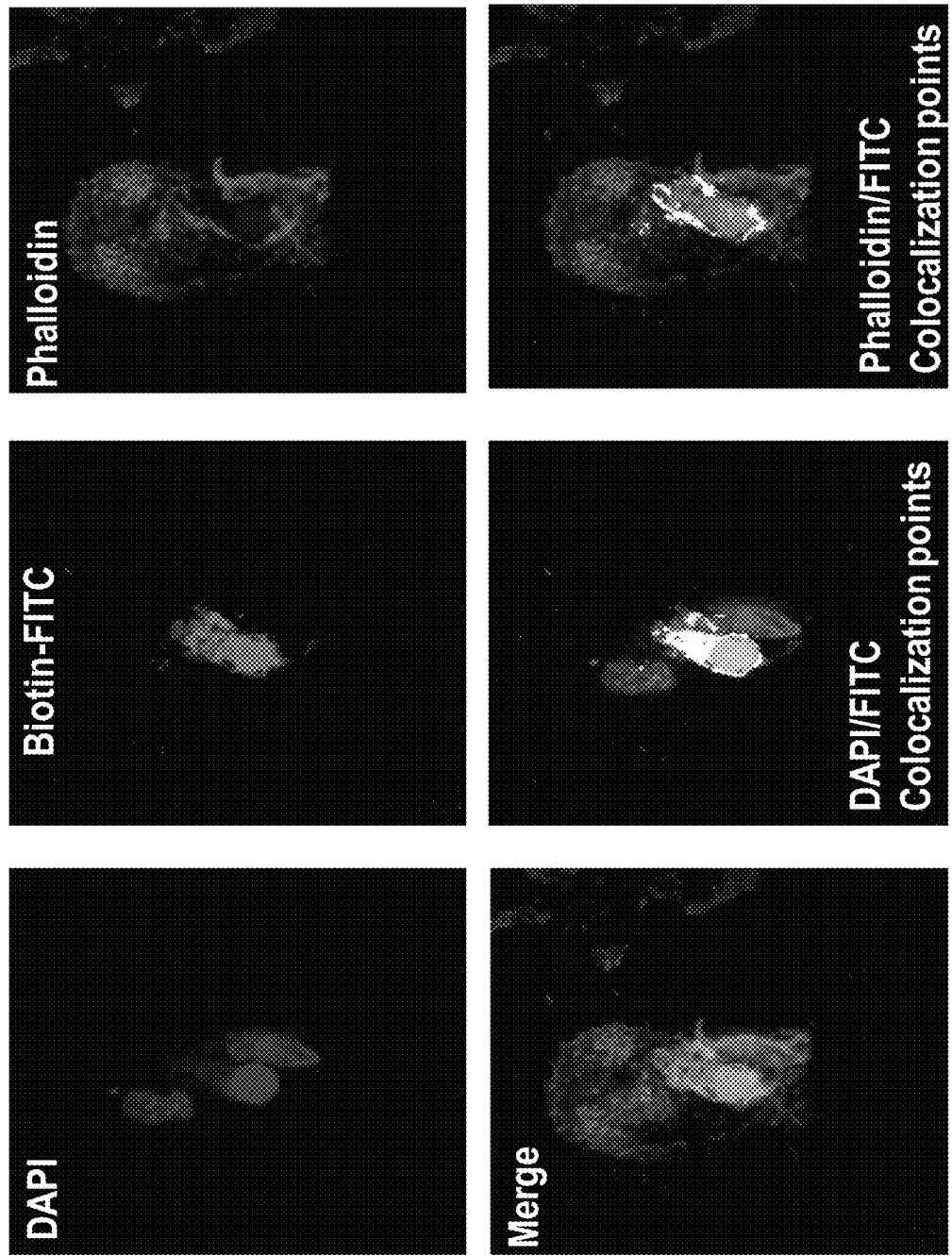
FIG. 9 shows that biotinylated Rb9 labeled with FITC penetrates dendritic cells and migrates to the nucleus where it colocalizes with DAPI. Some co-localization with phalloidin is also seen.

Biotinylated Rb9 penetrated DCs, probably by endosomes, and interacted with F-actin. The peptide was then transferred to the nucleus where colocalization points with DAPI/FITC were seen (FIG. 9). Colocalization with phalloidin was also seen but not extensive. The fact the Rb9 tends to migrate to the nuclei of DCs suggests that it may act as a signaling mediator.

Example 5

Figure 10:
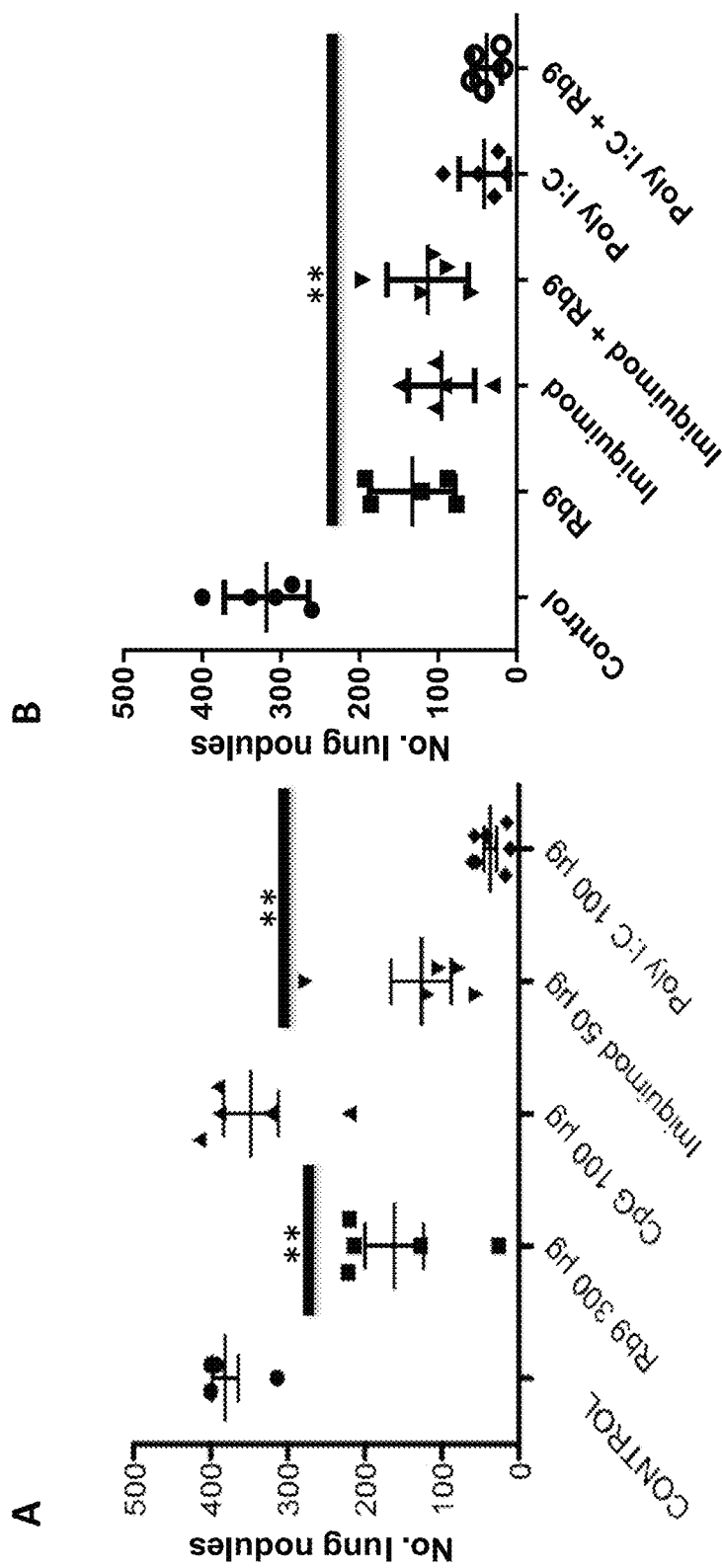
FIG. 10 shows that Rb9 is as protective in the metastatic melanoma model as imiquimod. It seems to co-stimulate the immune system with Poly-I:C

A functional comparison of the protective effects of Rb9 and the well-established Toll-R agonists was made using the metastatic melanoma model. Mice were injected with $5 \times 10^5$ B16F10-Nex2 cells i.v. suspended in 100 µl PBS. Rb9 at 300 µg/100 µl injected i.p. in 5 consecutive days, one day after tumor cell challenge. Imiquimod at 50 µg/100 µl was injected i.p. in 3 alternate days; CpG ODN 1585, i.p., in two alternate days; and Poly (I:C), i.p., in two alternate days. After 15 days of tumor challenge, the animals were sacrificed, the lungs were removed and the pulmonary nodules were counted. Antitumor activities of Rb9 and Imiquimod were the same but were not additive. CPG was not protective and Poly I:C was strongly active alone or combined with Rb9 (FIG. 10)

Example 6

Cytokine production under conditions of metastatic tumor growth and Rb9 administration was examined in splenocytes of syngeneic animals.

Figure 11:
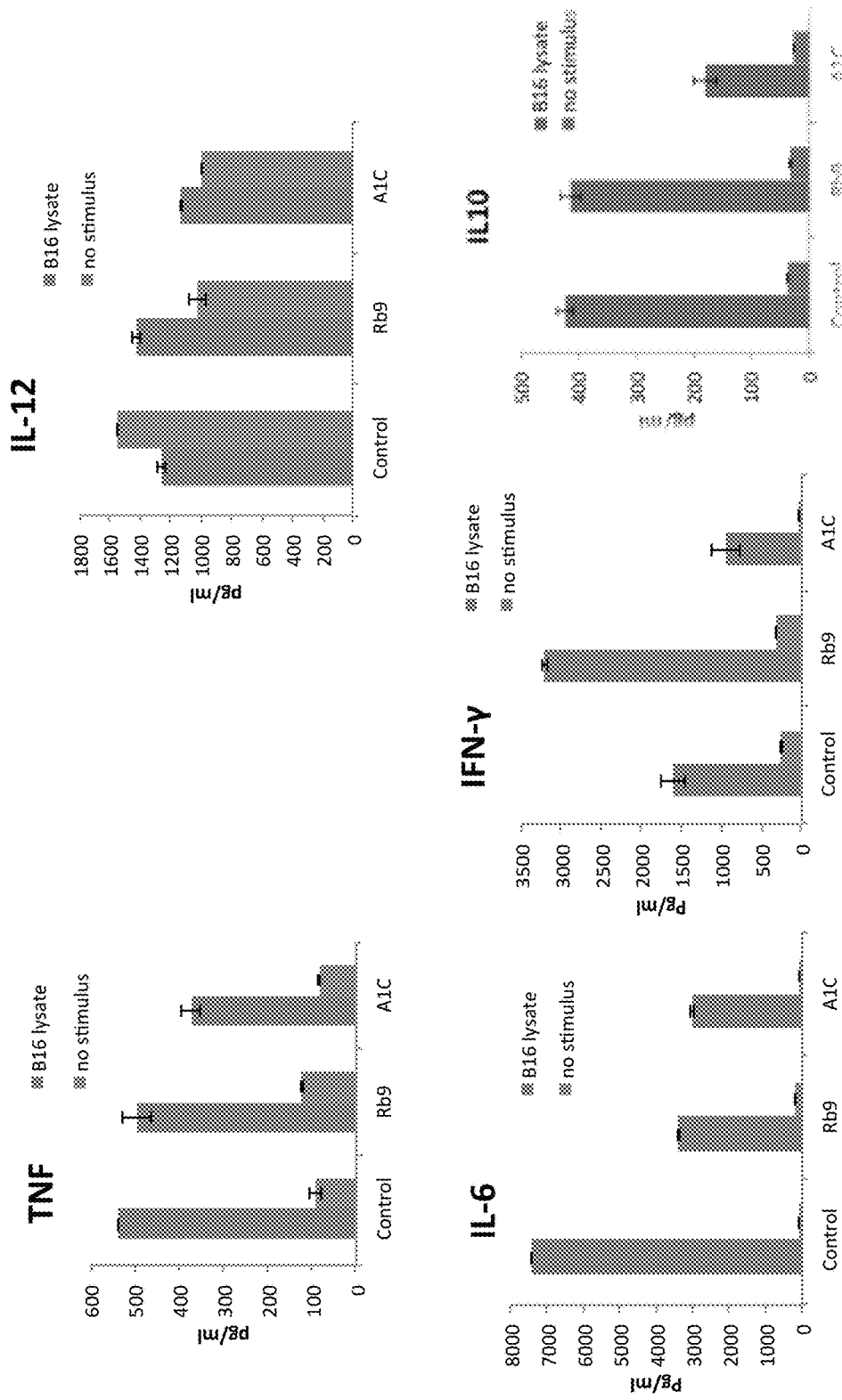
FIG. 11 shows that, in tumor bearing syngeneic animals, administration of Rb9 together with melanoma antigens stimulated IFN-gamma in splenocytes, significantly reduced IL-6 and showed no effect in TNF-alpha, and IL-10 expression. A slight stimulation of IL-12 was seen.

Mice were challenged with $5 \times 10^5$ B16F10-Nex2 cells via the i.v. route. Animals were separated in 3 groups: Control (without peptide administration), Rb9 and Rb10A1 (negative control peptide from in vitro experiments). Peptides at 300 µg solubilized in 10 µl distilled $H_2O$ and 90 µl of PBS were injected via i.p. route per animal, for 5 consecutive days initiating one day after tumor cell challenge. Seventeen days after tumor challenge mice were sacrificed and spleens were removed. Splenocytes after incubation in hemolysis buffer were suspended in R10 medium and plated in 6-well plates and $10^6$ cells/well. Cells were incubated for 72 h with or without tumor cell lysate (from $10^5$ B16F10-Nex2 cells) in triplicate. The supernatants were collected, and cytokines measured by ELISA (FIG. 11).

In most cases, except for IL-12, splenocyte cytokine readings were significant only in presence of tumor cell lysate. No stimulus was necessary in the case of IL-12 production, which was comparable in the three groups. Rb9 increased IFN-gamma and decreased IL-6 in relation to the untreated control and showed no effect in the production of TNF-alpha and IL-10. Generally, Rb10A1 downregulated cytokine production in splenocytes.

In these cells stimulated by tumor lysate, melanoma growth and Rb9 administration favored a Th-1 response that could contribute to the antitumor phenotype.

Example 7

Rb9 immunomodulated splenocytes to express certain cytokines; it also stimulated dendritic cells to express co-stimulatory molecules and strongly induced the proliferation of T-CD8+ cells in lymph nodes regional to lung metastatic melanoma. To approach the TGF-beta production by Rb9 stimulated DCs from lymphoid organs in the metastatic melanoma set up, $5\times10^5$ B16F10-Nex2 cells were injected i.v. in C57Bl6 syngeneic mice, and Rb9 and Rb10A1 i.p. treatment (300 μg/dose) was administered during consecutive days beginning one day after tumor cell challenge. Animals were sacrificed on day 17 and their lungs, cervical and axillary lymph nodes and spleen were processed for examination. Lymph nodes and spleen were macerated separately, DMEM was added and passed through a cell strainer. CD11c+ cells were isolated using mouse CD11c+ beads and magnetic sorting. Cells were suspended in R10 medium and plated in 95-well plates at $10^6$ cells/well. Cells were incubated for 24 h with or without tumor cell lysate (B16F10 stimulus). The supernatant was used in a TGF-beta1 ELISA test.

Figure 12:
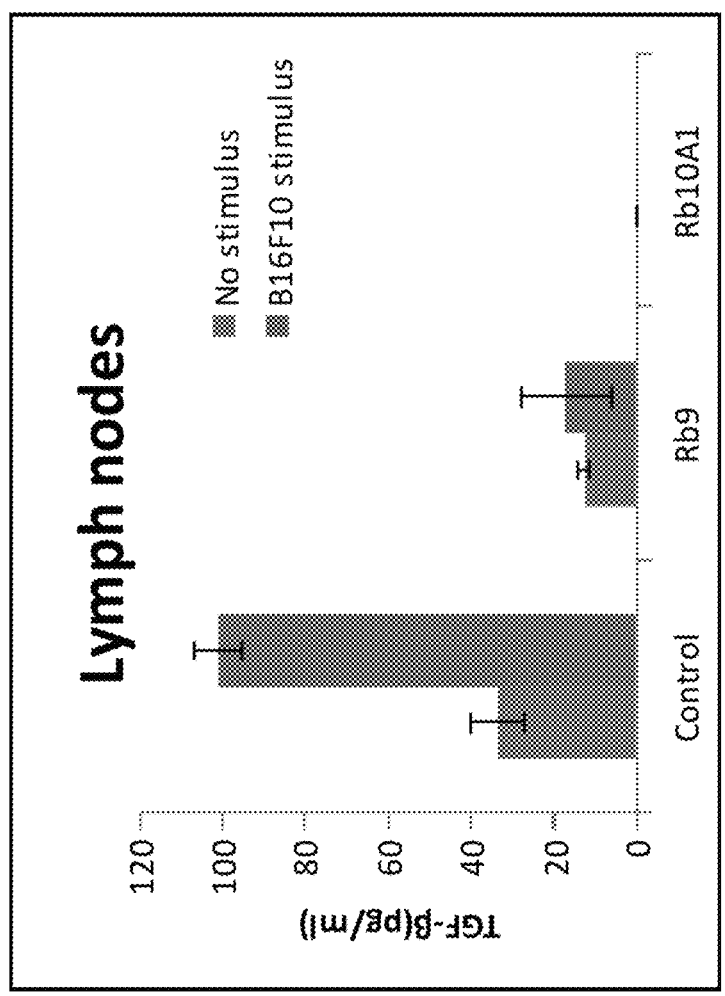
FIG. 12 shows that, in the same system as of FIG. 12, administration of Rb9 most significantly inhibited the expression of TGF-beta in the lymph nodes.

Rb9 treatment increased TGF-beta in the tumor-lysate stimulated CD11c+ cells from the spleen, whereas Rb10A1 treatment markedly inhibited this response. In contrast, Rb9 greatly reduced TGF-beta secreted by the lymph node CD11c+ cells in comparison with the vehicle (PBS) control cells stimulated by melanoma lysate (FIG. 12). Rb10A1 fully inhibited TGF-beta production.

Since both T-effector cells and Treg can proliferate when activated in the lymph nodes, Rb9 inhibition of TGF-beta production is an indication that Treg is not induced in this system that showed high percentage of T-CD8+ cells.

Example 8

Rb9 has shown anti-tumor properties using a syngeneic melanoma model. The protective activity of Rb9 in vivo has been attributed to peptide stimulation of DCs that became active inducers of a T-CD8+ rich immune response. Activation by Rb9 of B cells generating anti-tumor antibodies has also been investigated in a metastatic melanoma set up.

Figure 13:
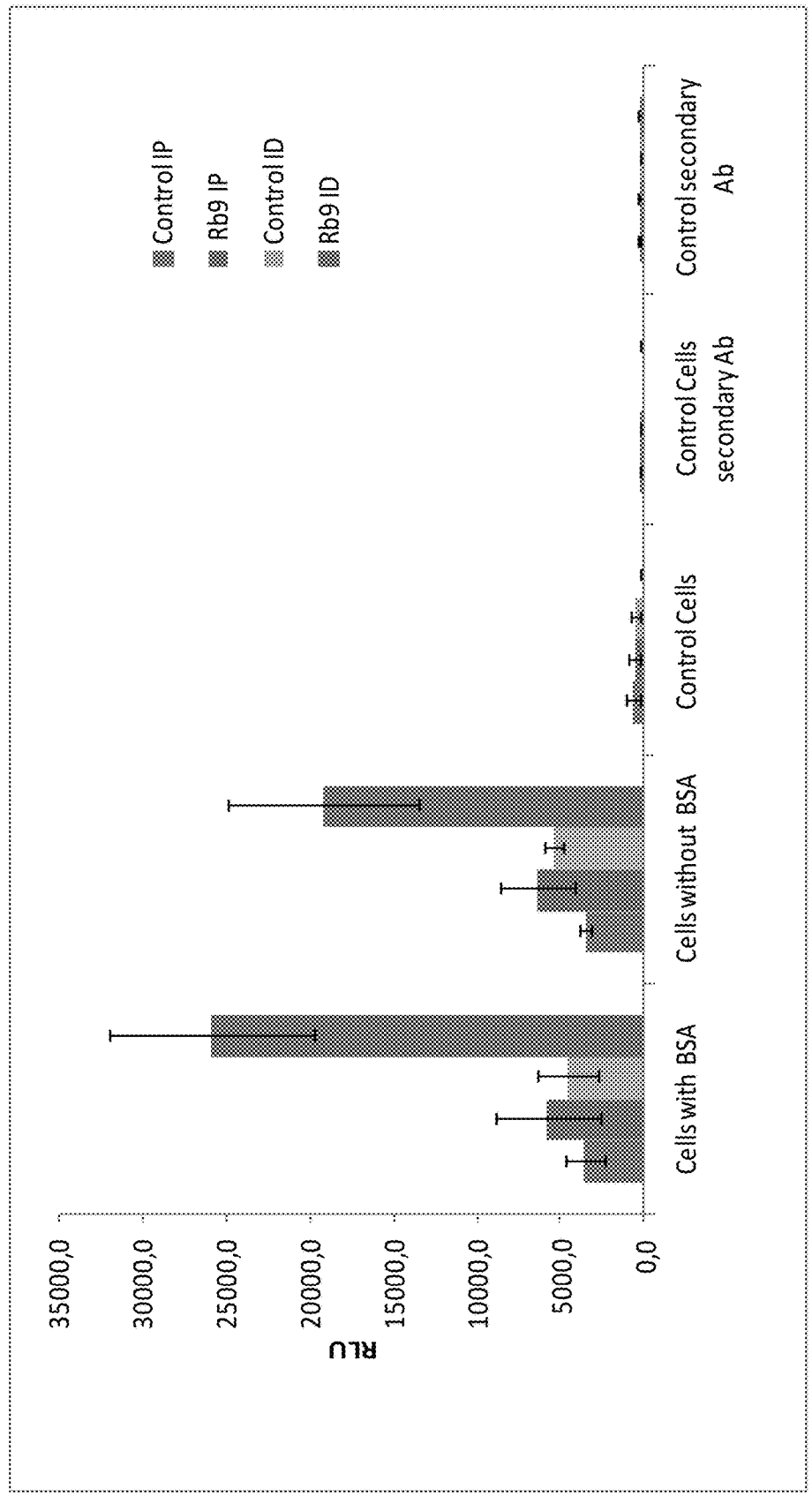
FIG. 13 shows that Rb9 administered through i.d. route acted as an efficient adjuvant for the production of antibodies reacting with B16F10-Nex2 melanoma cells.

Sera from animals developing metastatic melanoma and treated with Rb9 administered i.p. or i.d. were collected and tested against B16F10-Nex2 cells plated on 96-well plates at a density of $2.5\times10^4$ cells per well. As titrated before, the best response was achieved with 1/5 diluted sera. Under these conditions, melanoma cells with or without BSA, reacted with antibodies raised in syngeneic mice with metastatic melanoma that have been treated with Rb9. With both BSA treated or untreated tumor cells sera from animals injected intradermally with Rb9 reacted best with B16F10-Nex2 cells 4-5 times more than Rb9 administered i.p. Clearly Rb9 via i.d. route stimulated a B cell response inducing anti-melanoma antibodies that could increase the protection against metastatic melanoma (FIG. 13).

Example 9

The core sequence of Rb9 (SEQ ID: 1) seems to be the Rb9-MID sequence [RATFAYWG] (SEQ ID: 2). In fact, in CD11c+, MHC II+ bone marrow DCs obtained by Protocol 2, Rb9-MID was compared to Rb9 in the immunomodulation of a few markers with or without Poly I:C (Poly in FIG. 14).

DCs were treated with 100 μg/ml Rb9, 100 μg/ml Rb9-M, 12.5 μg/ml Poly I:C and Poly IC+Rb9 or Rb9-MID during 60 h. DCs were centrifuged and washed once with MACS buffer. Cells ($10^6$) were resuspended in 45 μl of buffer and 5 μl of antibodies/fluorophore, CD11c APC, MHC II PE, CD80 FITC, CD86 VioBlue and CD40 PE. The samples were acquired in BD FACS Canto II using the FacsDiva software. The data were analyzed by using the FlowJo software.

Figure 14:
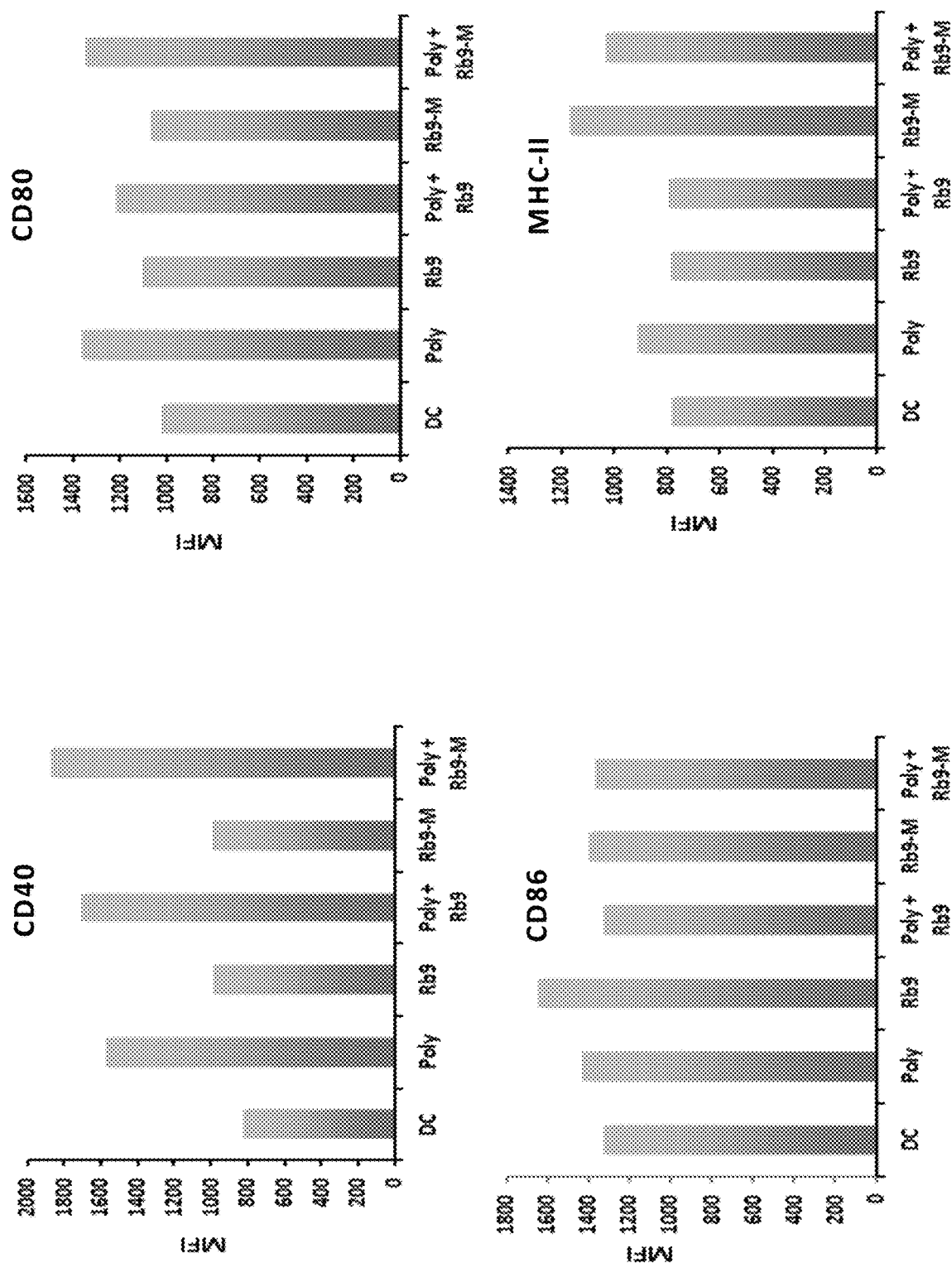
FIG. 14 shows that Rb9-MID (SEQ ID: 2) is a core sequence of Rb9 rendering immunomodulatory effects on bone marrow DCs.

Rb9-MID stimulated CD40 over Poly I:C much like Rb9. Effects of both peptides on the expression of CD80 were similar. Rb9 but not Rb9-MID stimulated CD86 over Poly I:C, and Rb9-MID significantly increased the expression of MHC II over Poly I:C and Rb9. It is possible then that Rb9-MID may render different derivatives for an effective immunomodulatory effect (FIG. 14).

Example 10

Figure 15:
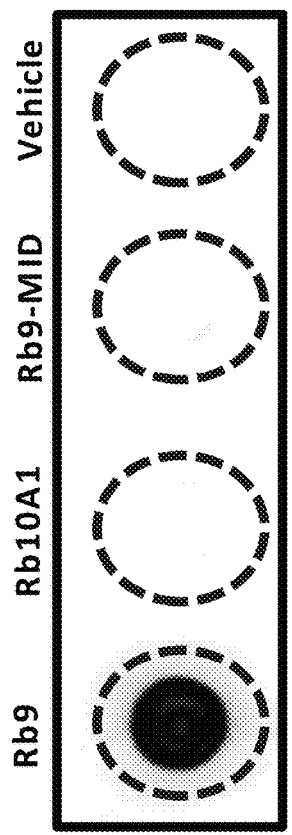
FIG. 15 shows the reactivity by dot blotting of Rb9 (but not Rb10A1 or Rb-MID) with recombinant MIF.
Figure 15:
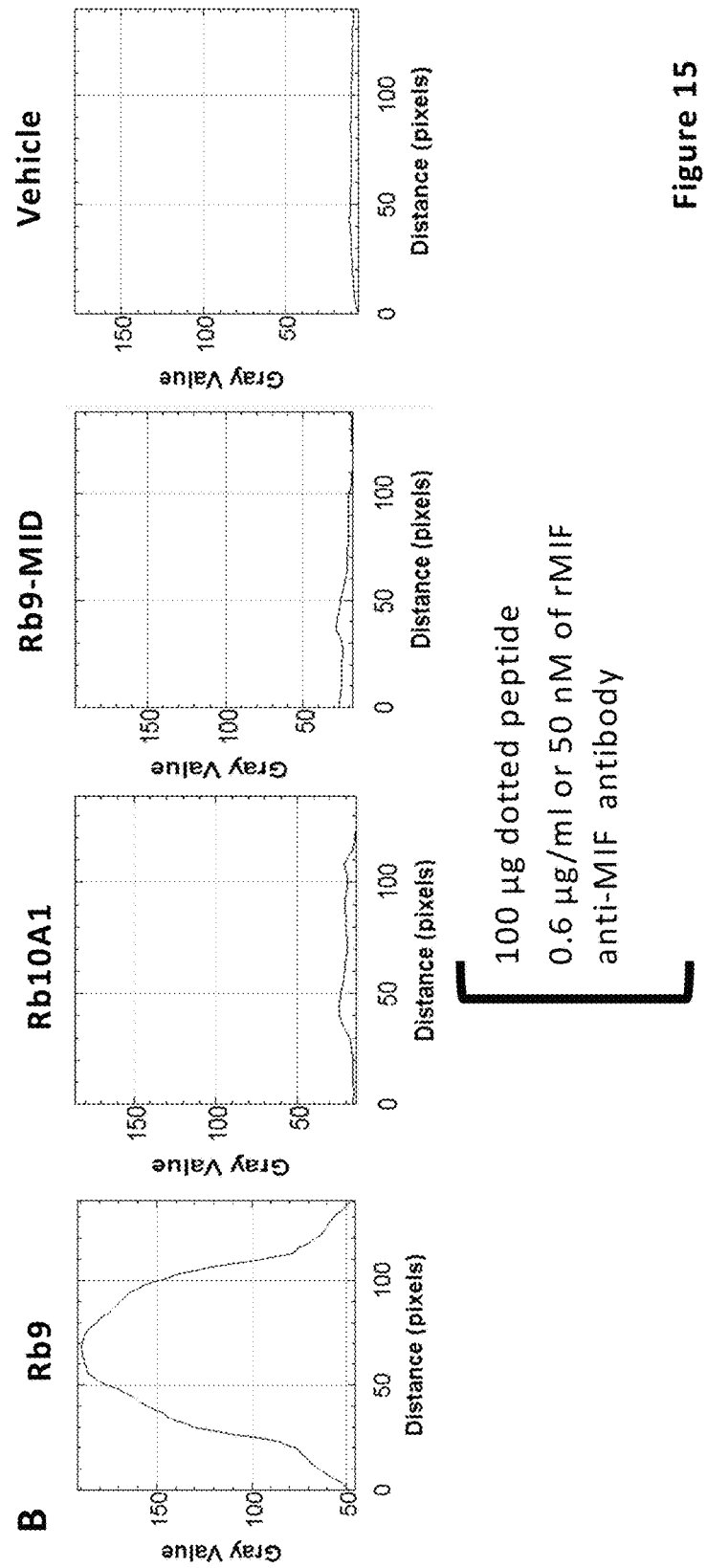
Figure 16:
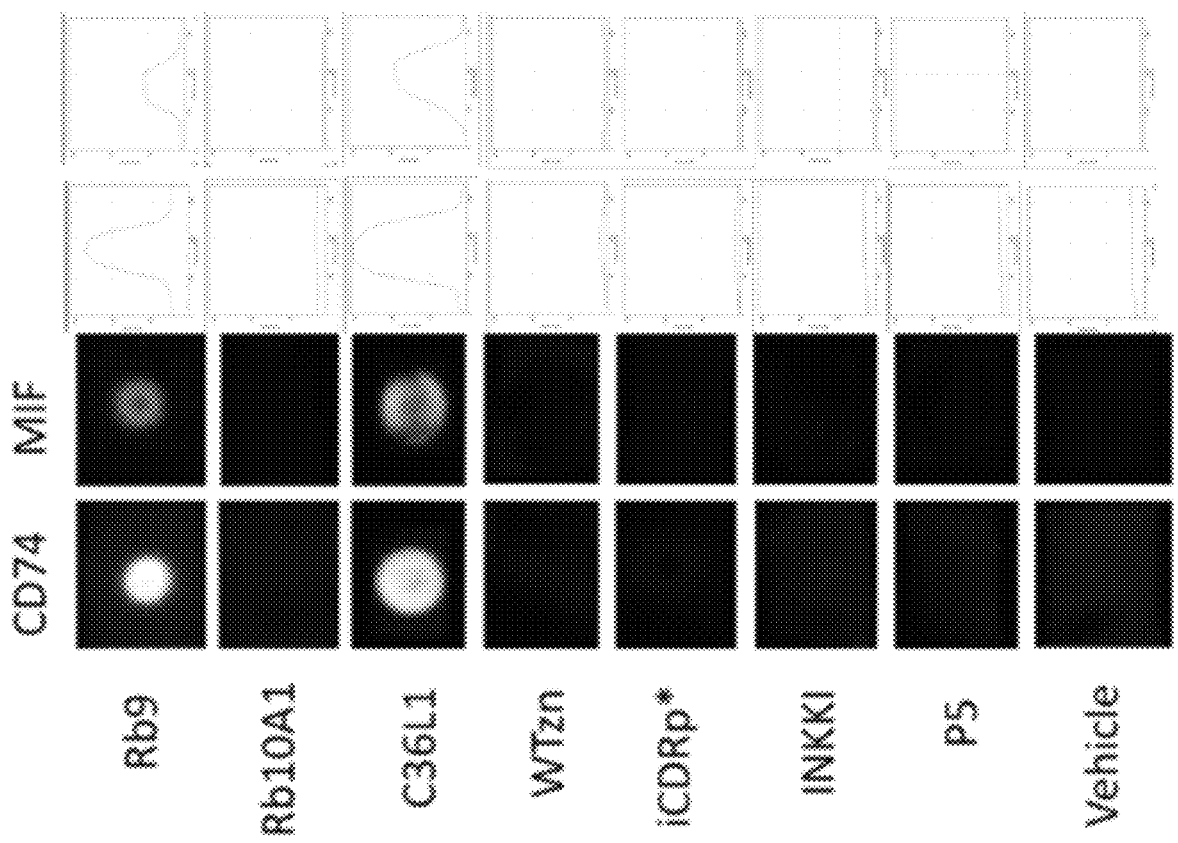
FIG. 16 shows the reactivity by dot blotting of Rb9 (but not Rb10A1 and 4 other peptides) with CD74. C36L1 derived from another Ig CDR was equally reactive.

Peptides can immunomodulate the anti-tumor response by interaction with MIF and the MIF/CD74 axis mainly on macrophages and dendritic cells. By using dot-blotting and recombinant MIF and CD74, it was shown that Rb9 (but not Rb9-MID and Rb10A1) binds to rMIF (FIG. 15) and even more strongly to CD74 (FIG. 16), the recognized MIF's receptor. Rb9 binding to CD74 and MIF is very similar to that of another CDR peptide (C36L1), which interferes with the MIF signaling through the MIF/CD74 axis (Figueiredo et al., 2018).

Example 11

Figure 17:
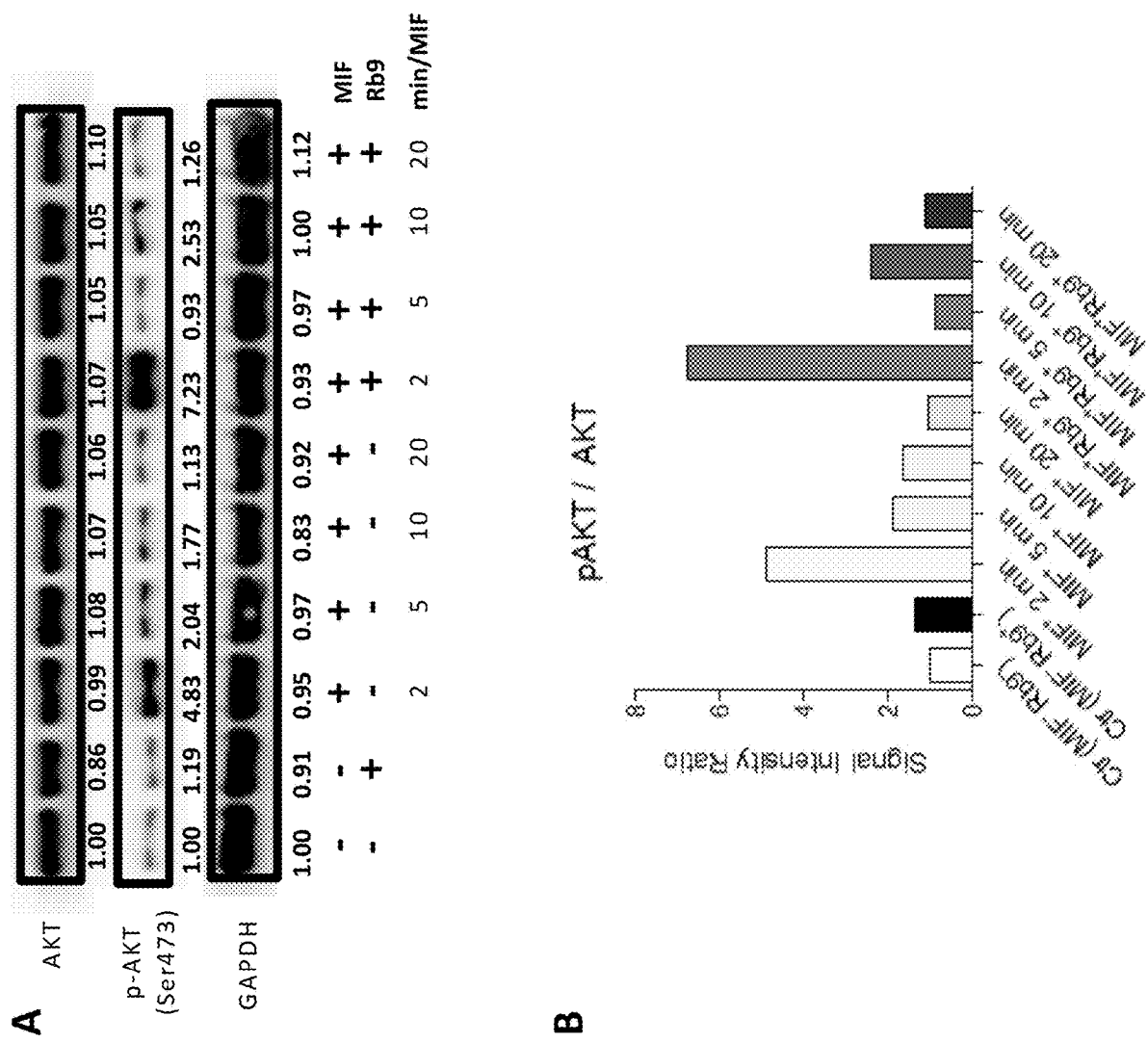
FIG. 17 shows that murine dendritic cells pre-stimulated with Rb9 for 6 h and then treated with recombinant-MIF, increased Akt phosphorylation (Ser 473), over the level of rMIF alone, with short incubation.
Figure 18:
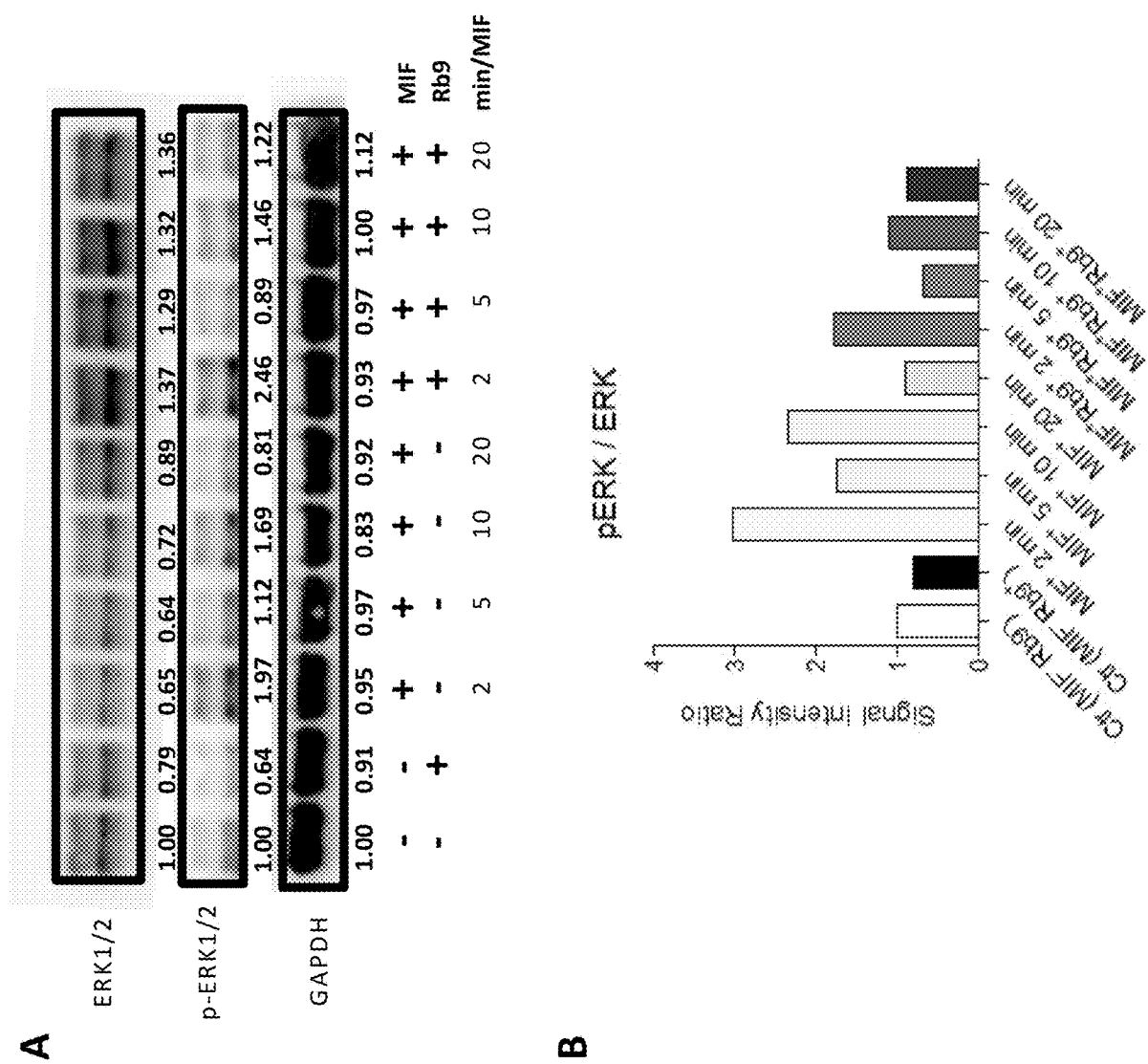
FIG. 18 shows that murine dendritic cells pre-stimulated with Rb9 for 6 h and treated with recombinant-MIF reduced ERK1/2 phosphorylation, with different incubation times.
Figure 19:
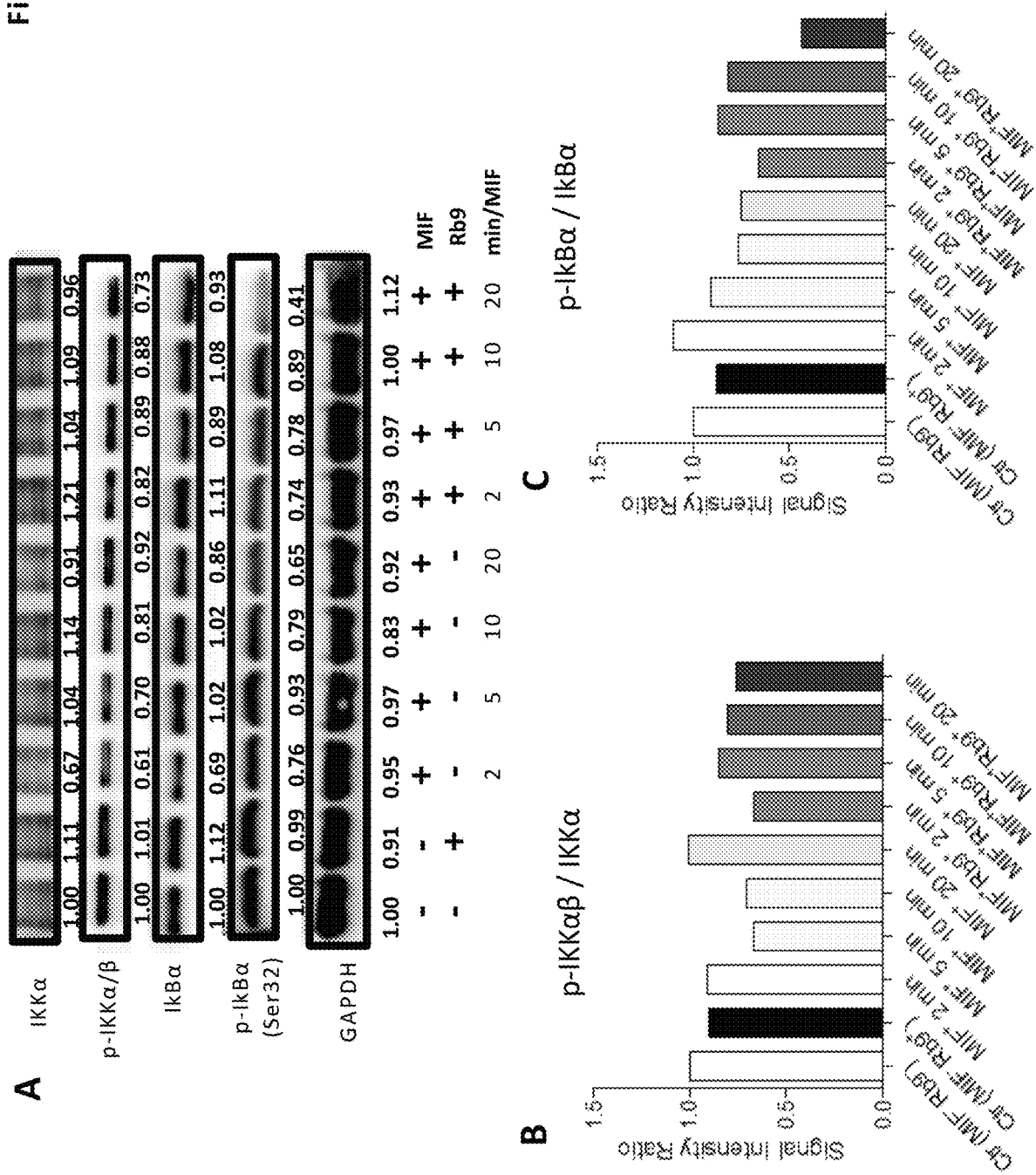
FIG. 19 shows that murine dendritic cells pre-stimulated with Rb9 for 6 h and treated with recombinant-MIF, decreased IKKαβ and IkBα with short incubation.
Figure 20:
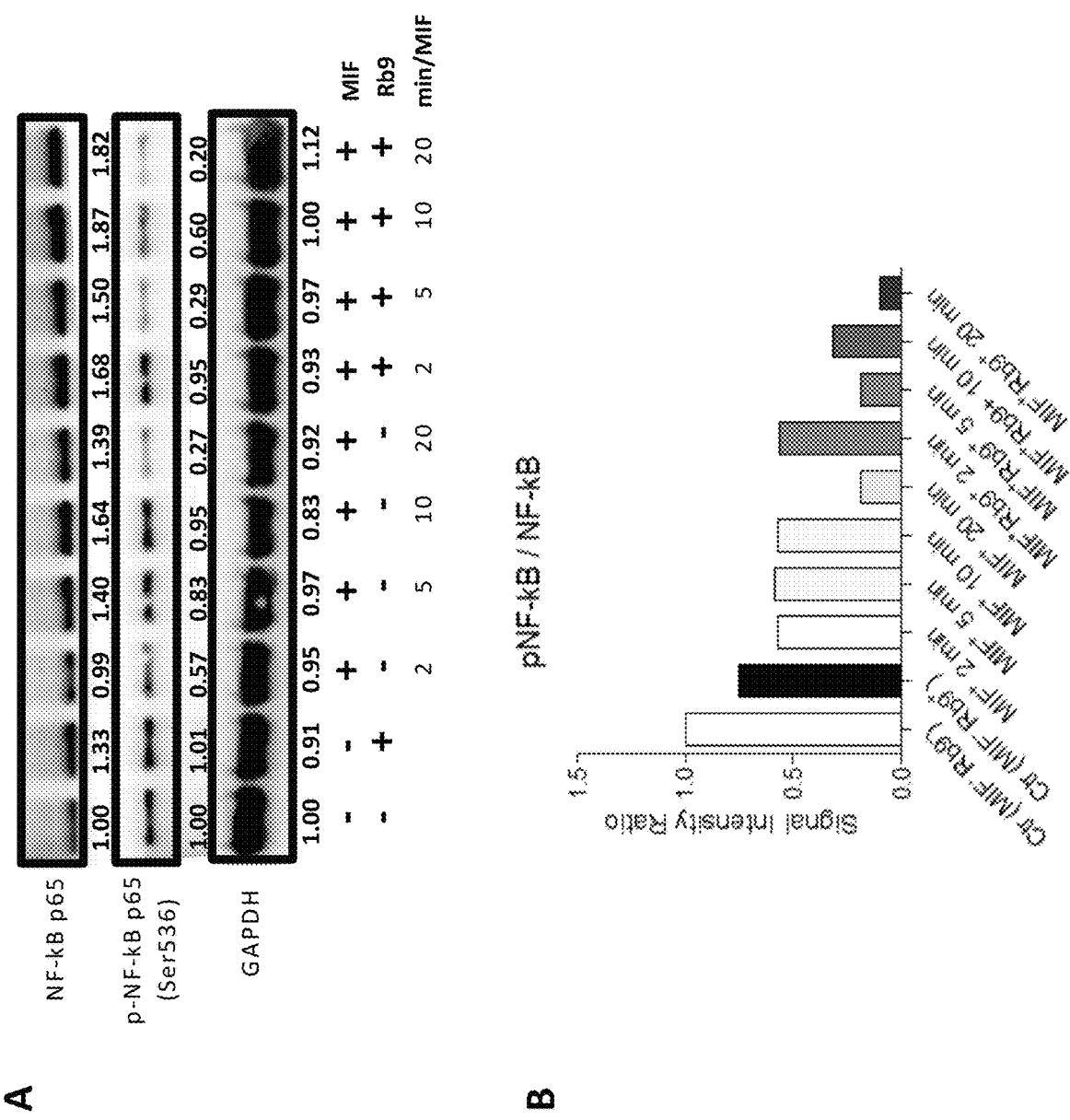
FIG. 20 shows that murine dendritic cells pre-stimulated with Rb9 for 6 h and treated with recombinant-MIF decreased intracellular NFkB p65 phosphorylation (Ser536) for 5, 10, and 20 min of incubation.

Experiments aimed at defining the Rb9 role on the MIF/CD74 axis based on the binding data shown in Example 11 are described. Dendritic cells were pre-incubated with Rb9 for 6 h and then with rMIF for 2, 5, 10 and 20 min. Early incubation with MIF increased p-Akt (Ser473). Phosphorylation increased even more when MIF was added to DCs pre-incubated with Rb9. This additive effect indicates that Rb9 does not block MIF induced Akt phosphorylation and contrariwise increases the effect (FIG. 17). The early peak (2 min) of Akt phosphorylation is not maintained with time suggesting active Akt signaling pathway. MIF also triggered p-ERK1/2 formation in DCs. In this case, pre-incubation with Rb9 reduced p-ERK1/2, which could be translated as a negative modulation of MIF signaling (FIG. 18). The effects of Rb9 on the phosphorylation of IKKαβ and IkBα and of NF-κB (FIG. 20), particularly in the latter, tended to attenuate the MIF response.

Example 12

Figure 21:
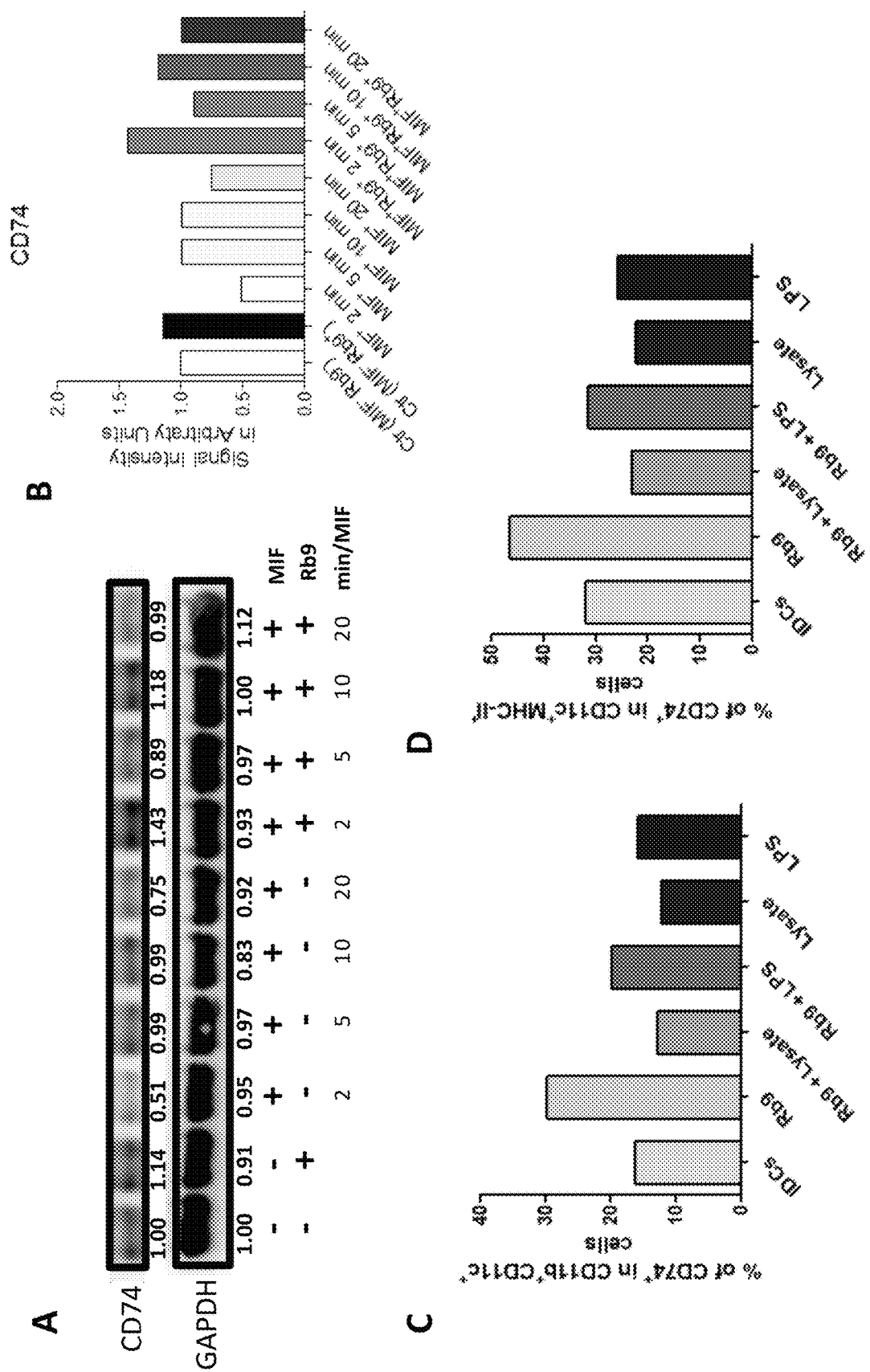
FIG. 21 shows that murine dendritic cells stimulated by Rb9 increased the expression of CD74 in lysed cells and in both isolated populations CD11b+CD11c+ and CD11c+ MHCII+

MIF uses CD74 as a main receptor in macrophages and dendritic cells. Nevertheless, MIF alone did not increase the expression of CD74 but added to Rb9, did so. Rb9 promoted the increased expression of CD74 in both CD11b+CD11c+ and CD11c+MHC-II+ cells (FIG. 21).

Example 13

Figure 22:
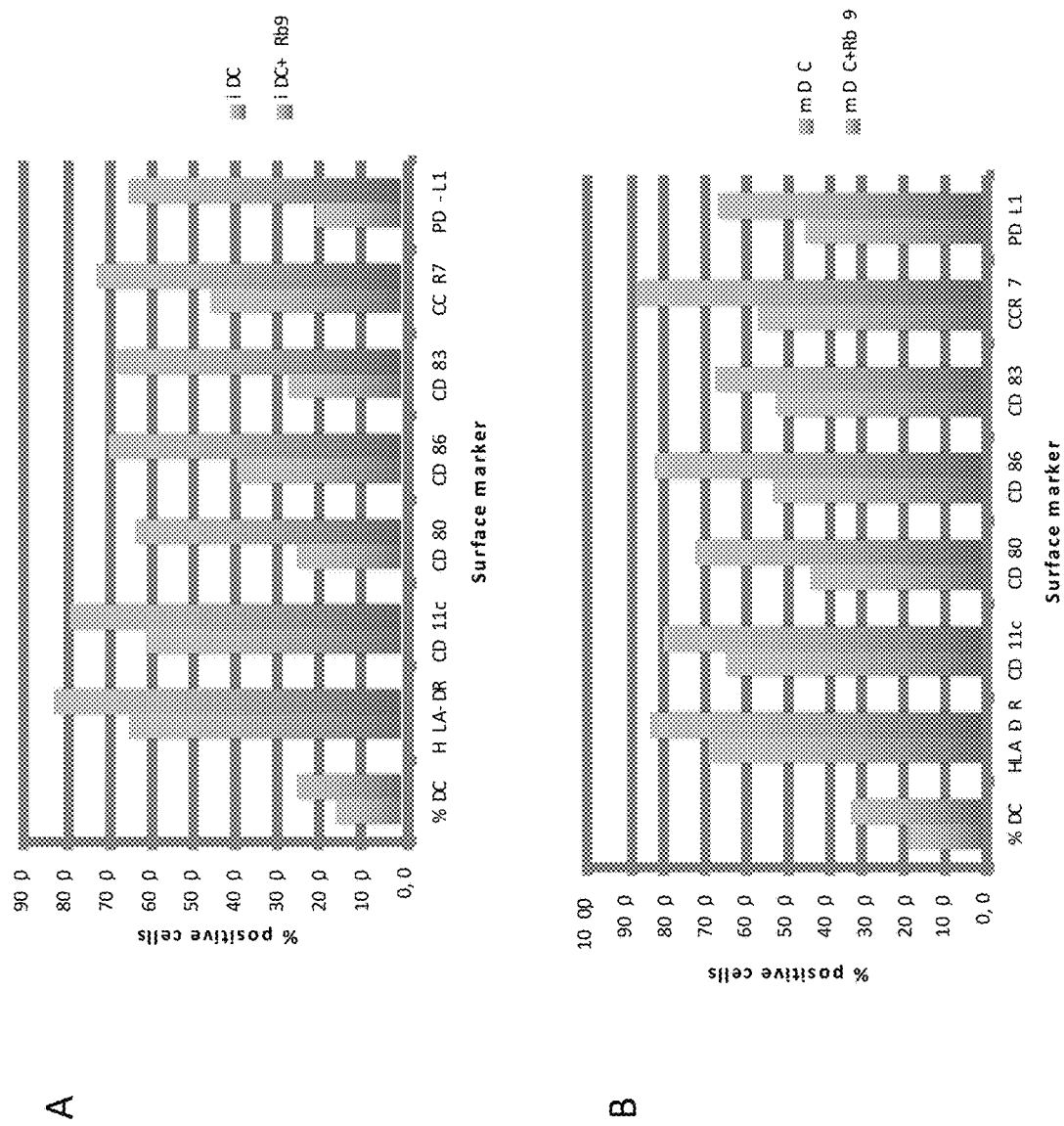
FIG. 22 shows that Rb9 added to in vitro differentiated human monocyte-derived dendritic cells (mo-DC) affected their surface phenotype, enhancing differentiation and expression of maturation markers, both when added alone or in combination with a physiological stimulus like TNF-alpha.

Rb9 showed immunomodulatory activity upon mouse DC. In this experiment, Rb9 activity upon human Mo-DC membrane phenotype was investigated. Mo-DC obtained from healthy donors were treated, at day 5, with Rb9 (50 μg/mL) and after 2 further days in culture, cells were harvested and used for the analysis of membrane phenotype, which showed that Rb9 enhanced the expression of activation markers on immature mo-DC (FIG. 22 A). Also, on day 5, both Rb9 (50 μg/mL) and TNF-alpha (50 ng/mL) were added to the immature mo-DC and two days later the cells were equally harvested and analyzed. This analysis showed that also in the presence of a maturation stimulus, Rb9 affected the surface phenotype of mo-DCs, further enhancing the expression of maturation markers on the surface of the cells (FIG. 22 B).

Example 14

Figure 23:
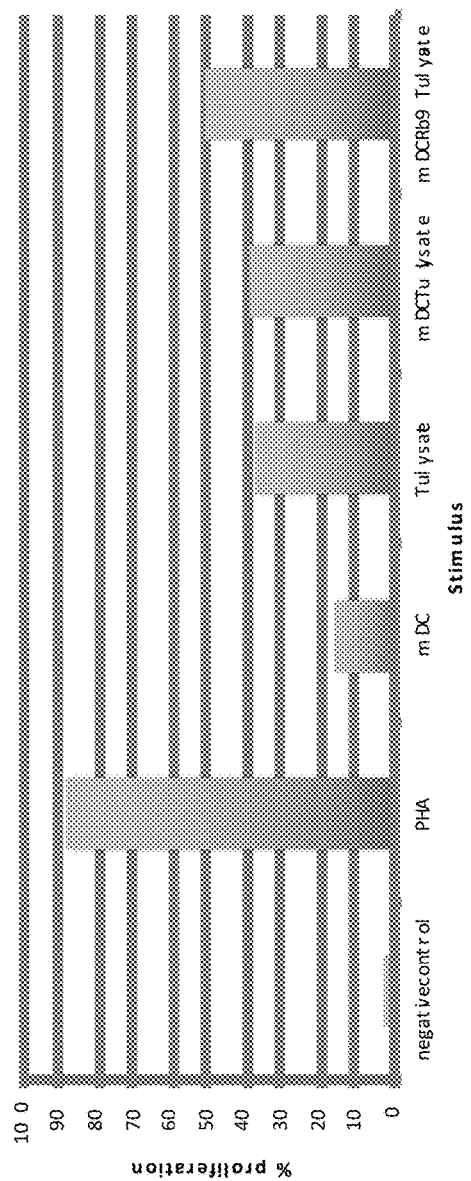
FIG. 23 shows that Rb9 enhanced human mo-DC ability to induce allogeneic lymphocyte proliferation when added together with a tumor lysate to human mo-DC.

Since Rb9 affected human mo-DC phenotype, we analyzed its effects on the cells' lympho-stimulatory ability. Mo-DC obtained as described in Example 14, at day 5 were stimulated with either TNF-alpha alone (mDC), TNF-alpha and tumor lysate (mDC+Tu lysate) or with TNF, tumor lysate and Rb9 (all at the concentrations described before) were harvested and co-cultured with CFSE-labeled allogeneic lymphocytes at an mo-DC:lymphocyte rate of 1:30. After two days in co-culture, the dilution of CFSE in lymphocytes was evaluated as a measurement of lymphocyte proliferation. Rb9 was able to further enhance the lympho-stimulatory ability of mo-DC, which was already stimulated by the tumor lysate (FIG. 23).

Example 15

Figures 24, 24A:
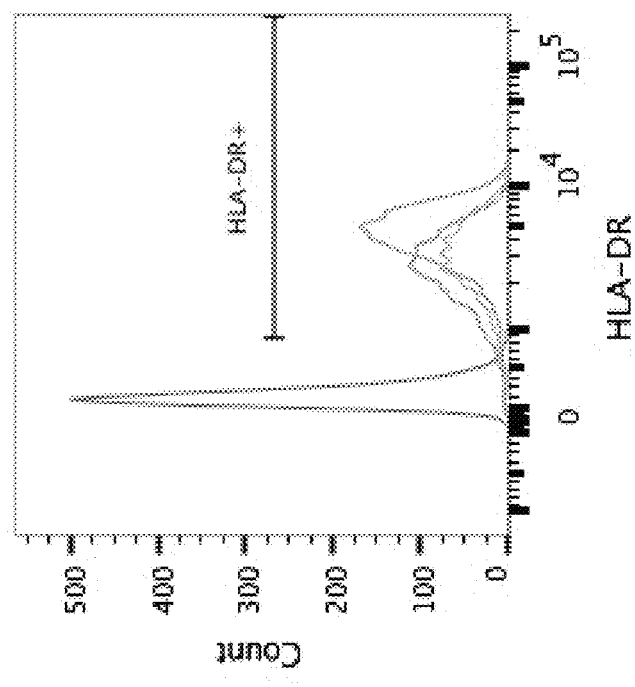
FIG. 24 shows that Rb9 affected also the surface phenotype of mo-DC derived from monocytes of cancer patients, but the effects were heterogeneous.
Figure 24B:
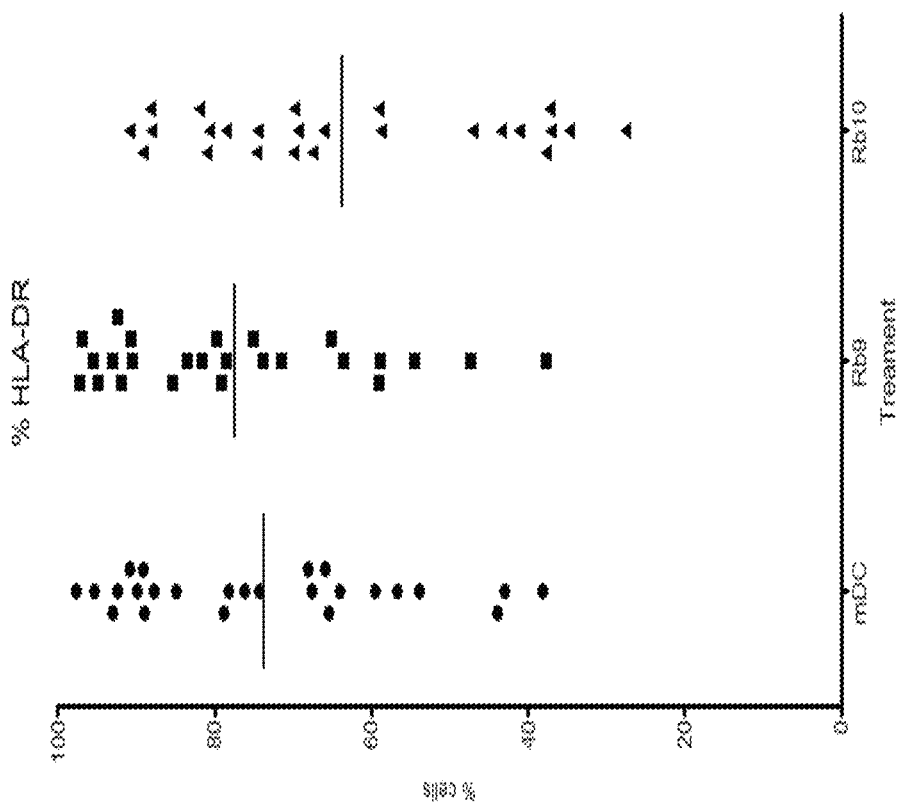
Figure 24C:
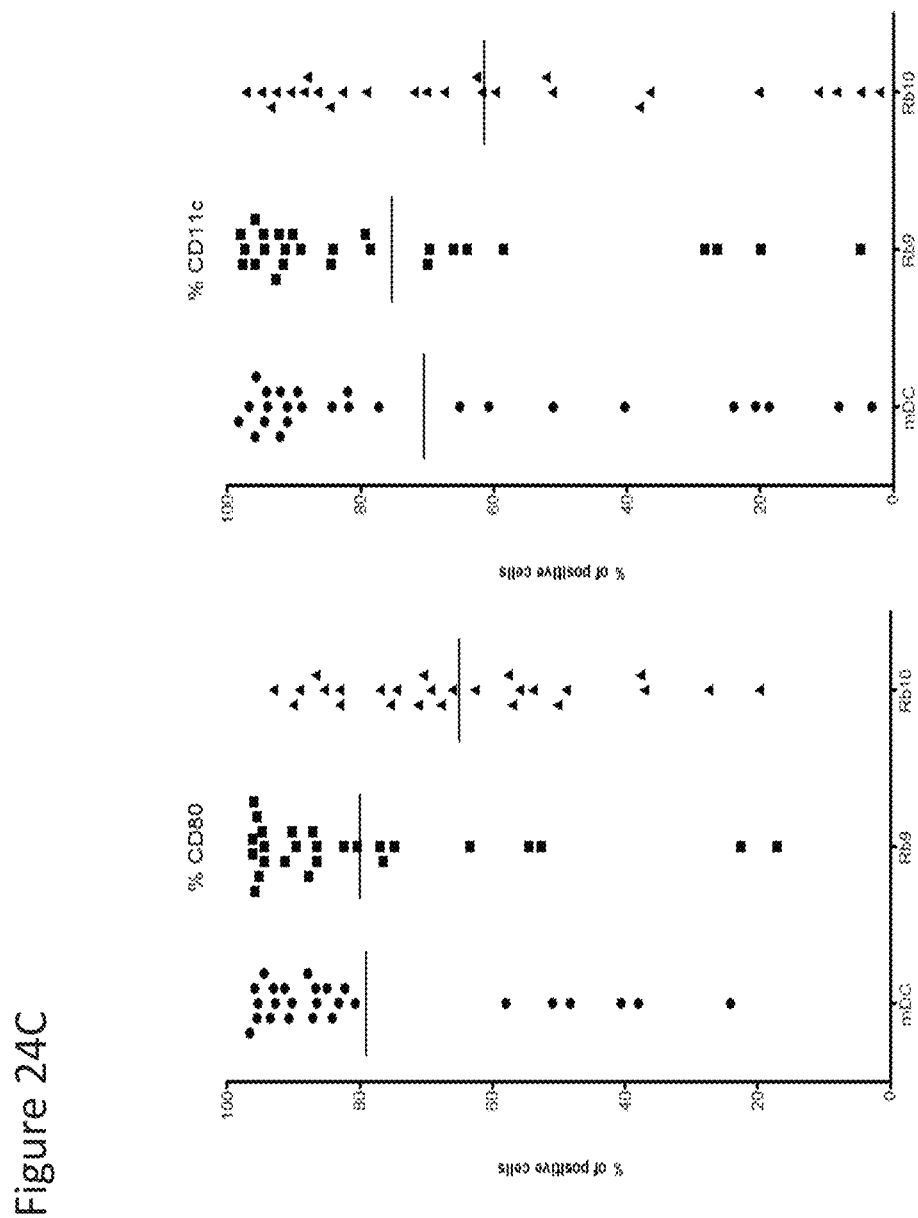
Figure 24C:
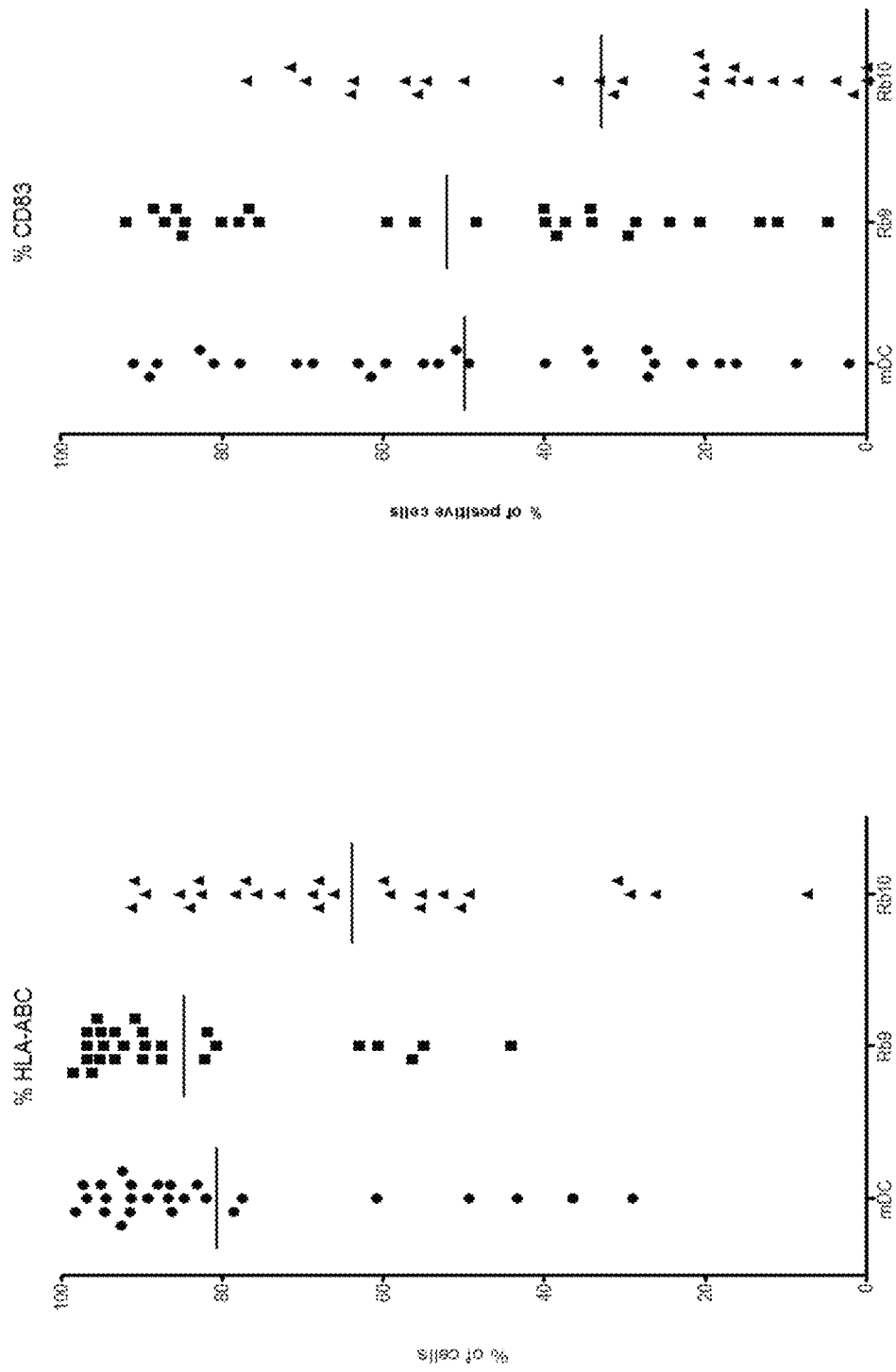

Rb9 had the ability to modify human mo-DC, inducing an increase in the expression of differentiation and maturation surface markers and enhancing their lympho-stimulatory ability. Thus, Rb9 effects were analyzed in mo-DC obtained from cancer patients' monocytes. These cells were obtained as described before and, again, Rb9 affected their surface phenotype (FIG. 24A). However, the effects of Rb9 on the surface phenotype of the mo-DC, though suggesting a stimulatory activity, contrasting with that of peptide Rb10, were heterogeneous (FIGS. 24B and 24C).

Figure 25:
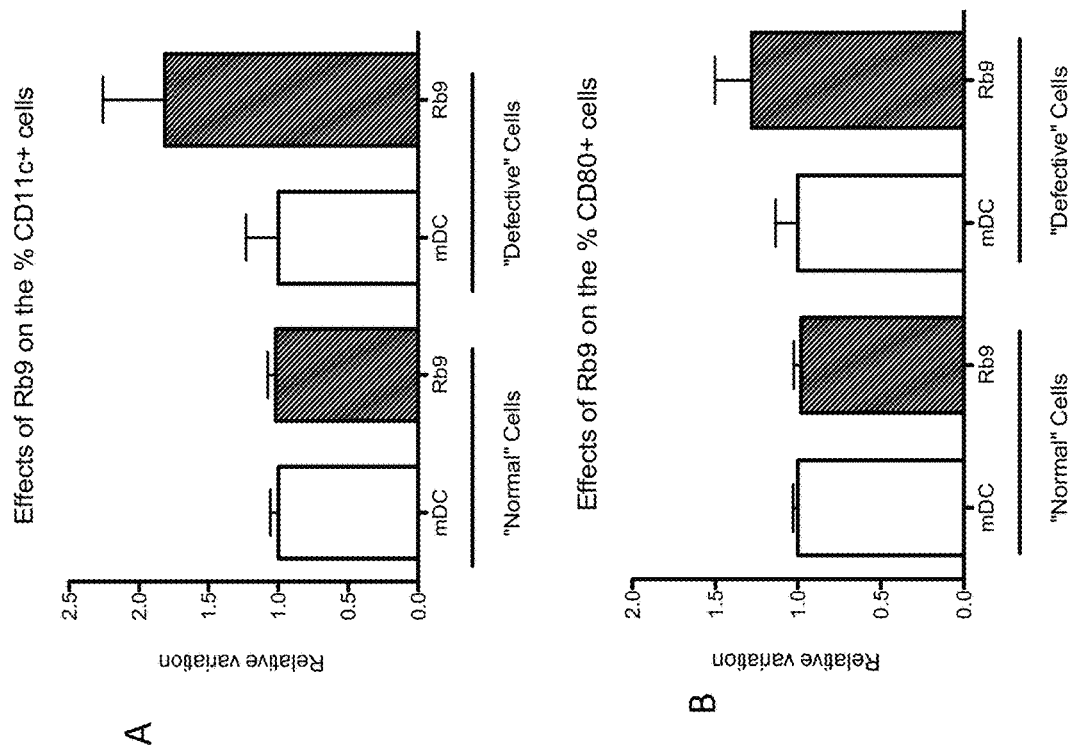
FIG. 25 shows a study of cancer patients that were separated into two groups: one with "normal" mo-DC phenotype and function and a second with a "defective" phenotype (according to their lympho-stimulatory activity). Rb9 showed a clearer effect on the phenotype of "defective" cells.

Since it is well known that mo-DC from cancer patients can be functionally biased, but are not always so, the patients were separated into two groups, according to their mo-DC ability to induce allogeneic T cell proliferation. Patients whose mo-DC induced less than 35% of the phytohemagglutinin A (PHA)-induced response constituted one group ("defective") and those whose mo-DC induced a response higher than 35% of the PHA response, the other ("normal"). When thus separated, it was possible to notice that Rb9 clearly affected the phenotype of the cells from the "defective" mo-DC, but had little effect upon "normal" mo-DC, both when their differentiation (FIG. 25A) or maturation (FIG. 25B) were considered.

Figure 26:
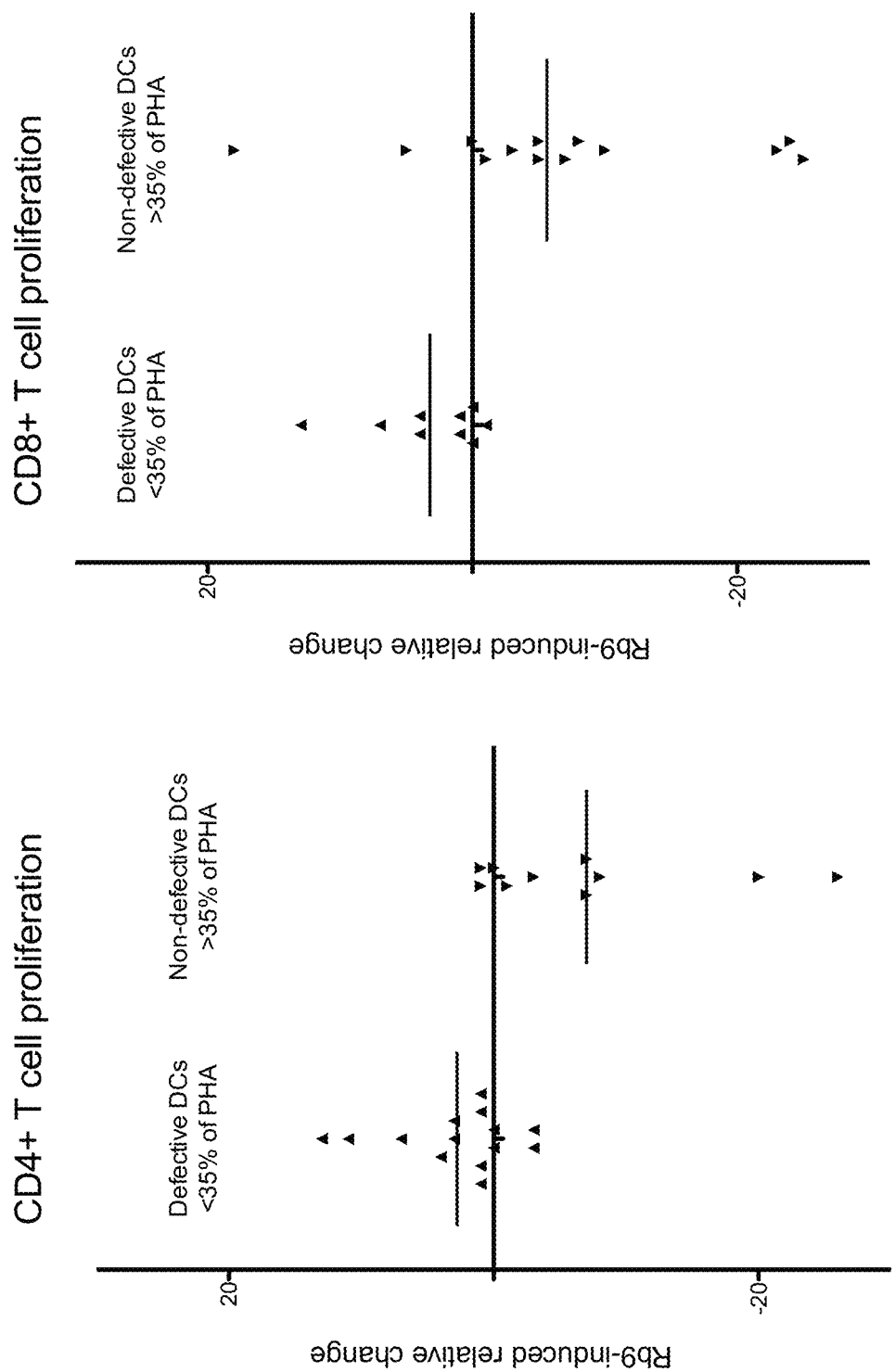
FIG. 26 shows that the effects of Rb9 on the cancer patients' mo-DC ability to induce allogeneic T cell proliferation were opposed, depending on the status of the cells: defective mo-DCs were stimulated and non-defective cells were inhibited by Rb9.

Furthermore, this variation in Rb9 effects was even more striking when the function of the Rb9-treated mo-DC was analyzed by their ability to induce allogeneic T cell proliferation. In this setting, Rb9 showed contrasting effects: while it enhanced the ability of "defective" mo-DC, it inhibited the lympho-stimulatory activity of "normal" mo-DC (FIG. 26).

Example 16

Figure 27:
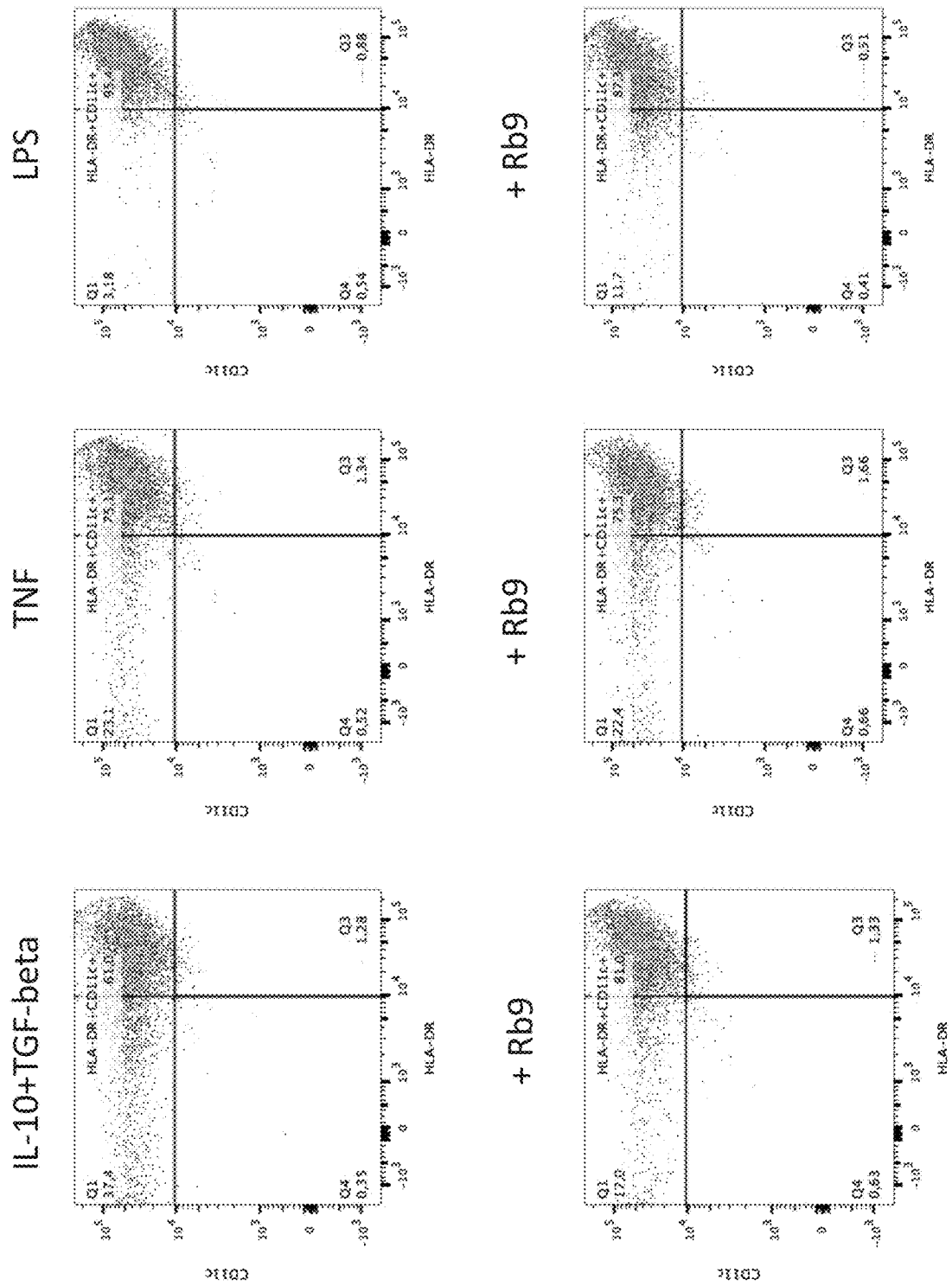
FIG. 27 shows the immunomodulatory activity of Rb9. When Rb9 was added to mo-DC generated under "tolerogenic" conditions (TGF-beta+IL-10), it increased the differentiation of mo-DC; when the mo-DCs were stimulated by a mild stimulus (TNF-alpha), Rb9 did not affect significantly the differentiation of the cells, but when the cells were strongly stimulated by LPS, Rb9 was inhibitory.

Rb9 seems to have rather an immunomodulatory than an immunostimulatory activity. To further evaluate and confirm this property, mo-DC were generated from healthy donors cells in three different conditions, all in the presence of GM-CSF (50 ng/mL) and IL-4 (50 ng/mL). To one group of cells at day 5, TGF-beta (10 ug/mL) and IL-10 (1 ug/mL) were added; to a second group, at day 5, TNF-alpha was added and to a third group, LPS (100 ng/mL) was added at day 6. The first condition is known to induce phenotypic changes in mo-DC consistent with a tolerogenic activity of the cells, while both other conditions generate mature mo-DC, with LPS representing a stronger maturation stimulus than TNF-alpha. To each group, Rb9 was added or not at day 5. At day 7 all cells were harvested and analyzed by flow cytometry. When differentiation markers (CD11c and HLA-DR) were analyzed, the phenotype of the cells in each group corresponded to the expected, but when the cells of each group were stimulated with Rb9, the effects of the peptide diverged. While Rb9 increased the percentage of cells with the expected mo-DC phenotype (CD11c+HLA-DR+) in the TGF-beta+IL-10 group, it had little effect on the TNF group and decreased the number of cells with this phenotype in the LPS-treated cells (FIG. 27).

Figure 28:
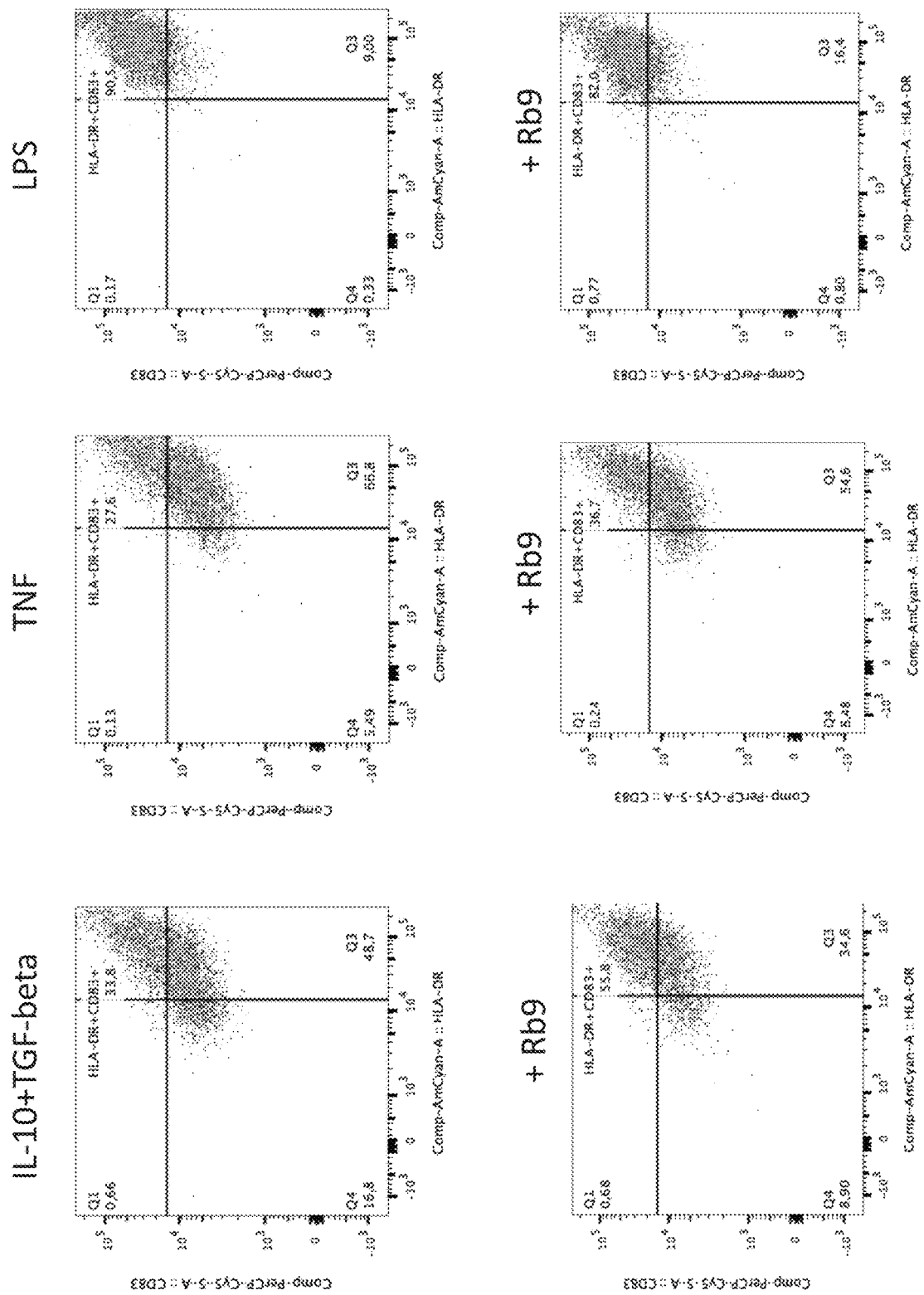
FIG. 28 also shows the immunomodulatory activity of Rb9. When Rb9 was added to mo-DC generated under "tolerogenic" conditions (TGF-beta+IL-10), Rb9 increased the maturation of mo-DC, when the mo-DC received a mild stimulus (TNF-alpha), it enhanced their maturation, but when the cells were strongly stimulated by LPS, Rb9 was inhibitory.
Figure 29:
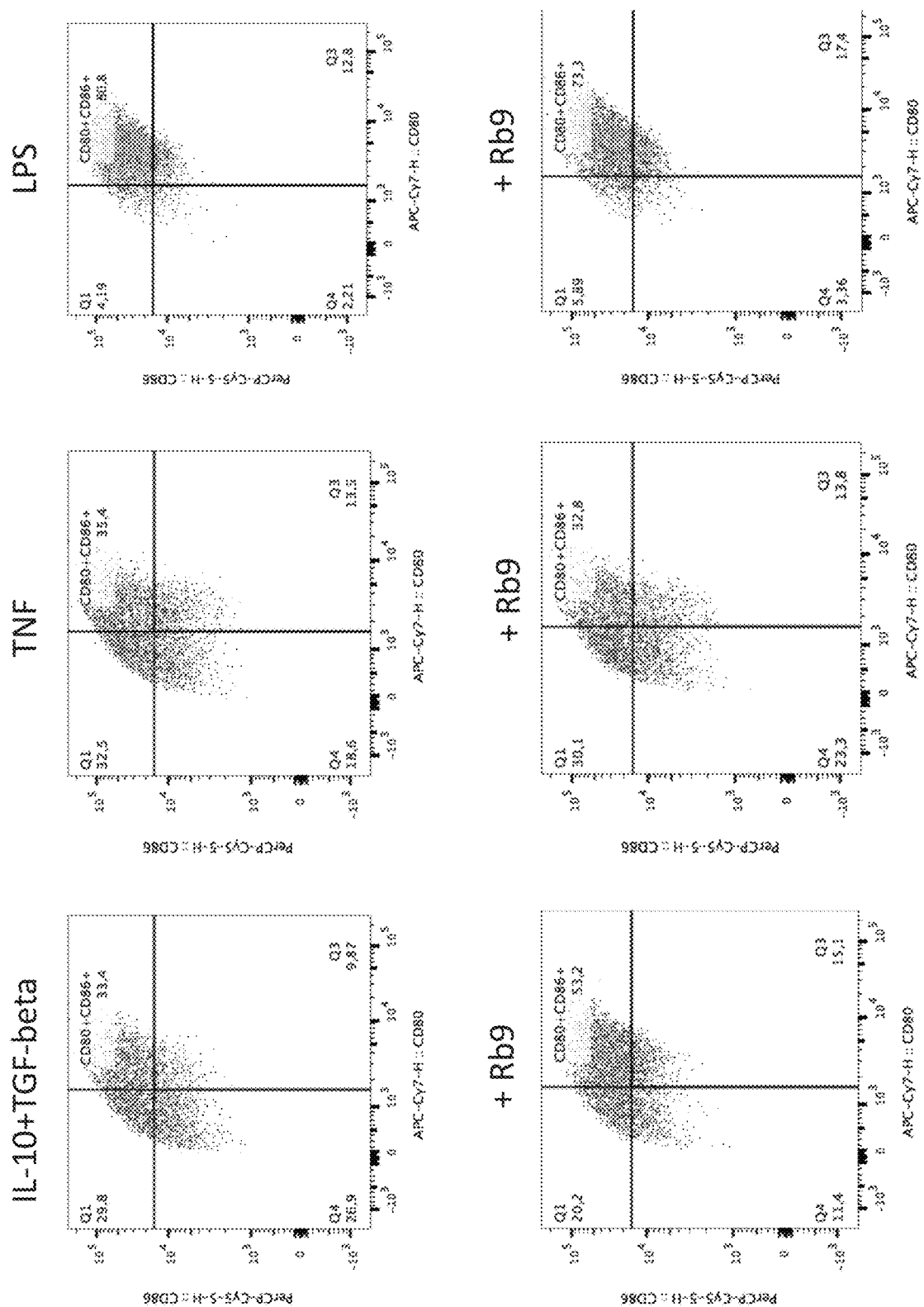
FIG. 29 also demonstrates the immunomodulatory activity of Rb9. When Rb9 was added to mo-DC generated under "tolerogenic" conditions (TGF-beta+IL-10), Rb9 increased their co-stimulatory potential, when the mo-DC received a mild stimulus (TNF-alpha), Rb9 was partially inhibitory, but when the cells were strongly stimulated by LPS, Rb9 was clearly inhibitory.

A similar contrasting effect of Rb9 was noticed when the frequency of mature, HLA-DR+CD83+cells (FIG. 28) was determined, and when cells double-positive for the co-stimulatory molecules, CD80 and CD86 (FIG. 29), were analyzed.

Example 17

Figure 30:
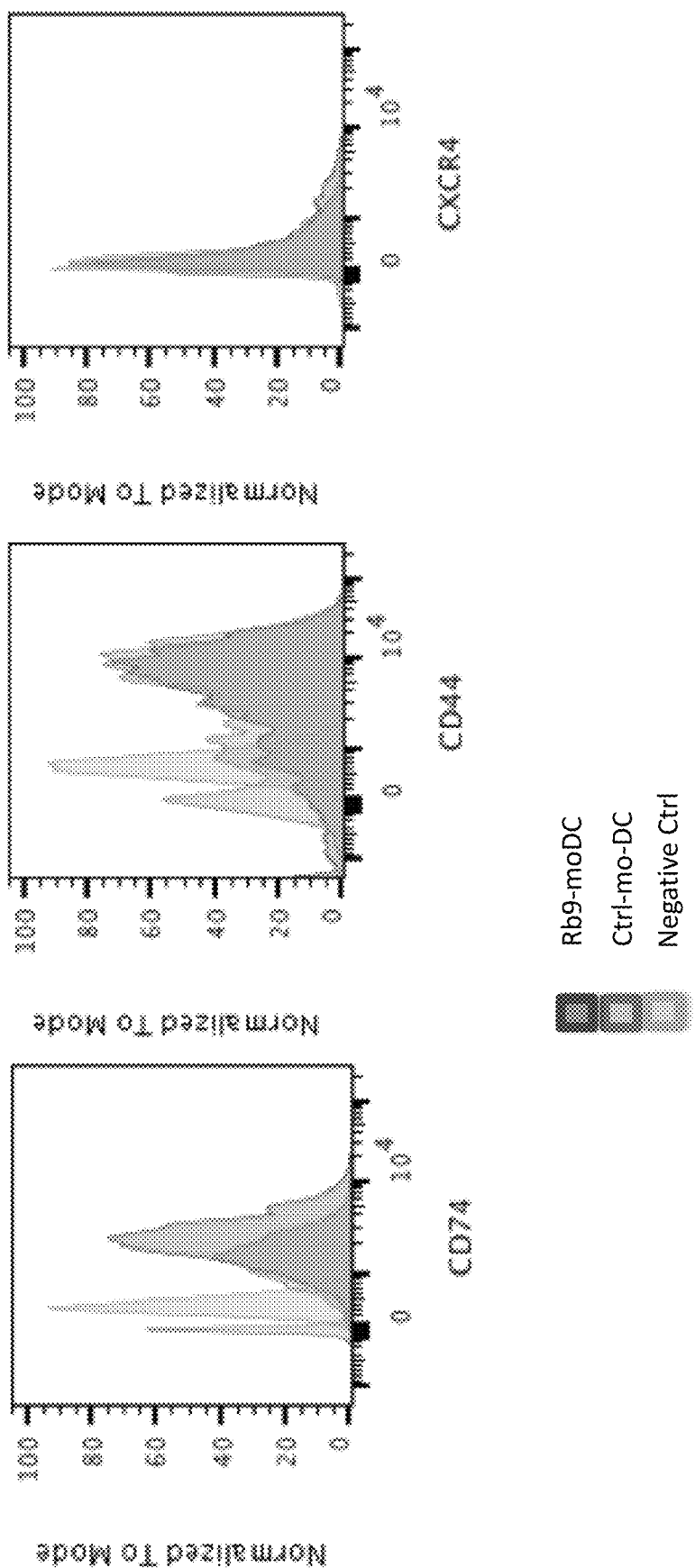
FIG. 30 shows that Rb9 treatment increases the expression of the MIF receptor CD74 and the MIF co-receptor CXCR4 by LPS-stimulated human mo-DC.

Rb9 treatment increases the expression of the MIF receptor CD74 (from 56.8% to 87.5%—evaluated by FITC-labeled monoclonal antibodies) and the MIF co-receptor CXCR4 (from 16.7% to 28.2%—evaluated by PE-Cy5-labeled monoclonal antibodies) by LPS-stimulated human mo-DC (FIG. 30). CD44 expression was evaluated by BV-421-labeled monoclonal antibodies and negative controls in the figure refer to unlabeled cells.

Figure 31:
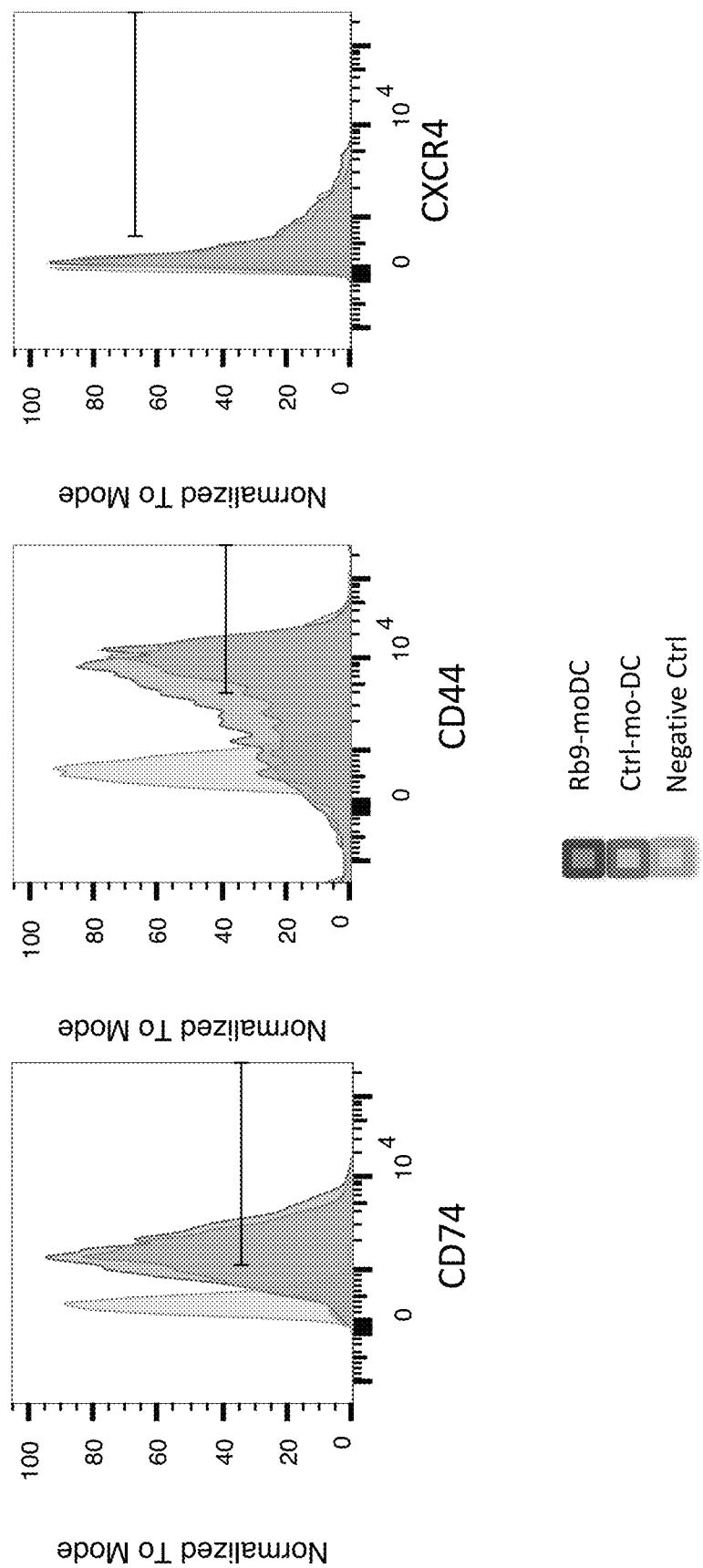
FIG. 31 shows that Rb9 treatment decreases the expression of the MIF co-receptor CD44 by TGF-beta+IL-10-treated human mo-DC, evaluated both by the frequency of positive cells labeled by anti-CD44 mAb, and by MFI, when the cells were exposed to Rb9.

Rb9 treatment decreases the expression of the MIF co-receptor CD44 by TGF-beta+IL-10-treated human mo-DC, evaluated both by the frequency of positive cells labeled by BV-421-labeled anti-CD44 mAb, from 57% to 52% and, more clearly, by MFI, where a 20% reduction in intensity was noted when the cells were exposed to Rb9 (FIG. 31). Negative controls in the figure refer to unlabeled cells.

Example 18

Figure 32:
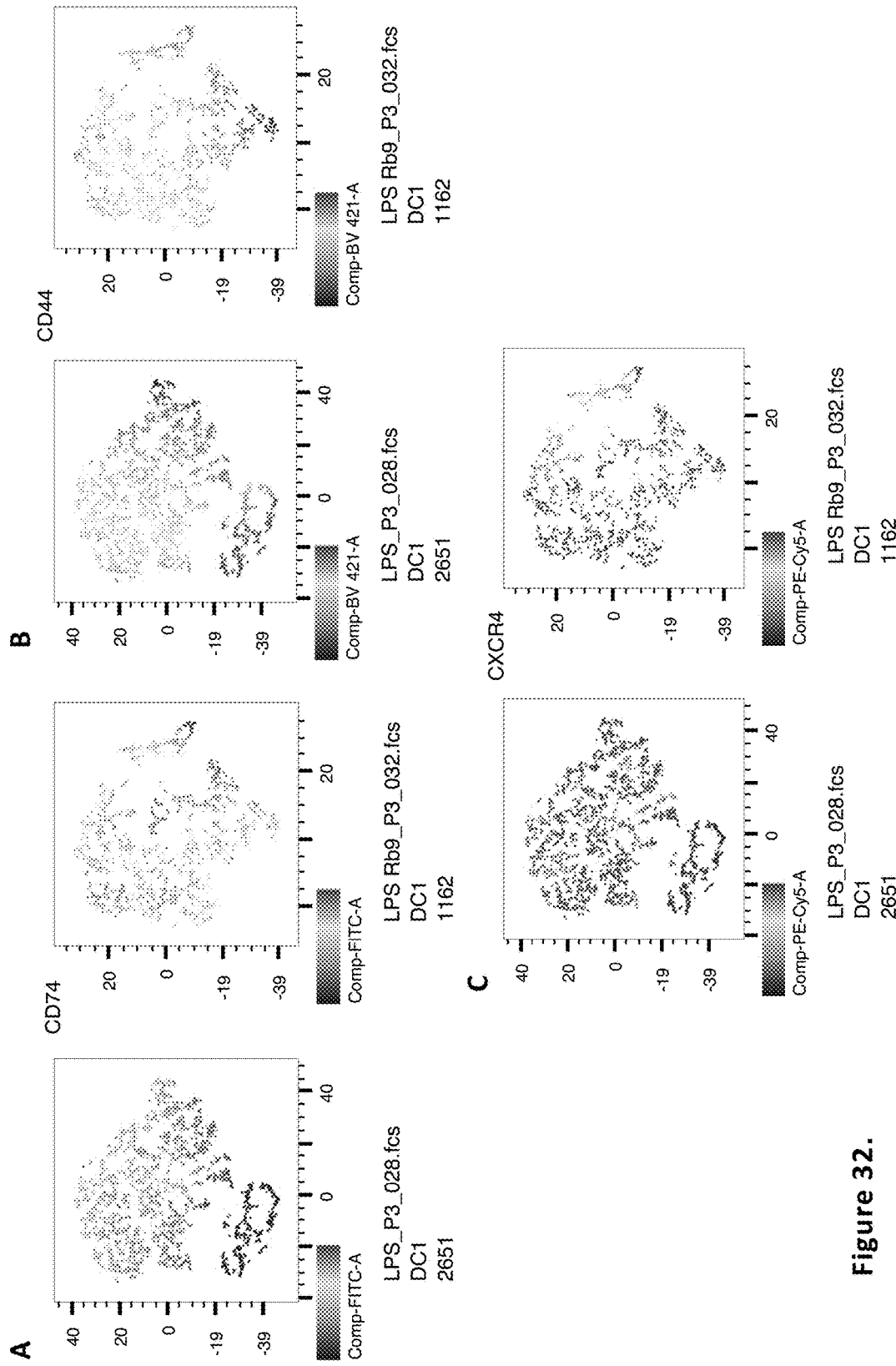
FIG. 32 shows the disappearance of a $CD74^{low}CXCR4^{low}$ cell subpopulation after Rb9 treatment of LPS-stimulated human mo-DC.

The disappearance of a $CD74^{low}CXCR4^{low}$ cell subpopulation is shown (FIG. 32) after Rb9 treatment of LPS-stimulated human mo-DC and an overall change in the distribution of these markers in the cells, as detected by T-Distributed Stochastic Neighbor Embedding (tSNE) analysis of the same cells shown in FIG. 30. The parameters included in the analysis were the expression of HLA-DR (BV-510 labeled mAb), PD-L1 (PE-labeled mAb), CD44

(BV-421-labeled mAb), CD74 (FITC-labeled mAb) and CXCR4 (PE-Cy5-labeled mAb).

REFERENCES

Polonelli, L., Ponton, J., Elguezabal, N., Moragues, M. D., Casoli, C., Pilotti, E., Ronzi, P., Dobroff, A S., Rodrigues, E G., Juliano, M A., Maffei, D L., Magliani, W., Conti, S., and Travassos, L R. Antibody complementarity-determining regions (CDRs) can display differential antimicrobial, antiviral and antitumor activities. PLoS One (2008); 3, e2371.

Magliani W, Conti S, Cunha R L, Travassos L R, Polonelli L. Antibodies as crypts of antiinfective and antitumor peptides. Current Medical Chemistry (2009); 16(18): 2305-23.

Morea, V., Tramontano, A., Rustici, M., Chothia, C., Lesk, A. M. Conformations of the third hypervariable region in the VH domain of immunoglobulins. Journal Molecular Biology (1998); 275, 269-94.

Girola N, Matsuo A L, Figueiredo C R, Massaoka M H, Farias C F, Arruda D C, Azevedo R A, Monteiro H P, Resende-Lara P T, Cunha R L, Polonelli L, Travassos L R. The Ig VH complementarity-determining region 3-containing Rb9 peptide, inhibits melanoma cells migration and invasion by interactions with Hsp90 and an adhesion G-protein coupled receptor. Peptides (2016); 85:1-15.

Yin B W, Kiyamova R, Chua R, Caballero O L, Gout I, Gryshkova V, Bhaskaran N, Souchelnytskyi S, Hellman U, Filonenko V, Jungbluth A A, Odunsi K, Lloyd K O, Old L J, Ritter G. Monoclonal antibody MX35 detects the membrane transporter NaPi2b (SLC34A2) in human carcinomas. Cancer Immunulogy (2008); 8.3.

Arruda D C, Santos L C, Melo F M, Pereira F V, Figueiredo C R, Matsuo A L, et al. beta-Actin-binding complementarity-determining region 2 of variable heavy chain from monoclonal antibody C7 induces apoptosis in several human tumor cells and is protective against metastatic melanoma. Journal of Biological Chemistry (2012); 287: 14912-14922.

Massaoka et al., Melanoma: Perspectives of a vaccine based on peptides; in M. Giese (ed) Molecular Vaccines, vol 1. Springer, Wien, 2013; p 397-412

Haney E F, Hancock R E W Peptide Design for Antimicrobial and Immunomodulatory Applications. Biopolymers. (2013); 100(6): 572-583.

Srinivasan M, Roeske R W. Immunomodulatory peptides from IgSF proteins: a review. Current Protein Peptide Science (2005); 6(2), 185-196.

Magliani W, Conti S, Giovati L, Zanello P P, Sperindè M, Ciociola T, Polonelli L. Antibody Peptide based antifungal immunotherapy. Frontiers in Microbiology (2012); 3, 190

Figueiredo C R, Matsuo A L, Azevedo R A, Massaoka M H, Girola N, Polonelli L, Travassos L R. A novel microtubule de-stabilizing complementarity-determining region C36L1 peptide displays antitumor activity against melanoma in vitro and in vivo. Scientific Reports (2015); 5, 14310.

Dobroff A S, Rodrigues E G, Juliano M A, Friaca D M, Nakayasu E S, Almeida I C, et al. Differential Antitumor Effects of IgG and IgM Monoclonal Antibodies and Their Synthetic Complementarity-Determining Regions Directed to New Targets of B16F10-Nex2 Melanoma Cells. Translation Oncology (2010); 3, 204-217.

Gabrielli E, Pericolini E, Cenci E, Ortelli F, Magliani W, Ciociola T, Bistoni F, Conti S, Vecchiarelli A, Polonelli L. Antibody complementarity-determining regions (CDRs): a bridge between adaptive and innate immunity. PLoS One (2009); 4, e8187

Gabrielli E, Pericolini, E., Cenci, E., Ortelli, F., Magliani, W., Ciociola, T., Bistoni, F., Conti, S., Vecchiarelli, A., Polonelli, L. Antibody constant region peptides can display immunomodulatory activity through activation of the Dectin-1 signalling pathway. PLoS One (2012); 7, e43972.

Seya T, Shime H, Takeda Y, Tatematsu M, Takashima K, Matsumoto M. Adjuvant for vaccine immunotherapy of cancer—focusing on Toll-like receptor 2 and 3 agonists for safely enhancing antitumor immunity. Cancer Science (2015); 106(12), 1659-1668.

Sica A, Mantovani A. Macrophage plasticity and polarization: in vivo veritas. J. Clin. Invest. (2012); 122: 787-795.

Gordon S, Taylor P R Monocyte and macrophage heterogeneity. Nat. Rev. Immunol. (2005); 5, 953-964

Steinman, R. M., Witmer, M. D. (1978). Lymphoid dendritic cells are potent stimulators of the primary mixed leukocyte reaction in mice. Proceedings of the National Academy of Sciences of the United States of America, 75(10), 5132-5136.

Inaba, K., Steinman, R. M., Pack, M. W., Aya, H., Inaba, M., Sudo, T., et al. (1992). Identification of proliferating dendritic cell precursors in mouse blood. The Journal of Experimental Medicine, 175(5), 1157-1167.

Sallusto, F., Lanzavecchia, A. Efficient presentation of soluble antigen by cultured human dendritic cells is maintained by granulocyte/macrophage colony-stimulating factor plus interleukin 4 and downregulated by tumor necrosis factor alpha. The Journal of Experimental Medicine (1994); 179(4), 1109-1118.

Berzofsky, J. A., Terabe, M., Oh, S., Belyakov, I. M., Ahlers, J. D., Janik, J. E., & Morris, J. C. Progress on new vaccine strategies for the immunotherapy and prevention of cancer. The Journal of Clinical Investigation (2004); 113(11), 1515-1525.

Barbuto, J. A. M., Ensina, L. F. C., Neves, A. R., Bergami-Santos, P. C., Leite, K. R. M., Marques, R., et al. Dendritic cell-tumor cell hybrid vaccination for metastatic cancer. Cancer Immunology, Immunotherapy, (2004); 53(12), 1111-1118.

Barbuto, J. A. M. Are dysfunctional monocyte-derived dendritic cells in cancer an explanation for cancer vaccine failures? Immunotherapy (2013); 5(2), 105-107.

Baleeiro, R. B., Anselmo, L. B., Soares, F. A., Pinto, C. A. L., Ramos, O., Gross, J. L., et al. High frequency of immature dendritic cells and altered in situ production of interleukin-4 and tumor necrosis factor-alpha in lung cancer. Cancer Immunology, Immunotherapy (2008); 57(9), 1335-1345.

Ramos, R. N., Chin, L. S., Santos, Dos, A. P. S. A., Bergami-Santos, P. C., Laginha, F., Barbuto, J. A. M. Monocyte-derived dendritic cells from breast cancer patients are biased to induce CD4+CD25+Foxp3+ regulatory T cells. Journal of Leukocyte Biology (2012); 92(3), 673-682.

Rutella, S., Danese, S., & Leone, G. Tolerogenic dendritic cells: cytokine modulation comes of age. Blood (2006); 108(5), 1435-1440.

Figueiredo C R, Azevedo R A, Mousdell S, Resende-Lara P T, Ireland L, Santos A, Girola N, Cunha RLOR, Schmid M C, Polonelli L, Travassos L R and Mielgo A. Blockade of MIF-CD74 signalling on macrophages and dendritic cells restores the antitumour immune response against metastatic melanoma. Frontiers in Immunology (2018); 9:1132.

Choi S, Kim H R, Leng L, Kang I, Jorgensen W L, Cho C S, Bucala R, Kim W U. Role of macrophage migration inhibitory factor in the regulatory T cell response of tumor-bearing mice. The Journal of Immunolology (2012); 189:3905-3913.

Abe R, Peng T, Sailors J, Bucala R, Metz C N Regulation of the CTL response by macrophage migration inhibitory factor. The Journal of Immunology 2001; 166: 747-753

Nobre C C, de Araújo J M, Fernandes T A, Cobucci R N, Lanza D C, Andrade V S, Fernandes J V. Macrophage migration inhibitory factor (MIF): Biological activities and relation with cancer. Pathololgy & Oncology Research (2017); 23:235-244.

Leng L, Metz C N, Fang Y, Xu J, Donnelly S, Baugh J, Delohery T, Chen Y, Mitchell R A, Bucala R. MIF signal transduction initiated by binding to CD74. The Journal of Experimental Medicine (2003); 197:1467-1476.

The invention claimed is:

1. A method of modulating the immune system of a subject comprising:
   (i) contacting dendritic cells of the subject ex vivo with an effective amount of a peptide derived from the $V_H$CDR3 of a humanized antibody to NaPi2B, and
   (ii) administering the dendritic cells to the subject, thereby modulating the immune system of the subject;
   wherein the subject has cancer or is under cancer treatment,
   wherein the peptide is Rb9 (SEQ ID No. 1).

2. The method of claim 1, wherein the peptide modifies the phenotype of the dendritic cells of the subject, so as to reduce their functional bias and enhance their ability to induce T cell immune responses.

3. The method of claim 1, wherein over-stimulated dendritic cells are inhibited, poorly activated or suppressed dendritic cells are stimulated and balanced dendritic cells suffer no functional alteration.

4. The method according to claim 1, wherein the Rb9 peptide (SEQ ID: 1) is coupled with a Polyethylene glycol (PEG).

5. The method according to claim 1, wherein the cancer is melanoma.

6. A method of treating dendritic cells ex vivo, the method comprising contacting dendritic cells of a subject ex vivo with a peptide derived from the $V_H$CDR3 of a humanized antibody to NaPi2B, thereby treating the dendritic cells of the subject,
 wherein the subject has cancer or is under cancer treatment,
 wherein the peptide is Rb9 (SEQ ID No. 1).

7. The method of claim 6, wherein the peptide modifies the phenotype of the dendritic cells.

8. The method of claim 6, wherein over-stimulated dendritic cells are inhibited, poorly activated or suppressed dendritic cells are stimulated and balanced dendritic cells suffer no functional alteration.

\* \* \* \* \*

UNITED STATES PATENT AND TRADEMARK OFFICE
CERTIFICATE OF CORRECTION

PATENT NO. : 11,479,604 B2
APPLICATION NO. : 16/627924
DATED : October 25, 2022
INVENTOR(S) : Luiz Rodolpho Raja Gabaglia Travassos It is certified that error appears in the above-identified patent and that said Letters Patent is hereby corrected as shown below:

In the Drawings

Figure 6:
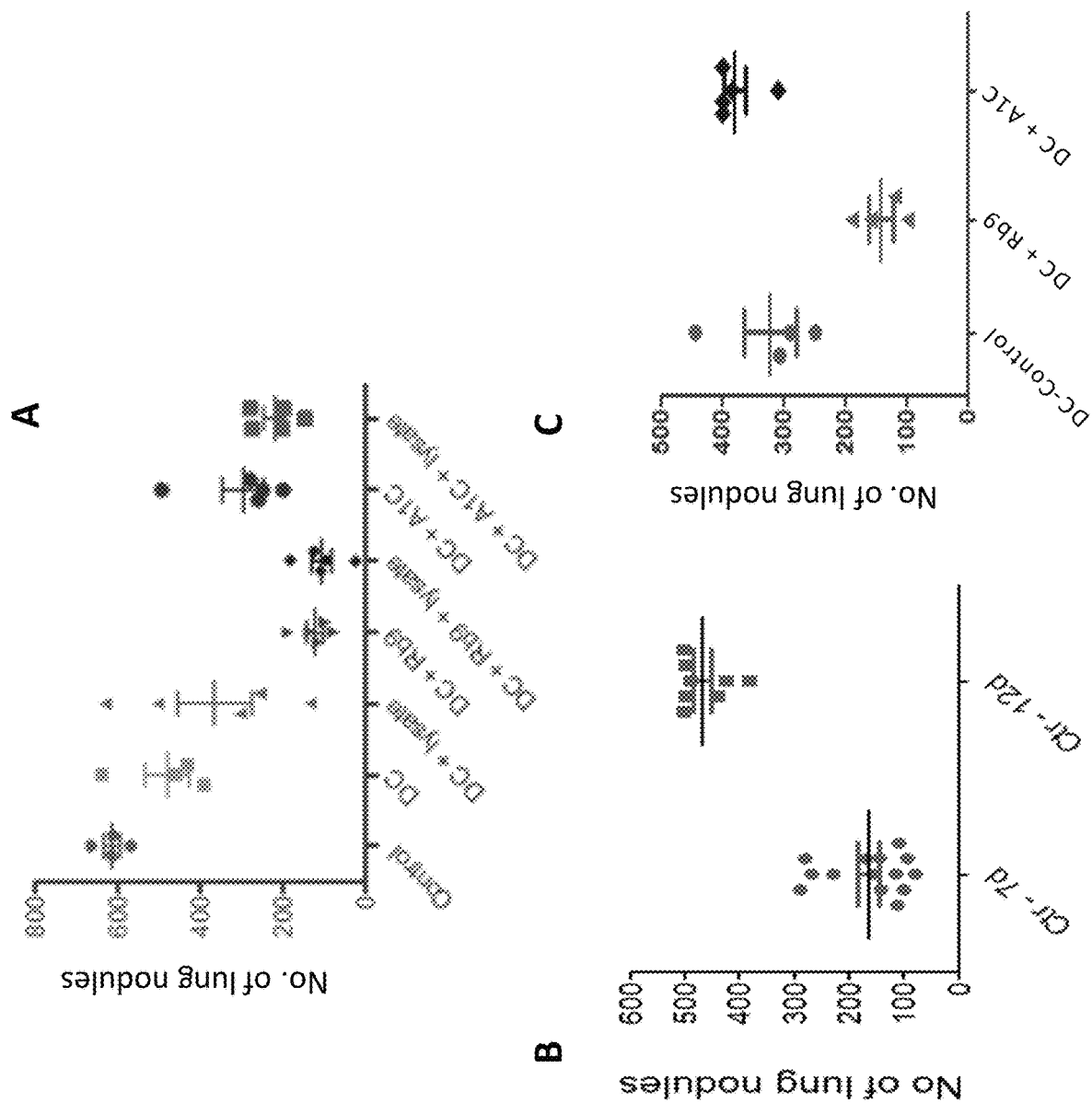
FIG. 6 shows that dendritic cells stimulated by Rb9 in a prophylactic protocol provide protection against metastatic melanoma. The linear A1C negative control in vitro was protective as a DC stimulant but less than Rb9. In a therapeutic protocol Rb9-stimulated DCs were administered 8 days after challenge with melanoma cells. A significant protection was seen as compared to unstimulated DCs or Rb10A1 treated DCs, comparing the number of lung nodules with clusters from 3 experiments of metastatic melanoma showing lung nodules after 7 days and after 12 days.

Sheet 6 of 35 (Figure 6.) (B (y-axis)), Line 1, delete "No" and insert -- No. --.

Sheet 8 of 35 (Figure 8.), Line 6 (approx.), delete "No" and insert -- No. --.

Sheet 21 of 35 (Figure 21) (B (y-axis)), Line 2, delete "Arbitraty" and insert -- Arbitrary --.

Sheet 25 of 35 (Figure 24B), Line 9 (approx.), delete "Treament" and insert -- Treatment --.

In the Specification

Column 4, Line 3, delete "activity" and insert -- activity. --.

Column 8, Line 53, delete "MHCII+" and insert -- MHCII+. --.

Column 13, Line 58, delete "Next" and insert -- Nex2 --.

Column 14, Line 67, delete "ml)" and insert -- ml), --.

Column 14, Line 67, delete "ml)." and insert -- ml), --.

Column 17, Line 24, delete "β," and insert -- β --.

Column 17, Line 51, delete "Cambrigde," and insert -- Cambridge, --.

Column 21, Line 30, after "during" insert -- 5 --.

Column 25, Line 33, delete "Immunulogy" and insert -- Immunology --.

Signed and Sealed this
Ninth Day of April, 2024

Katherine Kelly Vidal
*Director of the United States Patent and Trademark Office*

CERTIFICATE OF CORRECTION (continued)
U.S. Pat. No. 11,479,604 B2

Column 25, Line 43, delete "412" and insert -- 412. --.

Column 25, Line 53, delete "190" and insert -- 190. --.

Column 26, Line 3, delete "e8187" and insert -- e8187. --.

Column 26, Line 19, delete "964" and insert -- 964. --.

Column 27, Line 7, delete "Immunolology" and insert -- Immunology --.

Column 27, Line 11, delete "753" and insert -- 753. --.

Column 28, Line 4, delete "Patholology" and insert -- Pathology --.

```
                         SEQUENCE LISTING

<160> NUMBER OF SEQ ID NOS: 8

<210> SEQ ID NO 1
<211> LENGTH: 18
<212> TYPE: PRT
<213> ORGANISM: Artificial Sequence
<220> FEATURE:
<223> OTHER INFORMATION: Amidated and modified sequence of CDR H3 from
      ReMab 200 (huMX35), obtainable by a known method

<400> SEQUENCE: 1

Cys Ala Arg Gly Glu Thr Ala Arg Ala Thr Phe Ala Tyr Trp Gly Gln
1               5                   10                  15

Gly Cys

<210> SEQ ID NO 2
<211> LENGTH: 24
<212> TYPE: PRT
<213> ORGANISM: Artificial Sequence
<220> FEATURE:
<223> OTHER INFORMATION: Amidated and modified sequence of CDR H3 from
      ReMab 200 (huMX35), obtainable by a known method

<400> SEQUENCE: 2

Ala Arg Gly Ala Leu Ala Thr His Arg Pro His Glu Ala Leu Ala Thr
1               5                   10                  15

Tyr Arg Thr Arg Pro Gly Leu Tyr
            20

<210> SEQ ID NO 3
<211> LENGTH: 17
<212> TYPE: PRT
<213> ORGANISM: Artificial Sequence
<220> FEATURE:
<223> OTHER INFORMATION: Amidated and modified sequence of CDR H3 from
      RebMab 200 (hiMX35), obtainable by a known method

<400> SEQUENCE: 3

Cys Ala Arg Gly Glu Thr Ala Arg Ala Thr Phe Ala Tyr Trp Gly Gln
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: Amidated and modified sequence of CDR H3 from
      ReMab 200 (huMX35), obtainable by a known method

<400> SEQUENCE: 4

Ala Ala Arg Gly Glu Thr Ala Arg Ala Thr Phe Ala Tyr Trp Gly Gln
1               5                   10                  15
```

```
<210> SEQ ID NO 5
<211> LENGTH: 18
<212> TYPE: PRT
<213> ORGANISM: Artificial Sequence
<220> FEATURE:
<223> OTHER INFORMATION: Amidated and modified sequence of CDR H3 from
      ReMab 200 (huMX35), obtainable by a known method

<400> SEQUENCE: 5

Cys Ala Glu Ala Thr Tyr Trp Arg Arg Gly Gly Gln Ala Ala Gly Phe
1               5                   10                  15

Thr Cys

<210> SEQ ID NO 6
<211> LENGTH: 18
<212> TYPE: PRT
<213> ORGANISM: Artificial Sequence
<220> FEATURE:
<223> OTHER INFORMATION: Amidated and modified sequence of CDR H3 from
      ReMab 200 (huMX35), obtainable by a known method

<400> SEQUENCE: 6

Ala Glu Ala Cys Gly Gly Tyr Thr Arg Trp Arg Thr Cys Ala Gly Ala
1               5                   10                  15

Gln Phe

<210> SEQ ID NO 7
<211> LENGTH: 18
<212> TYPE: PRT
<213> ORGANISM: Artificial Sequence
<220> FEATURE:
<223> OTHER INFORMATION: Amidated and modified sequence of CDR H3 from
      ReMab 200 (huMX35), obtainable by a known method

<400> SEQUENCE: 7

Cys Glu Thr Trp Arg Gly Ala Ala Thr Arg Gly Ala Phe Gln Ala Tyr
1               5                   10                  15

Gly Cys

<210> SEQ ID NO 8
<211> LENGTH: 18
<212> TYPE: PRT
<213> ORGANISM: Artificial Sequence
<220> FEATURE:
<223> OTHER INFORMATION: Amidated and modified sequence of CDR H3 from
      ReMab 200 (huMX35), obtainable by a known method

<400> SEQUENCE: 8

Ala Cys Arg Gly Ala Gly Ala Thr Trp Thr Arg Gln Phe Glu Gly Ala
1               5                   10                  15

Cys Tyr
```